(12) United States Patent
McKeown

(10) Patent No.: US 11,459,606 B2
(45) Date of Patent: *Oct. 4, 2022

(54) ADAPTORS FOR NUCLEIC ACID CONSTRUCTS IN TRANSMEMBRANE SEQUENCING

(71) Applicant: Oxford Nanopore Technologies Ltd., Oxford (GB)

(72) Inventor: Brian McKeown, Oxfordshire (GB)

(73) Assignee: Oxford Nanopore Technologies PLC, Oxford (GB)

( * ) Notice: Subject to any disclaimer, the term of this patent is extended or adjusted under 35 U.S.C. 154(b) by 161 days.

This patent is subject to a terminal disclaimer.

(21) Appl. No.: 15/906,964

(22) Filed: Feb. 27, 2018

(65) Prior Publication Data

US 2018/0291440 A1    Oct. 11, 2018

Related U.S. Application Data

(63) Continuation of application No. 15/390,806, filed on Dec. 27, 2016, now abandoned, which is a continuation of application No. 13/147,159, filed as application No. PCT/GB2010/000160 on Jan. 29, 2010, now abandoned.

(60) Provisional application No. 61/148,737, filed on Jan. 30, 2009.

(51) Int. Cl.
*C12P 19/34* (2006.01)
*C12Q 1/6869* (2018.01)
*C07H 21/04* (2006.01)

(52) U.S. Cl.
CPC ......... *C12Q 1/6869* (2013.01); *C07H 21/04* (2013.01)

(58) Field of Classification Search
USPC ......... 435/6.1, 6.11, 6.12, 91.1, 91.2, 91.51; 436/94, 501; 536/23.1, 24.3, 24.33, 25.3, 536/25.32
See application file for complete search history.

(56) References Cited

U.S. PATENT DOCUMENTS

| 5,215,899 A | 6/1993 | Dattagupta |
| 5,424,413 A | 6/1995 | Hogan et al. |
| 5,561,043 A | 10/1996 | Cantor et al. |

(Continued)

FOREIGN PATENT DOCUMENTS

| CN | 101495656 | 7/2009 |
| CN | 102245760 | 11/2011 |

(Continued)

OTHER PUBLICATIONS

"multiplex sequencing". Printed on Nov. 4, 2021.*

(Continued)

*Primary Examiner* — Frank W Lu
(74) *Attorney, Agent, or Firm* — Wolf, Greenfield & Sacks, P.C.

(57) ABSTRACT

The invention relates to adaptors for sequencing nucleic acids. The adaptors may be used to generate single stranded constructs of nucleic acid for sequencing purposes. Such constructs may contain both strands from a double stranded deoxyribonucleic acid (DNA) or ribonucleic acid (RNA) template. The invention also relates to the constructs generated using the adaptors, methods of making the adaptors and constructs, as well as methods of sequencing double stranded nucleic acids.

6 Claims, 4 Drawing Sheets

Specification includes a Sequence Listing.

(56) References Cited

U.S. PATENT DOCUMENTS

| | | |
|---|---|---|
| 5,777,078 A | 7/1998 | Bayley et al. |
| 5,795,782 A | 8/1998 | Church et al. |
| 5,817,771 A | 10/1998 | Bayley et al. |
| 5,866,328 A | 2/1999 | Bensimon et al. |
| 5,866,336 A | 2/1999 | Nazarenko et al. |
| 5,985,834 A | 11/1999 | Engel et al. |
| 6,015,714 A | 1/2000 | Baldarelli et al. |
| 6,087,099 A | 7/2000 | Gupte et al. |
| 6,123,819 A | 9/2000 | Peeters |
| 6,127,166 A | 10/2000 | Bayley et al. |
| 6,251,610 B1 | 6/2001 | Gupte et al. |
| 6,362,002 B1 | 3/2002 | Denison et al. |
| 6,403,319 B1 | 6/2002 | Lizardi et al. |
| 6,426,231 B1 | 7/2002 | Bayley et al. |
| 6,451,563 B1 | 9/2002 | Wittig et al. |
| 6,465,193 B2 | 10/2002 | Akeson et al. |
| 6,627,067 B1 | 9/2003 | Branton et al. |
| 6,787,308 B2 | 9/2004 | Balasubramanian et al. |
| 6,824,659 B2 | 11/2004 | Bayley et al. |
| 6,863,833 B1 | 3/2005 | Bloom et al. |
| 6,916,665 B2 | 7/2005 | Bayley et al. |
| 6,927,070 B1 | 8/2005 | Bayley et al. |
| 7,087,729 B1 | 8/2006 | Prive |
| 7,189,503 B2 | 3/2007 | Akeson et al. |
| 7,238,485 B2 | 7/2007 | Akeson et al. |
| 7,361,466 B2 | 4/2008 | Korlach et al. |
| 7,507,575 B2 | 3/2009 | Bedingham et al. |
| 7,700,281 B2 | 4/2010 | Kubu et al. |
| 8,105,846 B2 | 1/2012 | Bayley et al. |
| 8,143,030 B2 | 3/2012 | Maxham et al. |
| 8,343,746 B2 | 1/2013 | Rank et al. |
| 8,383,369 B2 | 2/2013 | Maxham et al. |
| 8,628,940 B2 | 1/2014 | Sorenson et al. |
| 8,652,779 B2 | 2/2014 | Turner et al. |
| 8,785,211 B2 | 7/2014 | Bayley et al. |
| 8,822,160 B2 | 9/2014 | Bayley et al. |
| 8,889,348 B2 | 11/2014 | Ju |
| 9,057,102 B2 | 6/2015 | Turner et al. |
| 9,116,118 B2 | 8/2015 | Turner et al. |
| 9,145,623 B2 | 9/2015 | Kavanagh et al. |
| 9,150,918 B2 | 10/2015 | Turner et al. |
| 9,542,527 B2 | 1/2017 | Travers et al. |
| 9,546,400 B2 | 1/2017 | Turner et al. |
| 9,551,023 B2 | 1/2017 | Turner et al. |
| 9,556,480 B2 | 1/2017 | Turner et al. |
| 9,582,640 B2 * | 2/2017 | Travers ............... C12Q 1/6869 |
| 9,600,626 B2 * | 3/2017 | Travers ............... C12Q 1/6869 |
| 9,670,526 B2 | 6/2017 | Kokoris et al. |
| 9,678,056 B2 | 6/2017 | Turner et al. |
| 9,738,929 B2 | 8/2017 | Turner et al. |
| 9,957,560 B2 | 5/2018 | Brown et al. |
| 10,131,944 B2 | 11/2018 | Bernick et al. |
| 10,221,450 B2 | 3/2019 | Heron et al. |
| 10,501,767 B2 | 12/2019 | Stoddart et al. |
| 10,570,440 B2 | 2/2020 | White et al. |
| 10,597,713 B2 | 3/2020 | Brown et al. |
| 10,669,578 B2 | 6/2020 | Clarke et al. |
| 10,851,409 B2 | 12/2020 | Brown et al. |
| 11,155,860 B2 | 10/2021 | White et al. |
| 11,168,363 B2 | 11/2021 | Brown et al. |
| 11,186,857 B2 | 11/2021 | Stoddart et al. |
| 2001/0039039 A1 | 11/2001 | Weissman et al. |
| 2002/0028458 A1 | 3/2002 | Lexow |
| 2002/0094526 A1 | 7/2002 | Bayley et al. |
| 2002/0098530 A1 | 7/2002 | Pfeifer et al. |
| 2002/0132350 A1 | 9/2002 | Suzuki et al. |
| 2002/0142331 A1 | 10/2002 | Fu et al. |
| 2002/0177701 A1 | 11/2002 | Weissman et al. |
| 2002/0197618 A1 | 12/2002 | Sampson |
| 2003/0044816 A1 | 3/2003 | Denison et al. |
| 2003/0059778 A1 | 3/2003 | Berlin et al. |
| 2003/0087232 A1 | 5/2003 | Christians et al. |
| 2003/0099951 A1 | 5/2003 | Akeson et al. |
| 2003/0108902 A1 | 6/2003 | Abarzua |
| 2003/0118595 A1 | 6/2003 | Niemeyer et al. |
| 2003/0165936 A1 | 9/2003 | Rabbani et al. |
| 2003/0166137 A1 | 9/2003 | Zuker et al. |
| 2003/0211502 A1 | 11/2003 | Sauer et al. |
| 2003/0215881 A1 | 11/2003 | Bayley et al. |
| 2004/0055901 A1 | 3/2004 | Petersen et al. |
| 2004/0214177 A1 | 10/2004 | Bension |
| 2004/0229315 A1 | 11/2004 | Lee et al. |
| 2005/0042633 A1 | 2/2005 | Williams |
| 2005/0053961 A1 | 3/2005 | Akeson et al. |
| 2005/0142559 A1 | 6/2005 | Makrigiorgos |
| 2005/0221316 A1 | 10/2005 | Pedersen et al. |
| 2005/0227239 A1 | 10/2005 | Joyce |
| 2005/0260655 A1 | 11/2005 | Liu et al. |
| 2006/0063171 A1 | 3/2006 | Akeson et al. |
| 2006/0086626 A1 | 4/2006 | Joyce |
| 2006/0141516 A1 | 6/2006 | Kobold et al. |
| 2006/0147935 A1 | 7/2006 | Linnarsson |
| 2006/0292611 A1 | 12/2006 | Berka et al. |
| 2007/0015182 A1 | 1/2007 | Abarzua |
| 2007/0020640 A1 | 1/2007 | McCloskey |
| 2007/0031857 A1 | 2/2007 | Makarov et al. |
| 2007/0122885 A1 | 5/2007 | Reeves et al. |
| 2007/0224613 A1 | 9/2007 | Strathmann |
| 2007/0269825 A1 | 11/2007 | Wang et al. |
| 2007/0287151 A1 | 12/2007 | Linnarsson |
| 2008/0166724 A1 | 7/2008 | Gerber et al. |
| 2008/0206252 A1 | 8/2008 | Pennica et al. |
| 2008/0311582 A1 | 12/2008 | Bayley et al. |
| 2009/0098612 A1 | 4/2009 | Rhee et al. |
| 2009/0256116 A1 | 10/2009 | Shumaker-Parry et al. |
| 2009/0269771 A1 | 10/2009 | Schroeder |
| 2009/0280538 A1 | 11/2009 | Patel et al. |
| 2009/0298075 A1 * | 12/2009 | Travers ............... C12Q 1/6869 435/6.12 |
| 2010/0003560 A1 | 1/2010 | Shibata |
| 2010/0035260 A1 | 2/2010 | Olasagasti et al. |
| 2010/0075309 A1 | 3/2010 | Maxham et al. |
| 2010/0075327 A1 | 3/2010 | Maxham et al. |
| 2010/0092960 A1 | 4/2010 | Fehr |
| 2010/0120098 A1 | 5/2010 | Grunenwald et al. |
| 2010/0221212 A1 | 9/2010 | Stagliano et al. |
| 2010/0221716 A1 | 9/2010 | Flusberg et al. |
| 2010/0276588 A1 | 11/2010 | Syms |
| 2010/0331194 A1 | 12/2010 | Turner et al. |
| 2011/0019186 A1 | 1/2011 | Himmelhaus et al. |
| 2011/0124518 A1 | 5/2011 | Cantor |
| 2011/0136676 A1 | 6/2011 | Greene |
| 2011/0214991 A1 | 9/2011 | Kim et al. |
| 2011/0224106 A1 | 9/2011 | Eshoo et al. |
| 2011/0281768 A1 | 11/2011 | Travers et al. |
| 2011/0287435 A1 | 11/2011 | Grunenwald et al. |
| 2011/0311965 A1 | 12/2011 | Maglia et al. |
| 2012/0010085 A1 | 1/2012 | Rava et al. |
| 2012/0058468 A1 | 3/2012 | Mckeown |
| 2012/0100530 A1 | 4/2012 | Moysey et al. |
| 2012/0107802 A1 | 5/2012 | Stoddart et al. |
| 2012/0196279 A1 | 8/2012 | Underwood et al. |
| 2012/0244525 A1 | 9/2012 | Hendrickson |
| 2013/0017978 A1 | 1/2013 | Kavanagh et al. |
| 2013/0078624 A1 | 3/2013 | Holmes et al. |
| 2013/0143802 A1 | 6/2013 | Chilkoti |
| 2013/0195908 A1 | 8/2013 | Leonetti et al. |
| 2013/0327644 A1 | 12/2013 | Turner et al. |
| 2014/0134618 A1 | 5/2014 | Kokoris et al. |
| 2014/0134629 A1 | 5/2014 | Turner et al. |
| 2014/0186823 A1 | 7/2014 | Clarke et al. |
| 2014/0206842 A1 | 7/2014 | Majeed et al. |
| 2014/0262784 A1 | 9/2014 | Clarke et al. |
| 2014/0296089 A1 | 10/2014 | Holmes et al. |
| 2014/0308661 A1 | 10/2014 | Holmes et al. |
| 2015/0008126 A1 | 1/2015 | Maglia et al. |
| 2015/0045257 A1 | 2/2015 | Kavanagh et al. |
| 2015/0152492 A1 | 6/2015 | Brown et al. |
| 2015/0167075 A1 | 6/2015 | Turner et al. |
| 2015/0175663 A1 | 6/2015 | Yokoi et al. |
| 2015/0197796 A1 | 7/2015 | White et al. |
| 2015/0218629 A1 | 8/2015 | Heron et al. |
| 2015/0265994 A1 | 9/2015 | Hyde et al. |
| 2015/0285781 A1 | 10/2015 | Heron et al. |

(56) References Cited

U.S. PATENT DOCUMENTS

| | | |
|---|---|---|
| 2015/0307934 A1 | 10/2015 | Turner et al. |
| 2016/0010147 A1 | 1/2016 | Heron et al. |
| 2016/0010148 A1 | 1/2016 | Turner et al. |
| 2016/0011169 A1 | 1/2016 | Turner et al. |
| 2016/0194677 A1 | 7/2016 | Stoddart et al. |
| 2016/0257942 A1 | 9/2016 | Bruce et al. |
| 2016/0281159 A1 | 9/2016 | Brown et al. |
| 2016/0362739 A1 | 12/2016 | Brown et al. |
| 2017/0002406 A1 | 1/2017 | Bowen et al. |
| 2017/0067101 A1 | 3/2017 | Clarke et al. |
| 2017/0240955 A1 | 8/2017 | White |
| 2017/0314062 A1 | 11/2017 | Kokoris et al. |
| 2017/0321266 A1 | 11/2017 | Mckeown |
| 2018/0030506 A1 | 2/2018 | Fujioka |
| 2018/0291441 A1 | 10/2018 | Brown et al. |
| 2019/0194722 A1 | 6/2019 | Stoddart et al. |
| 2019/0211390 A1 | 7/2019 | Heron et al. |
| 2019/0376132 A1 | 12/2019 | Mckeown |
| 2020/0002761 A1 | 1/2020 | Mckeown |
| 2020/0024655 A1 | 1/2020 | Brown et al. |
| 2020/0032248 A1 | 1/2020 | White et al. |
| 2020/0131549 A1 | 4/2020 | Stoddart et al. |
| 2020/0239950 A1 | 7/2020 | Brown et al. |
| 2020/0291452 A1 | 9/2020 | White |
| 2020/0318179 A1 | 10/2020 | Clarke et al. |

FOREIGN PATENT DOCUMENTS

| | | |
|---|---|---|
| DE | 112016000293 T5 | 9/2017 |
| EP | 2682460 A1 | 1/2014 |
| EP | 3470529 A1 | 4/2019 |
| GB | 2130219 | 5/1984 |
| GB | 2237390 | 5/1991 |
| GB | 2453377 | 4/2009 |
| JP | H11-137260 | 5/1999 |
| JP | 2012-506704 A | 3/2012 |
| WO | WO 1994/023065 | 10/1994 |
| WO | WO 1999/005167 | 2/1999 |
| WO | WO 2000/028312 | 5/2000 |
| WO | WO 2001/040516 | 6/2001 |
| WO | WO 2001/042782 | 6/2001 |
| WO | WO 2001/059453 | 8/2001 |
| WO | WO 2002/042496 | 5/2002 |
| WO | WO 2003/095669 | 11/2003 |
| WO | WO 2005/056750 | 6/2005 |
| WO | WO 2005/068656 A1 | 7/2005 |
| WO | WO 2005/118877 | 12/2005 |
| WO | WO 2005/124888 | 12/2005 |
| WO | WO 2006/020775 | 2/2006 |
| WO | WO 2006/028508 | 3/2006 |
| WO | WO 2006/100484 | 9/2006 |
| WO | WO 2007/057668 | 5/2007 |
| WO | WO 2007/075987 | 7/2007 |
| WO | WO 2007/084103 | 7/2007 |
| WO | WO 2007/114693 A2 | 10/2007 |
| WO | WO 2007/146158 | 12/2007 |
| WO | WO 2008/045575 | 4/2008 |
| WO | WO 2008/083554 | 7/2008 |
| WO | WO 2008/102120 | 8/2008 |
| WO | WO 2008/102121 | 8/2008 |
| WO | WO 2008/124107 | 10/2008 |
| WO | WO 2009/035647 | 3/2009 |
| WO | WO 2009/044170 A1 | 4/2009 |
| WO | WO 2009/077734 A2 | 6/2009 |
| WO | WO 2009/120372 A2 | 10/2009 |
| WO | WO 2010/004265 | 1/2010 |
| WO | WO 2010/004273 | 1/2010 |
| WO | WO 2010/030683 A1 | 3/2010 |
| WO | WO 2010/034018 | 3/2010 |
| WO | WO 2010/048605 A1 | 4/2010 |
| WO | WO 2010/051773 | 5/2010 |
| WO | WO 2010/086602 A1 | 8/2010 |
| WO | WO 2010/086603 | 8/2010 |
| WO | WO 2010/086622 | 8/2010 |
| WO | WO 2010/094040 | 8/2010 |
| WO | WO 2010/109107 A1 | 9/2010 |
| WO | WO 2010/109197 | 9/2010 |
| WO | WO 2010/122293 | 10/2010 |
| WO | WO 2010/146349 A1 | 12/2010 |
| WO | WO 2011/067559 | 6/2011 |
| WO | WO 2012/033524 A2 | 3/2012 |
| WO | WO 2012/061832 | 5/2012 |
| WO | WO 2012/083249 A2 | 6/2012 |
| WO | WO 2012/098561 A2 | 7/2012 |
| WO | WO 2012/098562 A2 | 7/2012 |
| WO | WO 2012/103545 A1 | 8/2012 |
| WO | WO 2012/107778 A2 | 8/2012 |
| WO | WO 2012/164270 A1 | 12/2012 |
| WO | WO 2013/014451 A1 | 1/2013 |
| WO | WO 2013/041878 A1 | 3/2013 |
| WO | WO 2013/057495 A2 | 4/2013 |
| WO | WO 2013/098561 A1 | 7/2013 |
| WO | WO 2013/098562 A2 | 7/2013 |
| WO | WO 2013/131962 A1 | 9/2013 |
| WO | WO 2013/153359 A1 | 10/2013 |
| WO | WO 2013/185137 A1 | 12/2013 |
| WO | WO 2014/013259 A1 | 1/2014 |
| WO | WO 2014/013260 A1 | 1/2014 |
| WO | WO 2014/013262 A1 | 1/2014 |
| WO | WO 2014/108810 A2 | 7/2014 |
| WO | WO 2014/135838 A1 | 9/2014 |
| WO | WO 2014/153408 A1 | 9/2014 |
| WO | WO 2015/022544 A1 | 2/2015 |
| WO | WO 2015/031909 A1 | 3/2015 |
| WO | WO 2015/055981 A2 | 4/2015 |
| WO | WO 2015/056028 A1 | 4/2015 |
| WO | WO 2015/110777 A1 | 7/2015 |
| WO | WO 2015/110813 A1 | 7/2015 |
| WO | WO 2015/189636 A1 | 12/2015 |
| WO | WO 2015/200609 A1 | 12/2015 |
| WO | WO 2016/003814 A1 | 1/2016 |
| WO | WO 2016/022557 A1 | 2/2016 |
| WO | WO 2016/028887 A1 | 2/2016 |
| WO | WO 2016/059363 A1 | 4/2016 |
| WO | WO 2017/215500 A1 | 12/2017 |

OTHER PUBLICATIONS

"Single-molecule real-time sequencing" from Wikipedia. Printed on Nov. 4, 2021.*

Akeson et al., Microsecond time-scale discrimination among polycytidylic acid, polyadenylic acid, and polyuridylic acid as homopolymers or as segments within single RNA molecules. Biophys J. Dec. 1999;77(6):3227-33.

Altschul et al., Basic local alignment search tool. J Mol Biol. Oct. 5, 1990;215(3):403-10.

Altschul, A protein alignment scoring system sensitive at all evolutionary distances. J Mol Evol. Mar. 1993;36(3):290-300.

Amblard et al., Cu(I)-catalyzed Huisgen azide-alkyne 1,3-dipolar cycloaddition reaction in nucleoside, nucleotide, and oligonucleotide chemistry. Chem Rev. Sep. 2009;109(9):4207-20. doi: 10.1021/cr9001462.

Ashkenasy et al., Recognizing a single base in an individual DNA strand: a step toward DNA sequencing in nanopores. Angew Chem Int Ed Engl. Feb. 18, 2005;44(9):1401-4.

Ashkenasy et al., Single Nucleobase Sensitivity of a-Hemolysin (a-HL) Transmembrane Protein Pore: Toward Single DNA Sequencing. ACS National Meeting. 2005;45(13), Abstract No. 74.

Astier et al., Stochastic detection of motor protein-RNA complexes by single-channel current recording. Chemphyschem. Oct. 22, 2007;8(15):2189-94.

Astier et al., Toward single molecule DNA sequencing: direct identification of ribonucleoside and deoxyribonucleoside 5'-monophosphates by using an engineered protein nanopore equipped with a molecular adapter. J Am Chem Soc. Feb. 8, 2006;128(5):1705-10.

Avrameas, Coupling of enzymes to proteins with glutaraldehyde. Use of the conjugates for the detection of antigens and antibodies. Immunochemistry. Jan. 1969;6(1):43-52.

Bayley et al., Stochastic sensors inspired by biology. Nature. Sep. 13, 2001;413(6852):226-30.

(56) References Cited

OTHER PUBLICATIONS

Bayley, Sequencing single molecules of DNA. Curr Opin Chem Biol. Dec. 2006;10(6):628-37. Epub Nov. 20, 2006.

Benner et al., Sequence-specific detection of individual DNA polymerase complexes in real time using a nanopore. Nat Nanotechnol. Nov. 2007;2(11):718-24. doi: 10.1038/nnano.2007.344. Epub Oct. 28, 2007.

Berger et al., Universal bases for hybridization, replication and chain termination. Nucleic Acids Res. Aug. 1, 2000;28(15):2911-4.

Bowie et al., Deciphering the message in protein sequences: tolerance to amino acid substitutions. Science. Mar. 16, 1990;247(4948):1306-10.

Braha et al., Carriers versus adapters in stochastic sensing. Chemphyschem. May 2005;6(5):889-92.

Braha et al., Designed protein pores as components for biosensors. Chem Biol. Jul. 1997;4(7):497-505.

Branton et al., The potential and challenges of nanopore sequencing. Nat Biotechnol. Oct. 2008;26(10):1146-53. doi: 10.1038/nbt.1495.

Braslavsky et al., Sequence information can be obtained from single DNA molecules. Proc Natl Acad Sci U S A. Apr. 1, 2003;100(7):3960-4. Epub Mar. 21, 2003.

Budanova et al., Heptakis(6-amino-6-deoxy)-beta-cyclodextrin as a chiral selector for the separation of anionic analyte enantiomers by capillary electrophoresis. Electrophoresis. Aug. 2004;25(16):2795-800.

Burgess et al., Possible dissociation of the heparin-binding and mitogenic activities of heparin-binding (acidic fibroblast) growth factor-1 from its receptor-binding activities by site-directed mutagenesis of a single lysine residue. J Cell Biol. Nov. 1990;111(5 Pt 1):2129-38.

Busam, Structure of *Escherichia coli* exonuclease I in complex with thymidine 5'-monophosphate. Acta Crystallogr D Biol Crystallogr. Feb. 2008;64(Pt 2):206-10. doi: 10.1107/S090744490706012X. Epub Jan. 16, 2008.

Butler et al., Determination of RNA orientation during translocation through a biological nanopore. Biophys J. Jan. 1, 2006;90(1):190-9. Epub Oct. 7, 2005.

Butler et al., Single-molecule DNA detection with an engineered MspA protein nanopore. Proc Natl Acad Sci U S A. Dec. 30, 2008;105(52):20647-52. doi: 10.1073/pnas.0807514106. Epub Dec. 19, 2008.

Case 1:17-cv-00275-LPS Document 18. Notice of subsequent events relating to Oxford's motion to dismiss (D.I. 9). Oct. 18, 2017.

Case 1:17-cv-00275-LPS Document 19. Oxford Nanopore Technologies, Inc.'s response to Pacific Biosciences of California, Inc.'s notice of subsequent events. Oct. 24, 2017.

Case 1:17-cv-00275-RGA Document 10. Oxford's opening brief in support of its motion to dismiss PacBio's complaint for patent infringement. May 8, 2017.

Case 1:17-cv-00275-RGA Document 14. PacBio's response to Oxford's motion to dismiss. Jun. 5, 2017.

Case 1:17-cv-00275-RGA Document 16. Oxford's reply brief in support of its motion to dismiss PacBio's complaint for patent infringement. Jun. 26, 2017.

Case 1:17-cv-01353-LPS Document 13. First Amended Complaint for Patent Infringement. Nov. 30, 2017.

Case 1:17-cv-01353-LPS Document 15. Plaintiff's response to Oxford Nanopore Techologies, Inc.'s Motion to Dismiss and Request for Scheduling Conference. Nov. 30, 2017.

Case 1:17-cv-01353-RGA Document 10. Oxford's opening brief in support of its motion to partially dismiss Pacbio's complaint for patent infringement. Nov. 16, 2017.

United States District Court for the District of Delaware Order. *Pacific Biosciences of California, Inc.* v. *Oxford Nanopore Technolgoies, Inc.* Civil Action No. 17-275-RGA. Nov. 9, 2017.

Chan, Advances in sequencing technology. Mutat Res. Jun. 3, 2005;573(1-2):13-40.

Cheley et al., A functional protein pore with a "retro" transmembrane domain. Protein Sci. Jun. 1999;8(6):1257-67.

Cheley et al., A genetically encoded pore for the stochastic detection of a protein kinase. Chembiochem. Dec. 2006;7(12):1923-7.

Cheley et al., Spontaneous oligomerization of a staphylococcal alpha-hemolysin conformationally constrained by removal of residues that form the transmembrane beta-barrel. Protein Eng. Dec. 1997;10(12):1433-43.

Cheley et al., Stochastic sensing of nanomolar inositol 1,4,5-trisphosphate with an engineered pore. Chem Biol. Jul. 2002;9(7):829-38.

Chen et al., Atomic Layer Deposition to Fine-Tune the Surface Properties and Diameters of Fabricated Nanopores. Nano Lett. Jun. 25, 2004;4(7):1333-1337.

Chen et al., Outer membrane protein G: Engineering a quiet pore for biosensing. Proc Natl Acad Sci U S A. Apr. 29, 2008;105(17):6272-7. doi: 10.1073/pnas.0711561105. Epub Apr. 28, 2008.

Clarke et al., Continuous base identification for single-molecule nanopore DNA sequencing. Nat Nanotechnol. Apr. 2009;4(4):265-70. doi: 10.1038/nnano.2009.12. Epub Feb. 22, 2009.

Cockroft et al., A single-molecule nanopore device detects DNA polymerase activity with single-nucleotide resolution. J Am Chem Soc. Jan. 23, 2008;130(3):818-20. doi: 10.1021/ja077082c. Epub Jan. 1, 2008.

Comai et al., Protein engineering modulates the transport properties and ion selectivity of the pores formed by staphylococcal gamma-haemolysins in lipid membranes. Mol Microbiol. Jun. 2002;44(5):1251-67.

Comer et al., Microscopic mechanics of hairpin DNA translocation through synthetic nanopores. Biophys J. Jan. 2009;96(2):593-608. doi: 10.1016/j.bpj.2008.09.023.

Cudic et al., Binding of Nucleotides in Water by Phenathridinium Bis(intercaland) Receptor Molecules. J. Chem. Soc., Chem. Commun., pp. 1073-1075 (1995).

Dapprich, Single-molecule DNA digestion by lambda-exonuclease. Cytometry. Jul. 1, 1999;36(3):163-8.

Deamer et al., Characterization of nucleic acids by nanopore analysis. Acc Chem Res. Oct. 2002;35(10):817-25.

Deamer et al., Nanopores and nucleic acids: prospects for ultrarapid sequencing. Trends Biotechnol. Apr. 2000;18(4):147-51.

Derrington et al., Nanopore DNA sequencing with MspA. Proc Natl Acad Sci U S A. Sep. 14, 2010;107(37):16060-5. doi: 10.1073/pnas.1001831107. Epub Aug. 26, 2010.

Devereux et al., A comprehensive set of sequence analysis programs for the VAX. Nucleic Acids Res. Jan. 11, 1984;12(1 Pt 1):387-95.

Dorre et al., Techniques for single molecule sequencing. Bioimaging, vol. 5:139-152 (1997).

Eid et al., Real-time DNA sequencing from single polymerase molecules. Science. Jan. 2, 2009;323(5910):133-8. doi: 10.1126/science.1162986. Epub Nov. 20, 2008.

Eliseev et al., Aminocyclodextrins as Selective Hosts with Several Binding Sites for Nucleotides. Angew. Chem. Int. Ed. Engl., vol. 32(9):1331-1333 (1993).

Eliseev et al., Molecular Recognition of Nucleotides, Nucleosides, and Sugars by Aminocyclodextrins. J. Am. Chem. Soc., vol. 116:6081-6088 (1994).

El-Sagheer et al., Synthesis and polymerase chain reaction amplification of DNA strands containing an unnatural triazole linkage. J Am Chem Soc. Mar. 25, 2009;131(11):3958-64. doi: 10.1021/ja8065896.

Erie et al., A dumbbell-shaped, double-hairpin structure of DNA: a thermodynamic investigation. Biochemistry. Nov. 3, 1987;26(22):7150-9.

Flomenbom et al., Single stranded DNA translocation through a nanopore: a master equation approach. Phys Rev E Stat Nonlin Soft Matter Phys. Oct. 2003;68(4 Pt 1):041910. Epub Oct. 14, 2003.

Flusberg et al., Direct detection of DNA methylation during single-molecule, real-time sequencing. Nat Methods. Jun. 2010;7(6):461-5. doi: 10.1038/nmeth.1459. Epub May 9, 2010.

Genschel et al., Interaction of *E. coli* single-stranded DNA binding protein (SSB) with exonuclease I. The carboxy-terminus of SSB is the recognition site for the nuclease. Biol Chem. Mar. 2000;381(3):183-92.

(56) References Cited

OTHER PUBLICATIONS

Gershow et al., Recapturing and trapping single molecules with a solid-state nanopore. Nat Nanotechnol. Dec. 2007;2(12):775-9. doi:10.1038/nnano.2007.381. Epub Dec. 2, 2007.

Ghosal, Electrokinetic-flow-induced viscous drag on a tethered DNA inside a nanopore. Phys Rev E Stat Nonlin Soft Matter Phys. Dec. 2007;76(6 Pt 1):061916. Epub Dec. 26, 2007.

Gonzalez-Perez et al., Biomimetic triblock copolymer membrane arrays: a stable template for functional membrane proteins. Langmuir. Sep. 15, 2009;25(18):10447-50. doi: 10.1021/la902417m.

Grant et al., A facile method for attaching nitroxide spin labels at the 5' terminus of nucleic acids. Nucleic Acids Res. 2007;35(10):e77. Epub May 21, 2007.

Gu et al., Capture of a single molecule in a nanocavity. Science. Jan. 26, 2001;291(5504):636-40.

Gu et al., Electroosmotic enhancement of the binding of a neutral molecule to a transmembrane pore. Proc Natl Acad Sci U S A. Dec. 23, 2003;100(26):15498-503. Epub Dec. 15, 2003.

Gu et al., Prolonged residence time of a noncovalent molecular adapter, beta-cyclodextrin, within the lumen of mutant alpha-hemolysin pores. J Gen Physiol. Nov. 2001;118(5):481-94.

Gu et al., Reversal of charge selectivity in transmembrane protein pores by using noncovalent molecular adapters. Proc Natl Acad Sci U S A. Apr. 11, 2000;97(8):3959-64.

Gu et al., Single molecule sensing by nanopores and nanopore devices. Analyst. Mar. 2010;135(3):441-51. doi: 10.1039/b907735a. Epub Dec. 22, 2009.

Gu et al., Stochastic sensing of organic analytes by a pore-forming protein containing a molecular adapter. Nature. Apr. 22, 1999;398(6729):686-90.

Guan et al., Stochastic sensing of TNT with a genetically engineered pore. Chembiochem. Oct. 2005;6(10):1875-81.

Han et al., Characterization and optimization of an entropic trap for DNA separation. Anal Chem. Jan. 15, 2002;74(2):394-401.

Han et al., RecJ exonuclease: substrates, products and interaction with SSB. Nucleic Acids Res. Feb. 18, 2006;34(4):1084-91. Print 2006.

Hein et al., Click chemistry, a powerful tool for pharmaceutical sciences. Pharm Res. Oct. 2008;25(10):2216-30. doi: 10.1007/s11095-008-9616-1. Epub May 29, 2008.

Henrickson et al., Driven DNA transport into an asymmetric nanometer-scale pore. Phys Rev Lett. Oct. 2, 2000;85(14):3057-60.

Heredia et al., In vitro double transposition for DNA identification. Anal Biochem. Apr. 1, 2010;399(1):78-83. doi:10.1016/j.ab.2009.11.030. Epub Nov. 26, 2009.

Holden et al., Direct introduction of single protein channels and pores into lipid bilayers. J Am Chem Soc. May 11, 2005;127(18):6502-3.

Holden et al., Functional bionetworks from nanoliter water droplets. J Am Chem Soc. Jul. 11, 2007;129(27):8650-5. Epub Jun. 16, 2007.

Hornblower et al., Single-molecule analysis of DNA-protein complexes using nanopores. Nat Methods. Apr. 2007;4(4):315-7. Epub Mar. 4, 2007.

Howorka et al., DNA Duplex Formation of Individual DNA Strands within a Single Protein Pore. Biophysical Journal, vol. 82{ 1, pt. 2):508a, No. 2482-Plat (2002).

Howorka et al., Improved protocol for high-throughput cysteine scanning mutagenesis. Biotechniques. Nov. 1998;25(5):764-6, 768, 770 passim.

Howorka et al., Kinetics of duplex formation for individual DNA strands within a single protein nanopore. Proc Natl Acad Sci U S A. Nov. 6, 2001;98(23):12996-3001. Epub Oct. 23, 2001.

Howorka et al., Probing distance and electrical potential within a protein pore with tethered DNA. Biophys J. Dec. 2002;83(6):3202-10.

Howorka et al., Sequence-specific detection of individual DNA strands using engineered nanopores. Nat Biotechnol. Jul. 2001;19(7):636-9.

Hu et al., Theory of DNA translocation through narrow ion channels and nanopores with charged walls. Phys Rev E Stat Nonlin Soft Matter Phys. Sep. 2008;78(3 Pt 1):032901. Epub Sep. 10, 2008.

Hwang et al., Electrical behavior of droplet interface bilayer networks: experimental analysis and modeling. J Am Chem Soc. Sep. 26, 2007;129(38):11854-64. Epub Sep. 1, 2007.

Jayasinghe et al., The leukocidin pore: evidence for an octamer with four LukF subunits and four LukS subunits alternating around a central axis. Protein Sci. Oct. 2005;14(10):2550-61.

Jung et al., The internal cavity of the staphylococcal alpha-hemolysin pore accommodates approximately 175 exogenous amino acid residues. Biochemistry. Jun. 28, 2005;44(25):8919-29.

Kalisch et al., Covalently linked sequencing primer linkers (splinkers) for sequence analysis of restriction fragments. Gene. 1986;44(2-3):263-70.

Kanan et al., Reaction discovery enabled by DNA-templated synthesis and in vitro selection. Nature. Sep. 30, 2004;431(7008):545-9.

Kang et al., Single protein pores containing molecular adapters at high temperatures. Angew Chem Int Ed Engl. Feb. 25, 2005;44(10):1495-9.

Kasianowicz et al., Characterization of individual polynucleotide molecules using a membrane channel. Proc Natl Acad Sci U S A. Nov. 26, 1996;93(24):13770-3.

Keyser, Controlling molecular transport through nanopores. J R Soc Interface. Oct. 7, 2011;8(63):1369-78. doi: 10.1098/rsif.2011.0222. Epub Jun. 29, 2011.

Khulbe et al., DNA translocation through a-hemolysin nanopores with potential application to macromolecular data storage. Journal Applied Physics, vol. 97(104317):1-7 (2005).

Kocalka et al., Rapid and efficient DNA strand cross-linking by click chemistry. Chembiochem. May 23, 2008;9(8):1280-5. doi:10.1002/cbic.200800006.

Kolb et al., Click Chemistry: Diverse Chemical Function from a Few Good Reactions. Angew Chem Int Ed Engl. Jun. 1, 2001;40(11):2004-2021.

Kovall et al., Toroidal structure of lambda-exonuclease. Science. Sep. 19, 1997;277(5333):1824-7.

Langecker et al., Synthetic lipid membrane channels formed by designed DNA nanostructures. Science. Nov. 16, 2012;338(6109):932-6. doi: 10.1126/science.1225624.

Lazar et al., Transforming growth factor alpha: mutation of aspartic acid 47 and leucine 48 results in different biological activities. Mol Cell Biol. Mar. 1988;8(3):1247-52.

Li et al., DNA molecules and configurations in a solid-state nanopore microscope. Nat Mater. Sep. 2003;2(9):611-5. Epub Aug. 24, 2003.

Lieberman et al., Processive replication of single DNA molecules in a nanopore catalyzed by phi29 DNA polymerase. J Am Chem Soc. Dec. 22, 2010;132(50):17961-72. doi:10.1021/jal087612. Epub Dec. 1, 2010.

Lovett et al., Identification and purification of a single-stranded-DNA-specific exonuclease encoded by the recJ gene of *Escherichia coli*. Proc Natl Acad Sci U S A. Apr. 1989;86(8):2627-31.

Lovrinovic et al., Rapid synthesis of DNA-cysteine conjugates for expressed protein ligation. Biochem Biophys Res Commun. Sep. 30, 2005;335(3):943-8.

Luo et al., Influence of polymer-pore interactions on translocation. Phys Rev Lett. Oct. 5, 2007;99(14):148102. Epub Oct. 1, 2007.

Lutz et al., Efficient construction of therapeutics, bioconjugates, biomaterials and bioactive surfaces using azide-alkyne "click" chemistry. Adv Drug Deliv Rev. Jun. 10, 2008;60(9):958-70. doi: 10.1016/j.addr.2008.02.004. Epub Mar. 4, 2008.

Maglia et al., Analysis of single nucleic acid molecules with protein nanopores. Methods Enzymol. 2010;475:591-623. doi: 10.1016/S0076-6879(10)75022-9.

Maglia et al., Enhanced translocation of single DNA molecules through alpha-hemolysin nanopores by manipulation of internal charge. Proc Natl Acad Sci U S A. Dec. 16, 2008; 105(50):19720-5. doi:10.1073/pnas.0808296105. Epub Dec. 5, 2008.

Martin et al., Nanoscale protein pores modified with PAMAM dendrimers. J Am Chem Soc. Aug. 8, 2007;129(31):9640-9. Epub Jul. 18, 2007.

(56) References Cited

OTHER PUBLICATIONS

Martinez et al., The mRNA cap structure stimulates rate of poly(A) removal and amplifies processivity of degradation. J Biol Chem. Jul. 27, 2001;276(30):27923-9. Epub May 18, 2001.
Marziali et al., New DNA sequencing methods. Annu Rev Biomed Eng. 2001;3:195-223.
Mathé et al., Orientation discrimination of single-stranded DNA inside the alpha-hemolysin membrane channel. Proc Natl Acad Sci U S A. Aug. 30, 2005;102(35):12377-82. Epub Aug. 19, 2005.
Matsuura et al., Real-time observation of a single DNA digestion by lambda exonuclease under a fluorescence microscope field. Nucleic Acids Res. Aug. 15, 2001;29(16):E79.
Meller et al., Rapid nanopore discrimination between single polynucleotide molecules. Proc Natl Acad Sci U S A. Feb. 1, 2000;97(3):1079-84.
Meller et al., Single molecule measurements of DNA transport through a nanopore. Electrophoresis. Aug. 2002;23(16):2583-91.
Meller, Dynamics of polynucleotide transport through nanometre-scale pores. Journal Physics: Condensed Matter, vol. 15:R581-R607 (2003).
Merzlyak et al., Conductance and ion selectivity of a mesoscopic protein nanopore probed with cysteine scanning mutagenesis. Biophys J. Nov. 2005;89(5):3059-70. Epub Aug. 5, 2005.
Miles et al., Single molecule sensing with solid-state nanopores: novel materials, methods, and applications. Chem Soc Rev. Jan. 7, 2013;42(1):15-28. doi: 10.1039/c2cs35286a. Epub Sep. 19, 2012.
Mitchell et al., Chemical tags facilitate the sensing of individual DNA strands with nanopores. Angew Chem Int Ed Engl. 2008;47(30):5565-8. doi:10.1002/anie.200800183.
Mohammad et al., Controlling a single protein in a nanopore through electrostatic traps. J Am Chem Soc. Mar. 26, 2008;130(12):4081-8. doi: 10.1021/ja710787a. Epub Mar. 6, 2008.
Mol et al., Structure and function of the multifunctional DNA-repair enzyme exonuclease III. Nature. Mar. 23, 1995;374(6520):381-6.
Montal et al., Formation of bimolecular membranes from lipid monolayers and a study of their electrical properties. Proc Natl Acad Sci U S A. Dec. 1972;69(12):3561-6.
Movileanu et al., Detecting protein analytes that modulate transmembrane movement of a polymer chain within a single protein pore. Nat Biotechnol. Oct. 2000;18(10):1091-5.
Movileanu et al., Location of a constriction in the lumen of a transmembrane pore by targeted covalent attachment of polymer molecules. J Gen Physiol. Mar. 2001;117(3):239-52.
Muller et al., DNA-directed assembly of artificial multienzyme complexes. Biochem Biophys Res Commun. Dec. 5, 2008;377(1):62-7. doi:10.1016/j.bbrc.2008.09.078. Epub Sep. 25, 2008.
Nakane et al., A nanosensor for transmembrane capture and identification of single nucleic Acid molecules. Biophys J. Jul. 2004;87(1):615-21. Erratum in: Biophys J. Nov. 2004;87(5):3618.
Nakane et al., Nanopore sensors for nucleic acid analysis. J. Phys.: Condens. Matter, vol. 15: R1365-R1393 (2003).
Niemeyer et al., DNA-directed assembly of bienzymic complexes from in vivo biotinylated NAD(P)H:FMN oxidoreductase and luciferase. Chembiochem. Mar. 1, 2002;3(2-3):242-5.
Nikolov et al., Behavior of giant vesicles with anchored DNA molecules. Biophys J. Jun. 15, 2007;92(12):4356-68. Epub Mar. 23, 2007.
Nwe et al., Growing applications of "click chemistry" for bioconjugation in contemporary biomedical research. Cancer Biother Radiopharm. Jun. 2009;24(3):289-302. doi: 10.1089/cbr.2008.0626.
Paner et al., Studies of DNA dumbbells. III. Theoretical analysis of optical melting curves of dumbbells with a 16 base-pair duplex stem and Tn end loops (n = 2, 3, 4, 6, 8, 10, 14). Biopolymers. Jul. 1992;32(7):881-92.
Paner et al., Studies of DNA dumbbells. VI. Analysis of optical melting curves of dumbbells with a sixteen-base pair duplex stem and end-loops of variable size and sequence. Biopolymers. Dec. 1996;39(6):779-93.
Phoenix et al., OmpF-Lpp signal sequence mutants with varying charge hydrophobicity ratios provide evidence for a phosphatidylglycerol-signal sequence interaction during protein translocation across the *Escherichia coli* inner membrane. J Biol Chem. Aug. 15, 1993;268(23):17069-73.
Purnell et al., Nucleotide identification and orientation discrimination of DNA homopolymers immobilized in a protein nanopore. Nano Lett. Sep. 2008;8(9):3029-34. doi: 10.1021/nl802312f. Epub Aug. 13, 2008.
Sanchez-Quesada et al., Cyclic Peptides as Molecular Adapters for a Pore-Forming Protein. Journal American Chemical Society, vol. 122(48):11757-11766 (2000).
Sanchez-Quesada et al., Single DNA rotaxanes of a transmembrane pore protein. Angew Chem Int Ed Engl. Jun. 7, 2004;43(23):3063-7.
Sanderson, Personal genomes: Standard and pores. Nature. Nov. 6, 2008;456(7218):23-5. doi: 10.1038/456023a.
Sauer-Budge et al., Unzipping kinetics of double-stranded DNA in a nanopore. Phys Rev Lett. Jun. 13, 2003;90(23):238101. Epub Jun. 9, 2003.
Schneider et al., DNA sequencing with nanopores. Nat Biotechnol. Apr. 10, 2012;30(4):326-8. doi: 10.1038/nbt.2181.
Seeman, Nucleic acid junctions and lattices. J Theor Biol. Nov. 21, 1982;99(2):237-47.
Seo et al., Click chemistry to construct fluorescent oligonucleotides for DNA sequencing. J Org Chem. Jan. 24, 2003;68(2):609-12.
Seol et al., Stretching of homopolymeric RNA reveals single-stranded helices and base-stacking. Phys Rev Lett. Apr. 13, 2007;98(15):158103. Epub Apr. 12, 2007.
Shank et al., Redesigning channel-forming peptides: amino acid substitutions that enhance rates of supramolecular self-assembly and raise ion transport activity. Biophys J. Mar. 15, 2006;90(6):2138-50. Epub Dec. 30, 2005.
Shin et al., Kinetics of a reversible covalent-bond-forming reaction observed at the singlemolecule level. Angew Chem Int Ed Engl. Oct. 4, 2002;41(19):3707-9; 3523.
Smeets et al., Salt dependence of ion transport and DNA translocation through solid-state nanopores. Nano Lett. Jan. 2006;6(1):89-95.
Song et al., Structure of staphylococcal alpha-hemolysin, a heptameric transmembrane pore. Science. Dec. 13, 1996;274(5294):1859-66.
Stoddart et al., Multiple base-recognition sites in a biological nanopore: two heads are better than one. Angew Chem Int Ed Engl. 2010;49(3):556-9. doi: 10.1002/anie.200905483.
Stoddart et al., Single-nucleotide discrimination in immobilized DNA oligonucleotides with a biological nanopore. Proc Natl Acad Sci U S A. May 12, 2009;106(19):7702-7. doi: 10.1073/pnas.0901054106. Epub Apr. 20, 2009.
Sutherland et al., An analysis of mismatched duplex DNA unzipping through a bacterial nanopore. Biochem Cell Biol. Jun. 2004;82(3):407-12.
Tanya et al., Capillary electrophoretic separation of nucleotide isomers via complexation with cyclodextrin and borate. J Chromatogr B Biomed Appl. Jul. 15, 1994;657(2):365-72.
Thomas et al., Processivity of DNA exonucleases. J Biol Chem. Jan. 25, 1978;253(2):424-9.
Tohda et al., "Channel Mimetic Sensing Membranes for Nucleotides Based on Multitopic Hydrogen Bonding," Israel Journal of Chemistry, vol. 37:267-275 (1997).
Travers et al., A flexible and efficient template format for circular consensus sequencing and SNP detection. Nucleic Acids Res. Aug. 2010;38(15):e159. doi: 10.1093/nar/gkq543. Epub Jun. 22, 2010.
Troutt et al., Ligation-anchored PCR: a simple amplification technique with single-sided specificity. Proc Natl Acad Sci U S A. Oct. 15, 1992;89(20):9823-5. Erratum in: Proc Natl Acad Sci U S A Apr. 15, 1993;90(8):3775.
Tung et al., Preparation and applications of peptide-oligonucleotide conjugates. Bioconjug Chem. Sep.-Oct. 2000;11(5):605-18.
Van De Goor, Nanopore Detection: Threading DNA Through a Tiny Hole. PharmaGenomics, vol. 4 (3):28-30 (2004).
Van Lengerich et al., Covalent attachment of lipid vesicles to a fluid-supported bilayer allows observation of DNA-mediated vesicle interactions. Langmuir. Jun. 1, 2010;26(11):8666-72. doi: 10.1021/la904822f.

(56) References Cited

OTHER PUBLICATIONS

Venkatesan et al., Nanopore sensors for nucleic acid analysis. Nat Nanotechnol. Sep. 18, 2011;6(10):615-24. doi: 10.1038/nnano.2011.129.
Walker et al., Key residues for membrane binding, oligomerization, and pore forming activity of staphylococcal alpha-hemolysin identified by cysteine scanning mutagenesis and targeted chemical modification. J Biol Chem. Sep. 29, 1995;270(39):23065-71.
Wang et al., Bioconjugation by copper(I)-catalyzed azide-alkyne [3 + 2] cycloaddition. J Am Chem Soc. Mar. 19, 2003;125(11):3192-3.
Wang et al., Nanopores with a spark for single-molecule detection. Nat Biotechnol. Jul. 2001;19(7):622-3.
Wanunu et al., Discrimination of methylcytosine from hydroxymethylcytosine in DNA molecules. J Am Chem Soc. Jan. 26, 2011;133(3):486-92. doi:10.1021/jal07836t. Epub Dec. 14, 2010.
Wanunu et al., DNA translocation governed by interactions with solid-state nanopores. Biophys J. Nov. 15, 2008;95(10):4716-25. doi: 10.1529/biophysj.108.140475. Epub Aug. 15, 2008.
Wemmer et al., Preparation and melting of single strand circular DNA loops. Nucleic Acids Res. Dec. 9, 1985;13(23):8611-21.
Winters-Hilt et al., Highly accurate classification of Watson-Crick basepairs on termini of single DNA molecules. Biophys J. Feb. 2003;84(2 Pt 1):967-76.
Wolfe et al., Catalyzing the translocation of polypeptides through attractive interactions. J Am Chem Soc. Nov. 14, 2007;129(45):14034-41. Epub Oct. 19, 2007.
Wong et al., Polymer capture by electro-osmotic flow of oppositely charged nanopores. J Chem Phys. Apr. 28, 2007;126(16):164903.
Wu et al., Protein nanopores with covalently attached molecular adapters. J Am Chem Soc. Dec. 26, 2007;129(51):16142-8. Epub Nov. 30, 2007.
Xie et al., Single-molecule observation of the catalytic subunit of cAMP-dependent protein kinase binding to an inhibitor peptide. Chem Biol. Jan. 2005;12(1):109-20.
Yamagata et al., Overexpression, purification and characterization of RecJ protein from Thermus thermophilus HB8 and its core domain. Nucleic Acids Res. Nov. 15, 2001;29(22):4617-24.
Lu et al., Structural basis of *Escherichia coli* single-stranded DNA-binding protein stimulation of exonuclease I. Proc Natl Acad Sci U S A. Jul. 8, 2008;105(27):9169-74. doi: 10.1073/pnas.0800741105. Epub Jun. 30, 2008.
Hobbs et al., SSB protein limits RecOR binding onto single-stranded DNA. J Biol Chem. Apr. 13, 2007;282(15):11058-67. Epub Feb. 1, 2007.
Kozlov et al., Regulation of Single-stranded DNA Binding by the C Termini of *Esherichia coli* Single-stranded DNA-binding (SBB) Protein. J. Biol. Chem. May 28, 2010;285(22):17246-52.
Lu et al., Peptide inhibitors identify roles for SSB C-terminal residues in SSB/Exonuclease I complex formation. Biochemistry. Jul. 28, 2009; 48(29): 6764-6771. doi: 10.1021/bi900361r. Author Manuscript.
North et al., Host factors that promote transpososome disassembly and the PriA-PriC pathway for restart primosome assembly. Mol Microbiol. Jun. 2005;56(6):1601-16.
Smith et al., Capture, Unfolding, and Detection of Individual tRNA Molecules Using a Nanopore Device. Front Bioeng Biotechnol. Jun. 24, 2015;3:91. doi: 10.3389/fbioe.2015.00091.
U.S. Appl. No. 16/655,907, filed Oct. 17, 2019, Stoddart et al.
U.S. Appl. No. 16/782,350, filed Feb. 5, 2020, Brown et al.
U.S. Appl. No. 16/743,148, filed Jan. 15, 2020, White.
Cheng, et al., Functional characterization of the multidomain F plasmid TraI relaxase-helicase. J Biol Chem. Apr. 8, 2011;286(14):12670-82. doi: 10.1074/jbc.M110.207563. Epub Feb. 2, 2011.
Colas et al., Microscopical investigations of nisin-loaded nanoliposomes prepared by Mozafari method and their bacterial targeting. Micron. 2007;38(8):841-7. Epub Jul. 3, 2007.

Fairman-Williams et al., SF1 and SF2 helicases: family matters. Curr Opin Struct Biol. Jun. 2010;20(3):313-24. doi: 10.1016/j.sbi.2010.03.011. Epub Apr. 22, 2010.
Gacillàn-Barcia et al., The diversity of conjugative relaxases and its application in plasmid classification. FEMS Microbiol Rev. May 2009;33(3):657-87.
Hammerstein et al., Subunit dimers of alpha-hemolysin expand the engineering toolbox for protein nanopores. J Biol Chem. Apr. 22, 2011;286(16):14324-34. doi: 10.1074/jbc.M111.218164. Epub Feb. 15, 2011.
He et al., The T4 Phage SF1B Helicase Dda is Structurally Optimized to Perform DNA Strand Separation. Structure. Jul. 3, 2012; 20(7): 1189-1200. EPub May 31, 2012. doi: 10.1016/j.str.2012.04.013.
Heron et al., Simultaneous measurement of ionic current and fluorescence from single protein pores. J Am Chem Soc. Feb. 11, 2009;131(5):1652-3. doi: 10.1021/ja808128s.
Ivanov et al., DNA tunneling detector embedded in a nanopore. Nano Lett. Jan. 12, 2011;11(1):279-85. doi: 10.1021/nl103873a. Epub Dec. 6, 2010.
Kozarewa et al., 96-plex molecular barcoding for the Illumina Genome Analyzer. Methods Mol Biol. 2011;733:279-98. doi: 10.1007/978-1-61779-089-8_20.
Kumar et al., Nonradioactive labeling of synthetic oligonucleotide probes with terminal deoxynucleotidyl transferase. Anal Biochem. Mar. 1988;169(2):376-82. Erratum in: Anal Biochem Sep. 1988;173(2):469.
Lee et al., Importance of the conserved CA dinucleotide at Mu termini. J Mol Biol. Nov. 30, 2001;314(3):433-44.
Liu et al., Adding new chemistries to the genetic code. Annu Rev Biochem. 2010;79:413-44. doi: 10.1146/annurev.biochem.052308.105824.
Liu et al., Structure of the DNA repair helicase XPD. Cell. May 30, 2008; 133(5):801-12. doi: 10.1016/j.cell.2008.04.029.
Lohman et al., Non-hexameric DNA helicases and translocases: mechanisms and regulation. Nat Rev Mol Cell Biol. May 2008;9(5):391-401. doi: 10.1038/nrm2394.
Ma et al., Bright functional rotaxanes. Chem Soc Rev. Jan. 2010;39(1):70-80. doi: 10.1039/b901710k. Epub Jul. 21, 2009.
Miner et al., Molecular barcodes detect redundancy and contamination in hairpin-bisulfite PCR. Nucleic Acids Res. 2004; 32(17): e135. EPub Sep. 30, 2004. doi: 10.1093/nar/gnhl32.
O'Shea et al., X-ray structure of the GCN4 leucine zipper, a two-stranded, parallel coiled coil. Science. Oct. 25, 1991;254(5031):539-44.
Pfeiffer et al., Bivalent cholesterol-based coupling of oligonucletides to lipid membrane assemblies. J Am Chem Soc. Aug. 25, 2004;126(33):10224-5.
Remaut et al., Protein-protein interaction through beta-strand addition. Trends Biochem Sci. Aug. 2006;31(8):436-44. Epub Jul. 7, 2006.
Saariaho et al., Characteristics of MuA transposase-catalyzed processing of model transposon end DNA hairpin substrates. Nucleic Acids Res. Jun. 6, 2006;34(10):3139-49. Print 2006.
Satapathy et al., ATPase activity of RecD is essential for growth of the Antarctic Pseudomonas syringae Lz4W at low temperature. FEBS J. Apr. 2008;275(8):1835-51. doi: 10.1111/j.1742-4658.2008.06342.x. Epub Mar. 9, 2008.
Soni et al., Synchronous optical and electrical detection of biomolecules traversing through solid-state nanopores. Rev Sci Instrum. Jan. 2010;81(1):014301. doi: 10.1063/1.3277116.
Tuteja et al., Unraveling DNA helicases. Motif, structure, mechanism and function. Eur J Biochem. May 2004;271(10):1849-63. Review. Erratum in: Eur J Biochem. Aug. 2004;271(15):3283.
Van Heel et al., Single-particle electron cryo-microscopy: towards atomic resolution. Q Rev Biophys. Nov. 2000;33(4):307-69.
Woodman et al., Archaeal Hel308 domain V couples DNA binding to ATP hydrolysis and positions DNA for unwinding over the helicase ratchet. J Mol Biol. Dec. 14, 2007;374(5):1139-44. Epub Oct. 10, 2007.
Yoshina-Ishii et al., Arrays of mobile tethered vesicles on supported lipid bilayers. J Am Chem Soc. Apr. 2, 2003;125(13):3696-7.
Yusko et al., Controlling the translocation of proteins through nanopores with bioinspired fluid walls. Nat Nanotechnol. Apr. 2011; 6(4): 253-260. EPub Feb. 20, 2011. doi: 10.1038/nnano.2011.12.
U.S. Appl. No. 16/855,096, filed Apr. 22, 2020, Clarke et al.

(56) References Cited

OTHER PUBLICATIONS

U.S. Appl. No. 16/363,444, filed Apr. 24, 2020, First Action Interview Pilot Program Pre-Interview Communication.
U.S. Appl. No. 16/363,444, filed Jun. 9, 2020, First Action Interview Office Action Summary.
U.S. Appl. No. 16/568,781, filed Jan. 7, 2020, Pre-Interview First Office Action.
U.S. Appl. No. 16/568,781, filed Apr. 8, 2020, Examiner Initiated Interview Summary.
U.S. Appl. No. 16/568,781, filed Jun. 8, 2020, Final Rejection.
U.S. Appl. No. 16/568,781, filed Aug. 27, 2020, Final Rejection.
Chin et al., The origin of the Haitian cholera outbreak strain. N Engl J Med. Jan. 6, 2011;364(1):33-42 and Supplemental Material, doi: 10.1056/NEJMoa1012928. Epub Dec. 9, 2010. Author Manuscript. 304 pages.
Declaration of Stephen Turner, Ph.D., filed in U.S. Appl. No. 15/089,071, filed Sep. 15, 2016. 5 pages.
Dong et al., Amplified detection of nucleic acid by G-quadruplex based hybridization chain reaction. Biosens Bioelectron. Oct.-Dec. 2012;38(1):258-63. doi: 10.1016/j.bios.2012.05.042. Epub Jun. 8, 2012.
Faller et al., The structure of a mycobacterial outer-membrane channel. Science. Feb. 20, 2004;303(5661):1189-92. doi: 10.1126/science.1094114.
Gill et al., Nucleic acid isothermal amplification technologies: a review. Nucleosides Nucleotides Nucleic Acids. Mar. 2008;27(3):224-43. doi: 10.1080/15257770701845204.
He et al., The carboxyl-terminal domain of bacteriophage T7 single-stranded DNA-binding protein modulates DNA binding and interaction with T7 DNA polymerase. J Biol Chem. Aug. 8, 2003;278(32):29538-45. doi: 10.1074/jbc.M304318200. Epub May 24, 2003.
Hollis et al., Structure of the gene 2.5 protein, a single-stranded DNA binding protein encoded by bacteriophage T7. Proc Natl Acad Sci U S A. Aug. 14, 2001;98(17):9557-62. doi: 10.1073/pnas.171317698. Epub Jul. 31, 2001.
Hyland et al., The DNA binding domain of the gene 2.5 single-stranded DNA-binding protein of bacteriophage T7. J Biol Chem. Feb. 28, 2003;278(9):7247-56. doi: 10.1074/jbc.M210605200. Epub Dec. 20, 2002.
Kuipers, Random mutagenesis by using mixtures of dNTP and dITP in PCR. Methods Mol Biol. 1996;57:351-6. doi: 10.1385/0-89603-332-5:351.
Liang, Structure of outer membrane protein G by solution NMR spectroscopy. Proc Natl Acad Sci U S A. Oct. 9, 2007;104(41):16140-5. doi: 10.1073/pnas.0705466104. Epub Oct. 2, 2007.
Locher et al., Transmembrane signaling across the ligand-gated FhuA receptor: crystal structures of free and ferrichrome-bound states reveal allosteric changes. Cell. Dec. 11, 1998;95(6):771-8. doi: 10.1016/s0092-8674(00)81700-6.
Loomis et al., Sequencing the unsequenceable: expanded CGG-repeat alleles of the fragile X gene. Genome Res. Jan. 2013;23(1):121-8. doi: 10.1101/gr.141705.112. Epub Oct. 11, 2012.
Pettersson et al., Generations of sequencing technologies. Genomics. Feb. 2009;93(2):105-11. doi: 10.1016/j.ygeno.2008.10.003. Epub Nov. 21, 2008.
Quail et al., A tale of three next generation sequencing platforms: comparison of Ion Torrent, Pacific Biosciences and Illumina MiSeq sequencers. BMC Genomics. Jul. 24, 2012;13:341. doi: 10.1186/1471-2164-13-341.
Rezende et al., Essential amino acid residues in the single-stranded DNA-binding protein of bacteriophage T7. Identification of the dimer interface. J Biol Chem. Dec. 27, 2002;277(52):50643-53. doi: 10.1074/jbc.M207359200. Epub Oct. 12, 2002.
Rhoads et al., PacBio Sequencing and Its Applications. Genomics Proteomics Bioinformatics. Oct. 2015;13(5):278-89. doi: 10.1016/j.gpb.2015.08.002. Epub Nov. 2, 2015.
Shendure et al., Overview of DNA sequencing strategies. Curr Protoc Mol Biol. Jan. 2008;Chapter 7:Unit 7.1. doi: 10.1002/0471142727.mb0701s81.
Spee et al., Efficient random mutagenesis method with adjustable mutation frequency by use of PCR and dITP. Nucleic Acids Res. Feb. 11, 1993;21(3):777-8. doi: 10.1093/nar/21.3.777.
Thompson et al., The properties and applications of single-molecule DNA sequencing. Genome Biol. 2011;12(2):217. doi: 10.1186/GB-2011-12-2-217. Epub Feb. 24, 2011.
Tucker et al., Massively parallel sequencing: the next big thing in genetic medicine. Am J Hum Genet. Aug. 2009;85(2):142-54. doi: 10.1016/j.ajhg.2009.06.022.
Wang et al., A simple and reproducible method for directed evolution: combination of random mutation with dITP and DNA fragmentation with endonuclease V. Mol Biotechnol. Jan. 2013;53(1):49-54. doi: 10.1007/s12033-012-9516-9.
Yamashita et al., Crystal structures of the OmpF porin: function in a colicin translocon. EMBO J. Aug. 6, 2008;27(15):2171-80. doi: 10.1038/emboj.2008.137. Epub Jul. 17, 2008.

\* cited by examiner

SEQUENCE LISTING

<160> NUMBER OF SEQ ID NOS: 22

<210> SEQ ID NO 1
<211> LENGTH: 882
<212> TYPE: DNA

-continued

<213> ORGANISM: Staphylococcus aureus

<400> SEQUENCE: 1

```
atggcagatt ctgatattaa tattaaaacc ggtactacag atattggaag caatactaca    60
gtaaaaacag gtgatttagt cacttatgat aaagaaaatg gcatgcacaa aaaagtattt   120
tatagtttta tcgatgataa aaatcacaat aaaaaactgc tagttattag aacaaaaggt   180
accattgctg gtcaatatag agtttatagc gaagaaggtg ctaacaaaag tggtttagcc   240
tggccttcag cctttaaggt acagttgcaa ctacctgata tgaagtagc  tcaaatatct   300
gattactatc caagaaattc gattgataca aaagagtata tgagtacttt aacttatgga   360
ttcaacggta atgttactgg tgatgataca ggaaaaattg gcggcttat  tggtgcaaat   420
gtttcgattg gtcatacact gaaatatgtt caacctgatt tcaaaacaat tttagagagc   480
ccaactgata aaaagtagg  ctggaaagtg atatttaaca atatggtgaa tcaaaattgg   540
ggaccatacg atcgagattc ttggaacccg gtatatggca atcaacttt  catgaaaact   600
agaaatggtt ctatgaaagc agcagataac ttccttgatc ctaacaaagc aagttctcta   660
ttatcttcag gttttcacc  agacttcgct acagttatta ctatggatag aaaagcatcc   720
aaacaacaaa caaatataga tgtaaatatac gaacgagttc gtgatgatta ccaattgcat   780
tggacttcaa caaattggaa aggtaccaat actaaagata atggacaga  tcgttcttca   840
gaaagatata aaatcgattg ggaaaaagaa gaaatgacaa at                      882
```

<210> SEQ ID NO 2
<211> LENGTH: 293
<212> TYPE: PRT
<213> ORGANISM: Staphylococcus aureus

<400> SEQUENCE: 2

```
Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
```

```
                195                 200                 205
Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290

<210> SEQ ID NO 3
<211> LENGTH: 882
<212> TYPE: DNA
<213> ORGANISM: Artificial Sequence
<220> FEATURE:
<223> OTHER INFORMATION: Synthetic polynucleotide

<400> SEQUENCE: 3
atggcagatt ctgatattaa tattaaaacc ggtactacag atattggaag caatactaca    60
gtaaaaacag gtgatttagt cacttatgat aaagaaatg gcatgcacaa aaagtatt    120
tatagtttta tcgatgataa aaatcacaat aaaaaactgc tagttattag aacaaaaggt    180
accattgctg gtcaatatag agtttatagc gaagaaggtg ctaacaaaag tggtttagcc    240
tggccttcag cctttaaggt acagttgcaa ctacctgata tgaagtagc tcaaatatct    300
gattactatc caagaaattc gattgataca aaagagtata ggagtacttt aacttatgga    360
ttcaacggta atgttactgg tgatgataca ggaaaaattg gcggccttat tggtgcacaa    420
gtttcgattg tcatacact gaaatatgtt caacctgatt tcaaaacaat tttagagagc    480
ccaactgata aaaagtagg ctggaaagtg atatttaaca atatggtgaa tcaaaattgg    540
ggaccatacg atcgagattc ttggaacccg tatatggca atcaactttt catgaaaact    600
agaaatggtt ctatgaaagc agcagataac ttccttgatc taacaaagc aagttctcta    660
ttatcttcag ggttttcacc agacttcgct acagttatta ctatggatag aaaagcatcc    720
aaacaacaaa caaatataga tgtaatatac gaacgagttc gtgatgatta ccaattgcat    780
tggacttcaa caaattggaa aggtaccaat actaaagata atggacaga tcgttcttca    840
gaaagatata aaatcgattg ggaaaaagaa gaaatgacaa at                      882

<210> SEQ ID NO 4
<211> LENGTH: 293
<212> TYPE: PRT
<213> ORGANISM: Artificial Sequence
<220> FEATURE:
<223> OTHER INFORMATION: Synthetic polypeptide

<400> SEQUENCE: 4

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45
```

Asn Lys Lys Leu Leu Val Ile Arg Thr Lys Gly Thr Ile Ala Gly Gln
 50                  55                  60

Tyr Arg Val Tyr Ser Glu Glu Gly Ala Asn Lys Ser Gly Leu Ala Trp
 65                  70                  75                  80

Pro Ser Ala Phe Lys Val Gln Leu Gln Leu Pro Asp Asn Glu Val Ala
                 85                  90                  95

Gln Ile Ser Asp Tyr Tyr Pro Arg Asn Ser Ile Asp Thr Lys Glu Tyr
            100                 105                 110

Arg Ser Thr Leu Thr Tyr Gly Phe Asn Gly Asn Val Thr Gly Asp Asp
        115                 120                 125

Thr Gly Lys Ile Gly Gly Leu Ile Gly Ala Gln Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290

<210> SEQ ID NO 5
<211> LENGTH: 1425
<212> TYPE: DNA
<213> ORGANISM: E. coli

<400> SEQUENCE: 5

```
atgatgaatg acggtaagca acaatctacc ttttttgtttc acgattacga aacctttggc     60
acgcacccccg cgttagatcg ccctgcacag ttcgcagcca ttcgcaccga tagcgaattc    120
aatgtcatcg gcgaacccga agtcttttac tgcaagcccg ctgatgacta tttaccccag    180
ccaggagccg tattaattac cggtattacc ccgcaggaag cacgggcgaa aggagaaaac    240
gaagccgcgt ttgccgcccg tattcactcg cttttttaccg taccgaagac ctgtattctg    300
ggctacaaca atgtgcgttt cgacgacgaa gtcacacgca acatttttta tcgtaatttc    360
tacgatcctt acgcctggag ctggcagcat gataactcgc gctgggattt actggatgtt    420
atgcgtgcct gttatgccct cgcccccggaa ggaataaact ggcctgaaaa tgatgacggt    480
ctaccgagct ttcgccttga gcatttaacc aaagcgaatg gtattgaaca tagcaacgcc    540
cacgatgcga tggctgatgt gtacgccact attgcgatgg caaagctggt aaaaacgcgt    600
cagccacgcc tgtttgatta tctctcttacc catcgtaata aacacaaaact gatggcgttg    660
attgatgttc cgcagatgaa acccctggtg cacgtttccg gaatgtttgg agcatggcgc    720
```

```
ggcaatacca gctgggtggc accgctggcg tggcatcctg aaaatcgcaa tgccgtaatt    780
atggtggatt tggcaggaga catttcgcca ttactggaac tggatagcga cacattgcgc    840
gagcgtttat ataccgcaaa aaccgatctt ggcgataacg ccgccgttcc ggttaagctg    900
gtgcatatca ataaatgtcc ggtgctggcc caggcgaata cgctacgccc ggaagatgcc    960
gaccgactgg gaattaatcg tcagcattgc ctcgataacc tgaaaattct gcgtgaaaat   1020
ccgcaagtgc gcgaaaaagt ggtggcgata ttcgcggaag ccgaaccgtt tacgccttca   1080
gataacgtgg atgcacagct ttataacggc ttttcagtg acgcagatcg tgcagcaatg    1140
aaaattgtgc tggaaaccga ccgcgtaat ttaccggcac tggatatcac ttttgttgat    1200
aaacggattg aaaagctgtt gttcaattat cgggcacgca acttcccggg gacgctggat   1260
tatgccgagc agcaacgctg gctggagcac cgtcgccagg tcttcacgcc agagttttg    1320 cagggttatg ctgatgaatt gcagatgctg gtacaacaat atgccgatga caaagagaaa   1380
gtggcgctgt aaaagcact ttggcagtac gcggaagaga ttgtc                    1425
```

<210> SEQ ID NO 6
<211> LENGTH: 475
<212> TYPE: PRT
<213> ORGANISM: E. coli

<400> SEQUENCE: 6

```
Met Met Asn Asp Gly Lys Gln Gln Ser Thr Phe Leu Phe His Asp Tyr
1               5                   10                  15

Glu Thr Phe Gly Thr His Pro Ala Leu Asp Arg Pro Ala Gln Phe Ala
            20                  25                  30

Ala Ile Arg Thr Asp Ser Glu Phe Asn Val Ile Gly Glu Pro Glu Val
        35                  40                  45

Phe Tyr Cys Lys Pro Ala Asp Asp Tyr Leu Pro Gln Pro Gly Ala Val
    50                  55                  60

Leu Ile Thr Gly Ile Thr Pro Gln Glu Ala Arg Ala Lys Gly Glu Asn
65                  70                  75                  80

Glu Ala Ala Phe Ala Ala Arg Ile His Ser Leu Phe Thr Val Pro Lys
                85                  90                  95

Thr Cys Ile Leu Gly Tyr Asn Asn Val Arg Phe Asp Asp Glu Val Thr
            100                 105                 110

Arg Asn Ile Phe Tyr Arg Asn Phe Tyr Asp Pro Tyr Ala Trp Ser Trp
        115                 120                 125

Gln His Asp Asn Ser Arg Trp Asp Leu Leu Asp Val Met Arg Ala Cys
    130                 135                 140

Tyr Ala Leu Arg Pro Glu Gly Ile Asn Trp Pro Glu Asn Asp Asp Gly
145                 150                 155                 160

Leu Pro Ser Phe Arg Leu Glu His Leu Thr Lys Ala Asn Gly Ile Glu
                165                 170                 175

His Ser Asn Ala His Asp Ala Met Ala Asp Val Tyr Ala Thr Ile Ala
            180                 185                 190

Met Ala Lys Leu Val Lys Thr Arg Gln Pro Arg Leu Phe Asp Tyr Leu
        195                 200                 205

Phe Thr His Arg Asn Lys His Lys Leu Met Ala Leu Ile Asp Val Pro
    210                 215                 220

Gln Met Lys Pro Leu Val His Val Ser Gly Met Phe Gly Ala Trp Arg
225                 230                 235                 240

Gly Asn Thr Ser Trp Val Ala Pro Leu Ala Trp His Pro Glu Asn Arg
```

```
                      245                 250                 255
Asn Ala Val Ile Met Val Asp Leu Ala Gly Asp Ile Ser Pro Leu Leu
                260                 265                 270

Glu Leu Asp Ser Asp Thr Leu Arg Glu Arg Leu Tyr Thr Ala Lys Thr
            275                 280                 285

Asp Leu Gly Asp Asn Ala Ala Val Pro Val Lys Leu Val His Ile Asn
        290                 295                 300

Lys Cys Pro Val Leu Ala Gln Ala Asn Thr Leu Arg Pro Glu Asp Ala
305                 310                 315                 320

Asp Arg Leu Gly Ile Asn Arg Gln His Cys Leu Asp Asn Leu Lys Ile
                325                 330                 335

Leu Arg Glu Asn Pro Gln Val Arg Glu Lys Val Val Ala Ile Phe Ala
            340                 345                 350

Glu Ala Glu Pro Phe Thr Pro Ser Asp Asn Val Asp Ala Gln Leu Tyr
        355                 360                 365

Asn Gly Phe Phe Ser Asp Ala Asp Arg Ala Ala Met Lys Ile Val Leu
    370                 375                 380

Glu Thr Glu Pro Arg Asn Leu Pro Ala Leu Asp Ile Thr Phe Val Asp
385                 390                 395                 400

Lys Arg Ile Glu Lys Leu Leu Phe Asn Tyr Arg Ala Arg Asn Phe Pro
                405                 410                 415

Gly Thr Leu Asp Tyr Ala Glu Gln Gln Arg Trp Leu Glu His Arg Arg
            420                 425                 430

Gln Val Phe Thr Pro Glu Phe Leu Gln Gly Tyr Ala Asp Glu Leu Gln
        435                 440                 445

Met Leu Val Gln Gln Tyr Ala Asp Asp Lys Glu Lys Val Ala Leu Leu
    450                 455                 460

Lys Ala Leu Trp Gln Tyr Ala Glu Glu Ile Val
465                 470                 475

<210> SEQ ID NO 7
<211> LENGTH: 1275
<212> TYPE: DNA
<213> ORGANISM: T. thermophilus

<400> SEQUENCE: 7
atgtttcgtc gtaaagaaga tctggatccg ccgctggcac tgctgccgct gaaaggcctg      60
cgcgaagccg ccgcactgct ggaagaagcg ctgcgtcaag gtaaacgcat cgtgttcac     120 ggcgactatg atgcggatgg cctgaccggc accgcgatcc tggttcgtgg tctggccgcc    180
ctgggtgcgg atgttcatcc gtttatcccg caccgcctgg aagaaggcta tggtgtcctg    240
atggaacgcg tcccggaaca tctggaagcc tcggacctgt ttctgaccgt tgactgcggc    300
attaccaacc atgcggaact gcgcgaactg ctggaaaatg gcgtggaagt cattgttacc    360
gatcatcata cgccgggcaa aacgccgccg ccgggtctgg tcgtgcatcc ggcgctgacg    420
ccggatctga agaaaaaacc gaccggcgca ggcgtggcgt ttctgctgct gtgggcactg    480
catgaacgcc tgggcctgcc gccgccgctg aatacgcgg acctggcagc cgttggcacc    540
attgccgacg ttgccccgct gtggggttgg aatcgtgcac tggtgaaaga aggtctggca    600
cgcatcccgg cttcatcttg ggtgggcctg cgtctgctgg ctgaagccgt gggctatacc    660
ggcaaagcgg tcgaagtcgc tttccgcatc gcgccgcgca tcaatgcggc ttcccgcctg    720 ggcgaagcg aaaaagccct gcgcctgctg ctgacggatg atgcggcaga agctcaggcg    780
ctggtcggcg aactgcaccg tctgaacgcc cgtcgtcaga ccctggaaga agcgatgctg    840
```

-continued

```
cgcaaactgc tgccgcaggc cgacccggaa gcgaaagcca tcgttctgct ggacccggaa      900
ggccatccgg gtgttatggg tattgtggcc tctcgcatcc tggaagcgac cctgcgcccg      960
gtctttctgg tggcccaggg caaaggcacc gtgcgttcgc tggctccgat tccgccgtc     1020 gaagcactgc gcagcgcgga agatctgctg ctgcgttatg gtggtcataa agaagcggcg     1080
ggtttcgcaa tggatgaagc gctgtttccg gcgttcaaag cacgcgttga agcgtatgcc     1140
gcacgtttcc cggatccggt tcgtgaagtg cactgctgg atctgctgcc ggaaccgggc     1200
ctgctgccgc aggtgttccg tgaactggca ctgctggaac cgtatggtga aggtaacccg     1260
gaaccgctgt cctg                                                     1275
```

<210> SEQ ID NO 8
<211> LENGTH: 425
<212> TYPE: PRT
<213> ORGANISM: T. thermophilus

<400> SEQUENCE: 8

```
Met Phe Arg Arg Lys Glu Asp Leu Asp Pro Pro Leu Ala Leu Leu Pro
1               5                  10                  15

Leu Lys Gly Leu Arg Glu Ala Ala Ala Leu Leu Glu Glu Ala Leu Arg
            20                  25                  30

Gln Gly Lys Arg Ile Arg Val His Gly Asp Tyr Asp Ala Asp Gly Leu
        35                  40                  45

Thr Gly Thr Ala Ile Leu Val Arg Gly Leu Ala Ala Leu Gly Ala Asp
    50                  55                  60

Val His Pro Phe Ile Pro His Arg Leu Glu Glu Gly Tyr Gly Val Leu
65                  70                  75                  80

Met Glu Arg Val Pro Glu His Leu Glu Ala Ser Asp Leu Phe Leu Thr
                85                  90                  95

Val Asp Cys Gly Ile Thr Asn His Ala Glu Leu Arg Glu Leu Leu Glu
            100                 105                 110

Asn Gly Val Glu Val Ile Val Thr Asp His His Thr Pro Gly Lys Thr
        115                 120                 125

Pro Pro Pro Gly Leu Val Val His Pro Ala Leu Thr Pro Asp Leu Lys
    130                 135                 140

Glu Lys Pro Thr Gly Ala Gly Val Ala Phe Leu Leu Leu Trp Ala Leu
145                 150                 155                 160

His Glu Arg Leu Gly Leu Pro Pro Leu Glu Tyr Ala Asp Leu Ala
                165                 170                 175

Ala Val Gly Thr Ile Ala Asp Val Ala Pro Leu Trp Gly Trp Asn Arg
            180                 185                 190

Ala Leu Val Lys Glu Gly Leu Ala Arg Ile Pro Ala Ser Ser Trp Val
        195                 200                 205

Gly Leu Arg Leu Leu Ala Glu Ala Val Gly Tyr Thr Gly Lys Ala Val
    210                 215                 220

Glu Val Ala Phe Arg Ile Ala Pro Arg Ile Asn Ala Ala Ser Arg Leu
225                 230                 235                 240

Gly Glu Ala Glu Lys Ala Leu Arg Leu Leu Thr Asp Asp Ala Ala
                245                 250                 255

Glu Ala Gln Ala Leu Val Gly Glu Leu His Arg Leu Asn Ala Arg Arg
            260                 265                 270

Gln Thr Leu Glu Glu Ala Met Leu Arg Lys Leu Leu Pro Gln Ala Asp
        275                 280                 285
```

```
Pro Glu Ala Lys Ala Ile Val Leu Leu Asp Pro Glu Gly His Pro Gly
    290                 295                 300

Val Met Gly Ile Val Ala Ser Arg Ile Leu Glu Ala Thr Leu Arg Pro
305                 310                 315                 320

Val Phe Leu Val Ala Gln Gly Lys Gly Thr Val Arg Ser Leu Ala Pro
                325                 330                 335

Ile Ser Ala Val Glu Ala Leu Arg Ser Ala Glu Asp Leu Leu Leu Arg
            340                 345                 350

Tyr Gly Gly His Lys Glu Ala Ala Gly Phe Ala Met Asp Glu Ala Leu
        355                 360                 365

Phe Pro Ala Phe Lys Ala Arg Val Glu Ala Tyr Ala Ala Arg Phe Pro
    370                 375                 380

Asp Pro Val Arg Glu Val Ala Leu Leu Asp Leu Leu Pro Glu Pro Gly
385                 390                 395                 400

Leu Leu Pro Gln Val Phe Arg Glu Leu Ala Leu Leu Glu Pro Tyr Gly
                405                 410                 415

Glu Gly Asn Pro Glu Pro Leu Phe Leu
            420                 425

<210> SEQ ID NO 9
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 9
tagggataac agggtaat                                                    18

<210> SEQ ID NO 10
<211> LENGTH: 67
<212> TYPE: DNA
<213> ORGANISM: Artificial Sequence
<220> FEATURE:
<223> OTHER INFORMATION: Synthetic polynucleotide

<400> SEQUENCE: 10
tgtgttctat gtcttattct tacttcgtta ttcttgtctc tattctgttt atgtttcttg      60
tttgtta                                                                67

<210> SEQ ID NO 11
<211> LENGTH: 17
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (17)..(17)
<223> OTHER INFORMATION: linked to -(CH2)4-maleimide

<400> SEQUENCE: 11
tgtgttctat gtctttt                                                     17

<210> SEQ ID NO 12
<211> LENGTH: 27
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (27)..(27)
```

<223> OTHER INFORMATION: linked to -(CH2)4-maleimide

<400> SEQUENCE: 12
tgtgttctat gtcttattct tactttt                                    27

<210> SEQ ID NO 13
<211> LENGTH: 37
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (37)..(37)
<223> OTHER INFORMATION: linked to -(CH2)4-maleimide

<400> SEQUENCE: 13
tgtgttctat gtcttattct tacttcgtta ttctttt                         37

<210> SEQ ID NO 14
<211> LENGTH: 17
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (17)..(17)
<223> OTHER INFORMATION: linked to -(CH2)4-maleimide

<400> SEQUENCE: 14
aagacataga acacatt                                               17

<210> SEQ ID NO 15
<211> LENGTH: 27
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (27)..(27)
<223> OTHER INFORMATION: linked to -(CH2)4-maleimide

<400> SEQUENCE: 15
aagtaagaat aagacataga acacatt                                    27

<210> SEQ ID NO 16
<211> LENGTH: 37
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (37)..(37)
<223> OTHER INFORMATION: linked to -(CH2)4-maleimide

<400> SEQUENCE: 16
aagaataacg aagtaagaat aagacataga acacatt                         37

<210> SEQ ID NO 17
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 17

```
attaccctgt tatccctc                                                    18
```

<210> SEQ ID NO 18
<211> LENGTH: 3
<212> TYPE: PRT
<213> ORGANISM: Artificial Sequence
<220> FEATURE:
<223> OTHER INFORMATION: Synthetic Polypeptide

<400> SEQUENCE: 18

Gly Ala Pro
1

<210> SEQ ID NO 19
<211> LENGTH: 3
<212> TYPE: PRT
<213> ORGANISM: Artificial Sequence
<220> FEATURE:
<223> OTHER INFORMATION: Synthetic Polypeptide

<400> SEQUENCE: 19

Ile Leu Val
1

<210> SEQ ID NO 20
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 20

Cys Ser Thr Met
1

<210> SEQ ID NO 21
<211> LENGTH: 3
<212> TYPE: PRT
<213> ORGANISM: Artificial Sequence
<220> FEATURE:
<223> OTHER INFORMATION: Synthetic Polypeptide

<400> SEQUENCE: 21

His Lys Arg
1

<210> SEQ ID NO 22
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 22

His Phe Trp Tyr
1

ADAPTORS FOR NUCLEIC ACID CONSTRUCTS IN TRANSMEMBRANE SEQUENCING

RELATED APPLICATIONS

This Application is a continuation of U.S. application Ser. No. 15/390,806, filed on Dec. 27, 2016, now abandoned, which is a continuation of U.S. application Ser. No. 13/147, 159, filed on Nov. 15, 2011, now abandoned, which is a national stage filing under U.S.C. § 371 of PCT International Application No. PCT/GB2010/000160, which has an international filing date of Jan. 29, 2010, and claims the benefit under 35 U.S.C. § 119(e) of U.S. Provisional Application Ser. No. 61/148,737, filed on Jan. 30, 2009, the contents of each of which are incorporated herein by reference in their entireties.

FIELD OF THE INVENTION

The invention relates to adaptors for sequencing nucleic acids. The adaptors may be used to generate single stranded constructs of nucleic acid for sequencing purposes. Such constructs may contain both strands from a double stranded deoxyribonucleic acid (DNA) or ribonucleic acid (RNA) template. The invention also relates to the constructs generated using the adaptors, methods of making the adaptors and constructs, as well as methods of sequencing double stranded nucleic acids.

BACKGROUND OF THE INVENTION

Stochastic detection is an approach to sensing that relies on the observation of individual binding events between analyte molecules and a receptor. Stochastic sensors can be created by placing a single pore of nanometer dimensions in an insulating membrane and measuring voltage-driven ionic transport through the pore in the presence of analyte molecules. The frequency of occurrence of fluctuations in the current reveals the concentration of an analyte that binds within the pore. The identity of an analyte is revealed through its distinctive current signature, notably the duration and extent of current block (Braha, O., Walker, B., Cheley, S., Kasianowicz, J. J., Song, L., Gouaux, J. E., and Bayley, H. (1997) Chem. Biol. 4, 497-505; and Bayley, H., and Cremer, P. S. (2001) Nature 413, 226-230).

Engineered versions of the bacterial pore forming toxin a-hemolysin (a-HL) have been used for stochastic sensing of many classes of molecules (Bayley, H., and Cremer, P. S. (2001) Nature 413, 226-230; Shin, S., H., Luchian, T., Cheley, S., Braha, O., and Bayley, H. (2002) Angew. Chem. Int. Ed. 41, 3707-3709; and Guan, X., Gu, L.-Q., Cheley, S., Braha, O., and Bayley, H. (2005) ChemBioChem 6, 1875-1881). In the course of these studies, it was found that attempts to engineer a-HL to bind small organic analytes directly can prove taxing, with rare examples of success (Guan, X., Gu, L.-Q., Cheley, S., Braha, O., and Bayley, H. (2005) ChemBioChem 6, 1875-1881). Fortunately, a different strategy was discovered, which utilised non-covalently attached molecular adaptors, notably cyclodextrins (Gu, L.-Q., Braha, O., Conlan, S., Cheley, S., and Bayley, H. (1999) Nature 398, 686-690), but also cyclic peptides (Sanchez-Quesada, J., Ghadiri, M. R., Bayley, H., and Braha, O. (2000) J Am. Chem. Soc. 122, 11758-11766) and cucurbiturils (Braha, O., Webb, J., Gu, L.-Q., Kim, K., and Bayley, H. (2005) ChemPhysChem 6, 889-892). Cyclodextrins become transiently lodged in the α-HL pore and produce a substantial but incomplete channel block. Organic analytes, which bind within the hydrophobic interiors of cyclodextrins, augment this block allowing analyte detection (Gu, L.-Q., Braha, O., Conlan, S., Cheley, S., and Bayley, H. (1999) Nature 398, 686-690).

There is currently a need for rapid and cheap DNA or RNA sequencing technologies across a wide range of applications. Existing technologies are slow and expensive mainly because they rely on amplification techniques to produce large volumes of nucleic acid and require a high quantity of specialist fluorescent chemicals for signal detection. Stochastic sensing has the potential to provide rapid and cheap DNA sequencing by reducing the quantity of nucleotide and reagents required.

SUMMARY OF THE INVENTION

The inventor(s) have surprisingly demonstrated that artificial, identifiable adaptors may be used to generate single stranded nucleic acid constructs that contain both strands of a double stranded nucleic acid template. The two strands of the template are covalently linked and delineated (divided) by an adaptor. The adaptor not only allows the transition point from one strand to the other strand to be identified, but also allows the construct to be purified before it is sequenced. The adaptor may further allow the construct to be differentiated from similar constructs in which the strands have a different source. Hence, the adaptors allow multiplex sequence analysis of templates originating from separate individual sources.

The adaptors are particularly useful for sequencing double stranded DNA (dsDNA) and double stranded RNA (dsRNA). The adaptors may be used to generate single stranded constructs containing both the sense and antisense strands of the dsDNA or dsRNA.

The adaptors are generally used in pairs. Both types of adaptor in the pair not only comprise a region of double stranded nucleic acid that forms one half of a palindromic cleavage site, but also are differentially selectable from one another. Each pair comprises two types of adaptor; Type I and Type II. Type I adaptors comprise a hairpin loop, which allows covalent linkage of the two strands in a double stranded nucleic acid template. Type II adaptors may comprise a hairpin loop, but do not have to. This combination of features allows the generation and purification of single stranded constructs in which both strands of a double stranded nucleic acid template are covalently linked via a Type I adaptor. Unwanted constructs formed by ligation of adaptors with each other may be eliminated from the reaction mixture using the palindromic cleavage site. Similarly, constructs containing one or other of the two types of adaptor may be isolated from the reaction mixture using the adaptor's differential selectability.

Accordingly, the invention provides an adaptor for sequencing nucleic acids, which comprises a region of double stranded nucleic acid, wherein at least one end of the region forms one half of a palindromic cleavage site and wherein the adaptor is differentially selectable from another adaptor. In some embodiments, the region is formed by hybridization between two separated regions of a single stranded nucleic acid and the adaptor comprises a hairpin loop.

The invention also provides:

a pair of adaptors comprising an adaptor of the invention formed by hybridization between two separated regions of a single stranded nucleic acid and comprising a hairpin loop (Type I) and an adaptor of the invention (Type II), wherein each type of adaptor in the pair is differentially selectable from the other type and wherein a complete palindromic cleavage site is formed if any combination of the two types of adaptor are ligated to one another;

a kit comprising at least two populations of adaptors of the invention, wherein every adaptor in each population comprises a nucleic acid sequence that is specific for the population;

a nucleic acid construct for use as a sequencing template comprising a double stranded nucleic acid ligated to at least one adaptor of the invention;

a single stranded nucleic acid construct for use as a sequencing template comprising two strands of nucleic acid covalently linked via an adaptor of the invention formed by hybridization between two separated regions of a single stranded nucleic acid and comprising a hairpin loop;

a circular nucleic acid construct for use as a sequencing template comprising two strands of nucleic acid covalently linked at each end via an adaptor of the invention formed by hybridization between two separated regions of a single stranded nucleic acid and comprising a hairpin loop;

a method for preparing an adaptor of the invention, comprising:
  (a) providing two nucleic acids that are (i) capable of hybridizing to one another to form one half of a palindromic cleavage site and (ii) differentially selectable from those of another adaptor; and
  (b) contacting the nucleic acids under conditions which allow them to hybridise and thereby preparing an adaptor;

a method for preparing an adaptor of the invention formed by hybridization between two separated regions of a single stranded nucleic acid and comprising a hairpin loop, comprising:
  (a) providing a single stranded nucleic acid comprising (i) two regions that are capable of hybridizing to one another, (ii) a loop-forming region that is differentially selectable from that of another adaptor and (iii) two ends which together form one half of a palindromic cleavage site; and
  (b) exposing the nucleic acid to conditions which allow the two regions to hybridise and form a hairpin loop and thereby preparing an adaptor;

a method for preparing a nucleic acid construct of the invention, comprising:
  (a) contacting at least one adaptor of the invention with two strands of nucleic acid under conditions which allow ligation between the adaptor(s) and the strands; and
  (b) allowing the adaptor to ligate to the two strands and thereby preparing a nucleic acid construct;

a method for preparing a single stranded nucleic acid construct of the invention, comprising:
  (a) contacting an adaptor of the invention formed by hybridization between two separated regions of a single stranded nucleic acid and comprising a hairpin loop with two strands of nucleic acid under conditions which allow ligation between the adaptor and the strands;
  (b) allowing the adaptor to covalently link the two strands; and
  (c) denaturing the covalently linked construct and thereby preparing a single stranded nucleic acid construct;

a method for preparing a circular nucleic acid construct of the invention, comprising:
  (a) contacting at least two adaptors of the invention which comprise a hairpin loop with two strands of nucleic acid under conditions which allow ligation between the adaptors and strands; and
  (b) allowing an adaptor to covalently link the two strands at each end and thereby preparing a circular nucleic acid construct;

a method for preparing a sequence construct, comprising:
  (a) providing double stranded nucleic acid;
  (b) contacting the double stranded nucleic acid with a pair of adaptors of the invention in which the Type I adaptors are not capable of being cleaved or nicked and the Type II adaptors are capable of being cleaved or nicked under conditions which allow the adaptors to ligate to the nucleic acid;
  (c) contacting the ligated products with a surface that specifically binds the Type II adaptors and removing any unbound products;
  (d) contacting the surface with an enzyme that recognises the complete palindromic cleavage site and removing any unbound products;
  (e) cleaving the Type II adaptors;
  (f) contacting the soluble products produced in step (e) with a surface that specifically binds the Type I adaptors and removing any unbound products; and
  (g) releasing from the surface the products remaining following step (f) and thereby producing a sequencing construct;

a method of sequencing double stranded nucleic acid, comprising:
  (a) carrying out a method of the invention;
  (b) denaturing the construct, if necessary, to form a single stranded construct; and
  (c) sequencing the single stranded construct and thereby sequencing the double stranded nucleic acid; and a kit for sequencing double stranded nucleic acid comprising a pair of adaptors of the invention and means for cleaving the palindromic cleavage sites.

DESCRIPTION OF THE SEQUENCE LISTING

Figure 1:
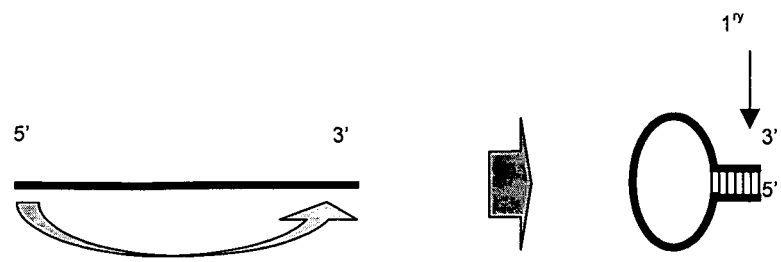
FIG. 1 shows one embodiment of a Type I adaptor. The single stranded DNA strand has self complementarity such that it will hybridise to itself, leaving a large hairpin loop of single stranded DNA, which is used to selectively bind the 'Type I adaptor' ligation products during the purification. The terminus of the self hybridised adaptor encodes one half of the primary Restriction Endonuclease (arrowed, $1^{ry}$), utilised to cleave any ligation products created by adaptor: adaptor ligations, whether Type I:Type I, Type I:Type II or Type II:Type II.

SEQ ID NO: 1 shows the polynucleotide sequence encoding one subunit of wild type α-hemolysin (α-HL).

SEQ ID NO: 2 shows the amino acid sequence of one subunit of wild type α-HL. Amino acids 2 to 6, 73 to 75, 207 to 209, 214 to 216 and 219 to 222 form α-helices. Amino acids 22 to 30, 35 to 44, 52 to 62, 67 to 71, 76 to 91, 98 to 103, 112 to 123, 137 to 148, 154 to 159, 165 to 172, 229 to 235, 243 to 261, 266 to 271, 285 to 286 and 291 to 293 form β-strands. All the other non-terminal amino acids, namely 7 to 21, 31 to 34, 45 to 51, 63 to 66, 72, 92 to 97, 104 to 111, 124 to 136, 149 to 153, 160 to 164, 173 to 206, 210 to 213, 217, 218, 223 to 228, 236 to 242, 262 to 265, 272 to 274 and 287 to 290 form loop regions. Amino acids 1 and 294 are terminal amino acids.

SEQ ID NO: 3 shows the polynucleotide sequence encoding one subunit of α-HL M113R/N139Q (HL-RQ).

SEQ ID NO: 4 shows the amino acid sequence of one subunit of α-HL M113R/N139Q (HL-RQ). The same amino acids that form α-helices, β-strands and loop regions in wild type α-HL form the corresponding regions in this subunit.

SEQ ID NO: 5 shows the codon optimised polynucleotide sequence derived from the sbcB gene from *E. coli*. It encodes the exonuclease I enzyme (EcoExoI) from *E. coli*.

SEQ ID NO: 6 shows the amino acid sequence of exonuclease I enzyme (EcoExoI) from *E. coli*. This enzyme performs processive digestion of 5' monophosphate nucleosides from single stranded DNA (ssDNA) in a 3'-5' direction. Amino acids 60 to 68, 70 to 78, 80 to 93, 107 to 119, 124 to 128, 137 to 148, 165 to 172, 182 to 211, 213 to 221, 234 to 241, 268 to 286, 313 to 324, 326 to 352, 362 to 370, 373 to 391, 401 to 454 and 457 to 475 form α-helices. Amino acids 10 to 18, 28 to 26, 47 to 50, 97 to 101, 133 to 136, 229 to 232, 243 to 251, 258 to 263, 298 to 302 and 308 to 311 form β-strands. All the other non-terminal amino acids, 19 to 27, 37 to 46, 51 to 59, 69, 79, 94 to 96102 to 106, 120 to 123, 129 to 132, 149 to 164, 173 to 181, 212, 222 to 228, 233, 242, 252 to 257, 264 to 267, 287 to 297, 303 to 307, 312, 325, 353 to 361, 371, 372, 392 to 400, 455 and 456, form loops. Amino acids 1 to 9 are terminal amino acids. The overall fold of the enzyme is such that three regions combine to form a molecule with the appearance of the letter C, although residues 355-358, disordered in the crystal structure, effectively convert this C into an O-like shape. The amino terminus (1-206) forms the exonuclease domain and has homology to the DnaQ superfamily, the following residues (202-354) form an SH3-like domain and the carboxyl domain (359-475) extends the exonuclease domain to form the C-like shape of the molecule. Four acidic residues of EcoExoI are conserved with the active site residues of the DnaQ superfamily (corresponding to D15, E17, D108 and D186). It is suggested a single metal ion is bound by residues D15 and 108. Hydrolysis of DNA is likely catalyzed by attack of the scissile phosphate with an activated water molecule, with H181 being the catalytic residue and aligning the nucleotide substrate.

SEQ ID NO: 7 shows the codon optimised polynucleotide sequence derived from the recJ gene from *T. thermophilus*. It encodes the RecJ enzyme from *T. thermophilus* (TthRecJ-cd).

SEQ ID NO: 8 shows the amino acid sequence of the RecJ enzyme from *T. thermophilus* (TthRecJ-cd). This enzyme performs processive digestion of 5' monophosphate nucleosides from ssDNA in a 5'-3' direction. Enzyme initiation on a strand requires at least 4 nucleotides. Amino acids 19 to 33, 44 to 61, 80 to 89, 103 to 111, 136 to 140, 148 to 163, 169 to 183, 189 to 202, 207 to 217, 223 to 240, 242 to 252, 254 to 287, 302 to 318, 338 to 350 and 365 to 382 form α-helices. Amino acids 36 to 40, 64 to 68, 93 to 96, 116 to 120, 133 to 135, 294 to 297, 321 to 325, 328 to 332, 352 to 355 and 359 to 363 form n-strands. All the other non-terminal amino acids, 34, 35, 41 to 43, 62, 63, 69 to 79, 90 to 92, 97 to 102, 112 to 115, 121 to 132, 141 to 147, 164 to 168, 184 to 188 203 to 206, 218 to 222, 241, 253, 288 to 293, 298 to 301, 319, 320, 326, 327, 333 to 337, 351 to 358 and 364, form loops. Amino acids 1 to 18 and 383 to 425 are terminal amino acids. The crystal structure has only been resolved for the core domain of RecJ from *Thermus thermophilus* (residues 40-463). To ensure initiation of translation and in vivo expression of the RecJ core domain a methionine residue was added at its amino terminus, this is absent from the crystal structure information. The resolved structure shows two domains, an amino (2-253) and a carboxyl (288-463) region, connected by a long α-helix (254-287). The catalytic residues (D46, D98, H122, and D183) co-ordinate a single divalent metal ion for nucleophilic attack on the phosphodiester bond. D46 and H120 proposed to be the catalytic pair; however, mutation of any of these conserved residues in the *E. coli* RecJ was shown to abolish activity.

SEQ ID NO: 9 shows the sequence of the I-SceI homing endonuclease recognition site.

SEQ ID NO: 10 shows the nucleic sequence from which preferred nucleic acid linkers can be generated.

SEQ ID NO: 11 shows a preferred nucleic acid linker. MAL is maleimide. This linker is used in combination with SEQ ID NO: 14.

SEQ ID NO: 12 shows a preferred nucleic acid linker. MAL is maleimide. This linker is used in combination with SEQ ID NO: 15.

SEQ ID NO: 13 shows a preferred nucleic acid linker. MAL is maleimide. This linker is used in combination with SEQ ID NO: 16.

SEQ ID NO: 14 shows a preferred 15mer nucleic acid linker. MAL is maleimide. This linker is complementary to and used in combination with SEQ ID NO: 11.

SEQ ID NO: 15 shows a preferred 15mer nucleic acid linker. MAL is maleimide. This linker is complementary to and used in combination with SEQ ID NO: 12.

SEQ ID NO: 16 shows a preferred 15mer nucleic acid linker. MAL is maleimide. This linker is complementary to and used in combination with SEQ ID NO: 13.

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "a construct" includes "constructs", reference to "a transmembrane pore" includes two or more such pores, reference to "a molecular adaptor" includes two or more such adaptors, and the like.

All publications, patents and patent applications cited herein, whether supra or infra, are hereby incorporated by reference in their entirety.

Adaptor

The invention provides adaptors for sequencing nucleic acids. The adaptors comprise a region of double stranded nucleic acid. At least one end of the region forms one half of a palindromic cleavage site. The adaptors are differentially selectable from other adaptors. In some embodiments, the region is formed by hybridization between two separated regions of a single stranded nucleic acid and the adaptors comprise a hairpin loop. Adaptors of the invention are typically used as part of a pair of adaptors.

The adaptors of the invention have several advantages. The adaptors facilitate construction, purification and final release of a desired single stranded sequencing construct, which comprises both strands of a double stranded nucleic acid template. This ensures that, when the construct is sequenced, each position in the double stranded nucleic acid is not merely observed once, but is in fact interrogated twice. This gives greater certainty that each position in the nucleic acid has been observed and that the aggregate call for both bases at each position is of a greater quality score than would be possible with a single observation. In other words, the key advantage of the adaptors of the invention is that they allow each 'base pair' position of a double stranded template to be effectively interrogated twice as part of the same 'read event'. This ensures that the quality of the sequence generated is consequently very much higher, with a reduced potential for misidentified base calls, or completely missed bases.

This is particularly helpful for the sequencing of dsDNA or dsRNA. The adaptors of the invention allow the production of constructs containing both the sense and antisense strands of dsDNA and dsRNA. Each 'base pair' position of the dsDNA or dsRNA can effectively be interrogated twice; once on the sense strand and once on the antisense strand.

This ability to interrogate each position twice is particularly important when sequencing nucleic acids using stochastic sensing. Such sequencing normally depends on the capture of every base in turn by the transmembrane pore and a sufficiently high sampling rate to enable accurate determination of the degree to which the current flowing through the pore is reduced. Being able to effectively interrogate every base twice reduces the need to capture every base at a sufficiently high rate.

In addition, the adaptors of the invention allow the nucleic acid to be provided in a form suitable for stochastic sensing. Only single stranded nucleic acids can be threaded through transmembrane pores. In addition, many nucleic acid handling enzymes, which are an integral part of the sequencing methods described herein, are capable of only handling single stranded nucleic acids.

The ability to interrogate each position twice is also helpful for differentiating between methylcytosine and thymine using stochastic sensing. These two bases result in very similar current traces when they pass through and interact with a transmembrane pore. It can therefore be difficult to differentiate between the two. However, interrogation of each position in a nucleic acid twice will allow such differentiation because the complementary base for methylcytosine is guanine, whereas the complementary base for thymine is adenine. Methylcytosine has of course been linked with various diseases, including cancer.

Being artificial sequences, the adaptors of the invention have a great degree of flexibility in their actual sequence and therefore functionality can be built into the sequences used. For instance, an adaptor-specific sequence can be built into each adaptor. This allows a construct containing a particular adaptor to be differentiated from one containing a different adaptor. This is particularly helpful for multiplex sequence analysis of templates originating from separate individual sources.

The adaptors are for sequencing nucleic acids. The adaptors are preferably for sequencing a double stranded nucleic acid by generating a single stranded nucleic acid construct that contains both strands of the double stranded nucleic acid template. The adaptors are more preferably for sequencing dsDNA or dsRNA by generating a single stranded nucleic acid construct that contains both the sense and antisense strands of the dsDNA or dsRNA.

Region of Double Stranded Nucleic Acid

The adaptors comprise a region of double stranded nucleic acid. The presence of this region means that the adaptors of the invention are capable of ligating to other double stranded nucleic acids, such as dsDNA or dsRNA. The adaptors of the invention are also capable of ligating to themselves or other types of adaptors. As described in more detail below, such ligation will result in the formation of a complete palindromic cleavable site. Suitable conditions that allow the ligation of the adaptors of the invention to double stranded nucleic acids or themselves are discussed below.

The region of double stranded nucleic acid may comprise any type of nucleic acid. A nucleic acid is a macromolecule comprising two or more nucleotides. The nucleic acid handled may comprise any combination of any nucleotides. The nucleotides can be naturally occurring or artificial. A nucleotide typically contains a nucleobase, a sugar and at least one phosphate group. The nucleobase is typically heterocyclic. Nucleobases include, but are not limited to, purines and pyrimidines and more specifically adenine, guanine, thymine, uracil and cytosine. The sugar is typically a pentose sugar. Nucleotide sugars include, but are not limited to, ribose and deoxyribose. The nucleotide is typically a ribonucleotide or deoxyribonucleotide. The nucleotide typically contains a monophosphate, diphosphate or triphosphate. Phosphates may be attached on the 5' or 3' side of a nucleotide.

Nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP). The nucleotides are preferably selected from AMP, TMP, GMP, CMP, UMP, dAMP, dTMP, dGMP or dCMP.

The nucleic acid can be deoxyribonucleic acid (DNA) or ribonucleic acid (RNA). The nucleic acid may include two strands of any synthetic nucleic acid known in the art, such as peptide nucleic acid (PNA), glycerol nucleic acid (GNA), threose nucleic acid (TNA), locked nucleic acid (LNA) or other synthetic polymers with nucleotide side chains. When sequencing a double stranded nucleic acid template, the nucleic acid in the adaptor is chosen such that the adaptors are capable of ligating to the double stranded nucleic acid being sequenced.

The region of double stranded nucleic acid may be any length as long as the palindromic cleavage site is functional when two adaptors ligate together. The region will typically be 40 or fewer base pairs, such as 30 or fewer base pairs, 20 or fewer base pairs or 10 or fewer base pairs, in length. The region is preferably 5 to 20 base pairs in length and more preferably 6 to 10 base pairs in length.

The region may be formed by hybridization of two separate strands of single stranded nucleic acid. The two separate strands may be the same type of nucleic acid or different types of nucleic acid as long as they hybridise. The two separate strands can be any of the types of nucleic acid described above. Suitable conditions that allow hybridization of nucleic acids are discussed in more detail below.

The region of double stranded nucleic acid is preferably formed by hybridization of two separated regions of a single stranded nucleic acid such that the adaptor comprises a hairpin loop. In the context of the invention, Type I adaptors comprise a hairpin loop. This allows Type I adaptors to covalently link two strands of a double nucleic acid template. Type II adaptors may or may not comprise a hairpin loop. It is preferred that the Type II adaptors comprise a hairpin loop. The formation of hairpin loops is known in the art. The hairpin loop is typically formed from single stranded nucleic acid. The hairpin loop may be the same type of nucleic acid as that making up the region of double stranded nucleic acid. Alternatively, the hairpin loop may be a different type of nucleic acid from that making up the region of double stranded nucleic acid. The hairpin loop can be any of the types of nucleic acid described above. As discussed in more detail below, the hairpin loop may be involved in the differential selectability of the adaptors of the invention. For instance, the hairpin loop may comprise a selectable binding moiety.

The hairpin loop may be any length. The hairpin loop is typically 50 or fewer bases, such as 40 or fewer bases, 30 or fewer bases, 20 or fewer bases or 10 or fewer bases, in length. The hairpin loop is preferably from about 1 to 50, from 2 to 40 or from 6 to 30 bases in length. Longer lengths of the hairpin loop, such as from 15 to 50 bases, are preferred if the loop is involved in the differential selectability of the adaptor. Similarly, shorter lengths of the hairpin loop, such as from 1 to 5 bases, are preferred if the loop is not involved in the differential selectability of the adaptor.

In adaptors without a hairpin loop, the region of double stranded nucleic acid will have two free ends. One or both of these ends may ligate to a double stranded nucleic acid template. At least one end forms one half of a palindromic cleavage site. Both ends preferably form one half of the same palindromic cleavage site. One or both ends may also be involved in the differential selectability of the adaptors of the invention. Preferably, one end of the adaptor may ligate to a double stranded nucleic acid template and forms one half of a palindromic cleavage site and the other end is involved in the differential selectability of the adaptor.

In adaptors with a hairpin loop, the region of double stranded nucleic acid will have only one free end. The other end is closed by the hairpin loop. The free end not only forms one half of a palindromic cleavage site, but also may ligate to a double stranded nucleic acid template.

The free end(s) of the region of double stranded nucleic acid may be in any form. The end(s) can be sticky. In other words, the end(s) do not have to form a base pair. The sticky end(s) may have a 5' or 3' overhang. It is preferred that the end(s) are blunt. In other words, it is preferred that the end(s) form a base pair. It is particularly preferred that the end(s) of the region forming one half of a palindromic cleavage site are blunt.

In adaptors without a hairpin loop, it is preferred that the end that ligates to a double stranded nucleic acid template and forms one half of a palindromic cleavage site is blunt and the other end that is involved in the differential selectability of the adaptor is sticky.

One Half of a Palindromic Cleavage Site

A palindromic cleavage site is a palindromic consensus sequence in a nucleic acid that may be cleaved in some manner. Several such sequences are known in the art and may be used in the invention. Preferred palindromic cleavage sites are shown below.

One half of a palindromic cleavage site is exactly one half of a palindromic consensus sequence. In other words, it is the amount of a palindromic cleavage site that when recombined with itself forms a complete palindromic cleavage site. As discussed above, the ends forming the one half of the palindromic cleavage site may be sticky or blunt. For instance, for a palindromic cleavage site having the following sequence:

```
5'...AAAATTTT...3'
3'...TTTTAAAA...5'
``` one half of the palindromic cleavage site can be

```
5'...AAAA...3'
3'...TTTT...5'
or
5'...AAAAT...3'
3'...TTT...5'
or
5'...AAA...3'
3'...TTTTA...5'
```

In the examples above, the first one half of the palindromic cleavage site has blunt ends, while the second two one halves of the palindromic cleavage site have sticky ends.

As discussed above, the adaptors of the invention are typically used in pairs with one type of adaptor in the pair being differentially selectable from the other type of adaptor in the pair. Since both types adaptors in the pair comprise one half a palindromic cleavage site, a complete palindromic cleavage site is formed when one type of adaptor ligates with an adaptor of the same type or of a different type. For instance, a complete palindromic cleavage site will be formed if Type I ligates to Type I (Type I:Type I), Type II ligates to Type II (Type II:Type II) or Type I ligates to Type II (Type I:Type II). The formation of a complete palindromic cleavage site allows the ligated adaptors to be cleaved. This is discussed in more detail below.

The complete palindromic cleavage site may be any length. For instance, palindromic cleavage sites are typically from 8 to 50 base pairs, such as at least 10 base pairs, at least 12 base pairs, at least 14 base pairs, at least 16 base pairs, at least 20 base pairs, at least 30 base pairs or at least 40 base pairs, in length. For sequencing purposes, the longer the palindromic cleavage site the better because the less likely the sequence will appear randomly in an organism's genome. In a completely random genome sequence (which of course is never found in nature), a palindromic cleavage site of x base pairs in length would be found once every $4^x$ base pairs.

Preferred palindromic cleavage sites include restriction endonuclease recognition sites. Restriction endonuclease recognition sites are sites that are cleaved by restriction endonuclease enzymes. Suitable restriction endonuclease enzymes for use in the invention include, but are not limited to, those in Enzyme Classification (EC) groups 3.1.21.4 and 3.1.21.5.

The restriction endonuclease recognition site may be a naturally occurring site that is cleaved by a naturally occurring restriction endonuclease enzyme. Alternatively, the restriction endonuclease recognition site and/or the restriction endonuclease may be non-naturally occurring. Engineering a restriction endonuclease recognition site and/or a restriction endonuclease for use in the invention offers various advantages. For instance, engineering an endonuclease to cleave a long and/or rare site means that the endonuclease is less likely to "accidentally" cleave one or more sites with the double stranded nucleic acid template being interrogated.

Preferred restriction endonuclease recognition sites include, but are not limited to, the following:

```
SbfI
5'...CCTGCAGG...3'
3'...GGACGTCC...5'
and

AsiSI
5'...GCGATCGC...3'
3'...CGCTAGCG...5'
```

Preferred halves of these sites therefore include, but are not limited to, the following:

```
SbfI
5'...CCTG...3'
3'...GGAC...5'

SbfI
5'...CCT...3'
3'...GGACG...5'

SbfI
5'...AGG...3'
3'...CGTCC...5'

AsiSI
5'...GCGA...3'
3'...CGCT...5'
```

```
AsiSI
5'...CGC...3'

3'...TAGCG...5'
and

AsiSI
5'...GCG...3'

3'...CGCTA...5'
```

Differential Selectability

Adaptors of the invention are differentially selectable from other adaptors. Adaptors of the invention are differentially selectable from different types of adaptor of the invention. Type I adaptors are differentially selectable from Type II adaptors. Differential selectability means that one type of adaptor can be delineated or distinguished from another type of the adaptor on the basis of at least one property. Any property may be used to differentially select different types of adaptors.

Generally, different types of adaptors are differentially selectable because they can be separated from each other. When used in pairs, each type of adaptor in the pair can be separated from the other type. For instance, Type I adaptors can be separated from Type II adaptors and vice versa. This facilitates the method of the invention discussed in more detail below. Any means of separation can be used.

Differential selection preferably involves differential or selective binding to a surface. For instance, two types of adaptors of the invention can of course be differentially selected if only one binds to surface A and only the other binds to surface B. Adaptors of the invention are therefore differentially selectable if they specifically bind to a surface. Adaptors specifically bind to a surface if they bind to the surface to a much greater degree than adaptors of a different type. In preferred embodiments, the adaptors bind to a surface to which no other types of adaptor bind. Suitable surfaces are discussed in more detail below.

It is most preferred that the adaptors can be separated from other adaptors by differential binding. For instance, it is possible to separate two types of adaptor (for example Types A and B) from each other if the first type of adaptor (Type A) specifically binds to one surface (surface A) and the second type of adaptor (Type B) binds to another surface (surface B). A mixture of two types of adaptor will contain unligated adaptors of both types, as well as ligated constructs of Type A:Type A, Type B:Type B and Type A:Type B. Contacting the mixture with surface A will result in the binding of Type A adaptors and any constructs comprising a Type A adaptor. Similarly, contacting the mixture with surface B will result in the binding of Type B adaptors and any constructs comprising a Type B adaptor. Ligated constructs can of course be cleaved using the palindromic cleavage site.

The adaptors preferably comprise a selectable binding moiety. A selectable binding moiety is a moiety that can be selected on the basis of its binding properties. Hence, a selectable binding moiety is preferably a moiety that specifically binds to a surface. A selectable binding moiety specifically binds to a surface if it binds to the surface to a much greater degree than any other moiety used in the invention. In preferred embodiments, the moiety binds to a surface to which no other moiety used in the invention binds. If present, the hairpin loop preferably comprises the selective binding moiety.

Suitable selective binding moieties are known in the art. Preferred selective binding moieties include, but are not limited to, biotin, a nucleic acid sequence, antibodies, antibody fragments, such as Fab and ScSv, antigens, nucleic acid binding proteins, poly histidine tails and GST tags. The most preferred selective binding moieties are biotin and a selectable nucleic acid sequence. Biotin specifically binds to a surface coated with avidins. Selectable nucleic acid sequences specifically bind (i.e. hybridise) to a surface coated with homologous sequences. This is discussed in more detail below. Alternatively, selectable nucleic acid sequences specifically bind to a surface coated with nucleic acid binding proteins. In the most preferred embodiment, one type of adaptor in a pair of adaptors comprises biotin and the other type of adaptor comprises a selectable nucleic acid sequence.

Identification Sequences

In preferred embodiments, the adaptors comprise a nucleic acid sequence that allows identification of the adaptor. The nucleic acid sequence may be present in the region of double stranded nucleic acid or, if present, the hairpin loop.

The nucleic acid sequence is typically 12 or fewer bases, such as 10 or fewer bases, 8 or fewer bases or 6 or fewer bases, in length. It comprises a recognizable sequence that can be identified when a construct comprising the adaptor is sequenced in accordance with the invention. In adaptors that comprising a hairpin loop, the sequence will be identified as the adaptor part that links the two strands of nucleic acid to be interrogated is sequenced. In adaptors that lack a hairpin loop and are capable of being cleaved or nicked, the sequence is typically present between the end that ligates to the double stranded nucleic acid template and the point at which adaptor can be cleaved or nicked. In such embodiments, the sequence remains ligated to the double stranded nucleic acid template even once the adaptor is cleaved or nicked.

In preferred embodiments, the nucleic acid sequence identifies the source of the two strands to which it is ligated. In such embodiments, the adaptor allows multiplex sequence analysis of templates originating from separate individual sources. Each template is assigned a different adaptor, each of which comprises a nucleic acid sequence that allows identification of the source of the template.

Adaptors that are Capable of being Cleaved or Nicked

In some embodiments, the adaptor is itself capable of being cleaved or nicked. In other words, the adaptor may be cleaved or nicked without having to ligate to another adaptor. The region of double stranded nucleic acid may be capable of being cleaved or nicked and/or, if present, the hairpin loop may be capable of being cleaved or nicked. In adaptors with a hairpin loop, it is preferred that the end of the adaptor that forms one half of a palindromic cleavage site (i.e. the end of the adaptor that ligates to the double stranded sequence template) can be separated from the selectable binding moiety. In adaptors without a hairpin loop, it is preferred that one or both ends of the adaptor can be separated from the selectable binding moiety.

Adaptors that are capable of being cleaved or nicked preferably contain one or more, such as two, three or more, cleavage or nick sites. Any cleavage or nick site may be used in accordance with the invention. Such sites include, but are not limited to, chemical cleavage or nick sites, RNA/DNA composite sites, non-natural bases (e.g. uracil) and restriction endonuclease recognition sites and homing endonuclease recognition sites.

Adaptors that are capable of being cleaved or nicked more preferably comprise one or more restriction or homing endonuclease recognition sites. It is preferred that the restriction or homing endonuclease recognition site(s) are not the palindromic cleavage site formed if the adaptor ligates to another adaptor of the invention. Suitable restriction or homing endonuclease recognition sites are known in the art. Preferred homing endonuclease recognition sites include, but are not limited to, the following:

```
        I-SceI
                                (SEQ ID NO: 9)
        5'...TAGGGATAACAGGGTAAT...3'

3'...ATCCCTATTGTCCCATTA...5'
```

Pairs of Adaptors

The invention also provides pairs of adaptors of the invention. One type of adaptor in the pair is formed by hybridization between two separated regions of a single stranded nucleic acid and comprises a hairpin loop (Type I). The other type of adaptor in the pair may or may not have a hairpin loop (Type II). The Type II adaptor is preferably also formed by hybridization between two separated regions of a single stranded nucleic acid and comprises a hairpin loop. Each type of adaptor in the pair is differentially selectable from the other type. A complete palindromic cleavage site is formed if any combination of the two types of adaptor are ligated to one another. The adaptors may be any of those discussed above.

It is preferred that the Type adaptor I can be separated from the Type II adaptor and vice versa. Any method of separation described above can be used. It is more preferred that the Type I adaptor can be separated from the Type II adaptor by differential binding. It is even more preferred that the Type I adaptor comprises a different selectable binding moiety from the Type II adaptor. Preferably, the Type I adaptor comprises a selectable nucleic acid and the Type II adaptor comprises biotin. All of these embodiments facilitate the method of the invention discussed in more detail below.

It is also preferred that the Type I adaptor is not itself capable of being cleaved or nicked and that the Type II is itself capable of being cleaved or nicked. The Type II adaptor may be cleaved or nicked in any of the ways discussed above.

It is further preferred that the Type I adaptor comprises a nucleic acid sequence that allows identification of the adaptor.

The most preferred pair of adaptors of the invention is summarised in Table 1 below.

| Type I | Type II |
|---|---|
| Hairpin present | Hairpin present |
| Selectable nucleic acid | Biotin |
| Not itself capable of being cleaved or nicked | Itself capable of being cleaved or nicked |
| Nucleic acid sequence that allows identification of the adaptor | Nucleic acid sequence that allows identification of the adaptor |

Kits

The invention also provides kits comprising at least two populations of adaptors of the invention formed by hybridization between two separated regions of a single stranded nucleic acid and comprising a hairpin loop (Type I). Every adaptor in each population comprises a nucleic acid sequence that is specific for the population. In other words, each adaptor in a population comprises a sequence that allows the adaptor to be identified as being part of that population and not part of one of the other populations. The two or more populations allow multiplex sequence analysis of double stranded nucleic acid templates originating from two or more separate individual sources, such as from two or more organisms. Suitable organisms are discussed below. Each template is assigned a different population, each of which comprises a nucleic acid sequence that allows identification of the source of the template. The identifying nucleic acid sequence will be different in each population. The sequence is typically located at the same position in the adaptors of each of the two or more populations. This allows efficient differentiation between the populations. Nucleic acid sequences that allow identification of adaptors are discussed in more detail above. Any of the embodiments discussed above are applicable to the kits of the invention.

The kits may comprise any number of populations, such as 5, 10, 20, 50, 100 or more populations.

The kits preferably further comprise two or more populations of Type II adaptors such that every Type I adaptor forms a pair with a Type II adaptor. Pairs of adaptors are discussed in more detail above. Any of the embodiments discussed above are applicable to the kits of the invention.

The present invention also provides kits for sequencing double stranded nucleic acid comprising a pair of adaptors of the invention and means for cleaving the palindromic cleavage site. The means is typically an enzyme as discussed above.

The kits of the invention may additionally comprise one or more other reagents or instruments which enable any of the embodiments mentioned above to be carried out. Such reagents or instruments include one or more of the following: suitable buffer(s) (aqueous solutions), means to obtain a sample from a subject (such as a vessel or an instrument comprising a needle), means to amplify, express and/or sequence polynucleotide sequences, a membrane as defined above, a surface as defined above or voltage or patch clamp apparatus. Reagents may be present in the kit in a dry state such that a fluid sample resuspends the reagents. The kit may also, optionally, comprise instructions to enable the kit to be used in the method of the invention or details regarding which patients the method may be used for. The kit may, optionally, comprise nucleotides.

Nucleic Acid Constructs

The present invention also provides nucleic acid constructs for use as sequence templates. The constructs are useful for sequencing double stranded nucleic acids. The constructs generally comprise two strands of nucleic acid ligated to at least one adaptor of the invention. It is typically the sequence of the two strands of nucleic acid that needs to be determined.

In one embodiment, the invention provides nucleic acid constructs for use as a sequencing template comprising a double stranded nucleic acid ligated to at least one adaptor of the invention. The construct may comprise two adaptors, one ligated to each end of the double stranded nucleic acid. The construct may comprise any of the adaptors discussed above.

In another embodiment, the invention provides single stranded nucleic acid constructs for use as a sequencing template comprising two strands of nucleic acid covalently linked via an adaptor of the invention formed by hybridization between two separated regions of a single stranded nucleic acid and comprising a hairpin loop (Type I). The two strands are typically derived from a double stranded nucleic acid, such as dsDNA or dsRNA. The construct may comprise any of the Type I adaptors discussed above. Such constructs have several advantages as described above. In some instances, it may be necessary to denature the construct to yield a single stranded structure. Suitable conditions for denaturing nucleic acids are discussed in more detail below.

In a further embodiment, the invention provides circular nucleic acid constructs comprising two strands of nucleic acid covalently linked at each end via an adaptor of the invention formed by hybridization between two separated regions of a single stranded nucleic acid and comprising a hairpin loop (Type I). The two strands are typically derived from a double stranded nucleic acid, such as dsDNA or dsRNA. The construct may comprise any of the Type I adaptors discussed above.

In all these embodiments, the two strands are preferably the sense and antisense strands of dsDNA or dsRNA.

Methods for Preparing Adaptors of the Invention

The invention also provides methods for preparing adaptors of the invention. The methods involve providing two nucleic acids that are (i) capable of hybridizing to one another to form one half of a palindromic cleavage site and (ii) differentially selectable from those of another adaptor. These features are all discussed in detail above with reference to the adaptors of the invention. The nucleic acids are contacted under conditions which allow them to hybridise and prepare an adaptor of the invention. Such conditions are discussed in detail below.

The invention also provides methods for preparing Type I adaptors. The methods involve providing a single stranded nucleic acid comprising (i) two regions that are capable of hybridizing to one another, (ii) a loop-forming region that is differentially selectable from that of another adaptor and (iii) two ends which together form one half of a palindromic cleavage site. These features are all discussed in detail above with reference to the adaptors of the invention. The nucleic acid is exposed to conditions which allow the two regions to hybridise and form a hairpin loop and thereby prepare a Type I adaptor.

The nucleic acids or regions that are capable of hybridizing to one another preferably share at least 80%, at least 85%, at least 90%, at least 95%, at least 98%, at least 99% homology based on sequence identity. The nucleic acids or regions are more preferably complementary (i.e. share 100% homology based on sequence identity).

Standard methods in the art may be used to determine homology. For example the UWGCG Package provides the BESTFIT program which can be used to calculate homology, for example used on its default settings (Devereux et al (1984) *Nucleic Acids Research* 12, p 387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F et al (1990) *J Mol Biol* 215:403-10.

Software for performing BLAST analyses is publicly available through the National Center for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra).

These initial neighbourhood word hits act as seeds for initiating searches to find HSP's containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) *Proc. Natl. Acad. Sci. USA* 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) *Proc. Natl. Acad. Sci. USA* 90: 5873-5787. One measure of similarity provided by the BLAST algorithm is the smallest sum probability (P(N)), which provides an indication of the probability by which a match between two amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

Conditions that permit the hybridization are well-known in the art (for example, Sambrook et al., 2001, Molecular Cloning: a laboratory manual, 3rd edition, Cold Spring Harbour Laboratory Press; and Current Protocols in Molecular Biology, Chapter 2, Ausubel et al., Eds., Greene Publishing and Wiley-Interscience, New York (1995)). Hybridization can be carried out under low stringency conditions, for example in the presence of a buffered solution of 30 to 35% formamide, 1 M NaCl and 1% SDS (sodium dodecyl sulfate) at 37° C. followed by a wash in from 1× (0.1650 M Na+) to 2× (0.33 M Na+) SSC (standard sodium citrate) at 50° C. Hybridization can be carried out under moderate stringency conditions, for example in the presence of a buffer solution of 40 to 45% formamide, 1 M NaCl, and 1% SDS at 37° C., followed by a wash in from 0.5× (0.0825 M Na+) to 1× (0.1650 M Na+) SSC at 55° C. Hybridization can be carried out under high stringency conditions, for example in the presence of a buffered solution of 50% formamide, 1 M NaCl, 1% SDS at 37° C., followed by a wash in 0.1× (0.0165 M Na+) SSC at 60° C.

Methods for Preparing Constructs of the Invention

The invention also provides various methods for preparing the constructs of the invention. The constructs of the invention are discussed above. Any of the constructs of the invention can be made using these methods.

In one embodiment, the invention provides methods for preparing nucleic acid constructs of the invention. The methods involve contacting at least one adaptor of the invention with two strands of nucleic acid under conditions which allow ligation between the adaptor(s) and the strands. Any of the adaptors discussed above may be used. The two strands are typically derived from a double stranded nucleic acid, such as dsDNA or dsRNA. Conditions suitable for ligating nucleic acids are known in the art. Such conditions include, but are not limited to, 50 mM Tris-HCl, 10 mM MgCl$_2$, 1 mM ATP, 10 mM Dithiothreitol, pH 7.5 and 25° C. The adaptor(s) are then allowed to ligate to the two strands and thereby prepare a nucleic acid construct.

In another embodiment, the invention provides methods for preparing single stranded nucleic acid constructs of the invention. The methods involve contacting a Type I adaptor with two strands of nucleic acid under conditions which allow ligation between the adaptor and the strands. Any of the Type I adaptors discussed above may be used. The two strands are typically derived from a double stranded nucleic acid, such as dsDNA or dsRNA.

Conditions suitable for ligating nucleic acids are discussed above. The adaptor is allowed to covalently link the two strands at each end. The covalently linked constructs are then denatured to prepare single stranded nucleic acid constructs. Suitable conditions for denaturing nucleic acids include, but are not limited to, pH, temperature and ionic strength.

In yet another embodiment, the invention provides method for preparing circular nucleic acid constructs of the invention. The methods involve contacting at least two Type I adaptors with two strands of nucleic acid under conditions which allow ligation between the adaptors and strands. The at least two Type I adaptors may be the same or different. Any of the Type I adaptors discussed above may be used. The two strands are typically derived from a double stranded nucleic acid, such as dsDNA or dsRNA. Conditions suitable for ligating nucleic acids are discussed above. An adaptor is then allowed to covalently link the two strands at each end and thereby prepare circular nucleic acid constructs.

In yet another embodiment, the invention provides methods for preparing sequence constructs. The methods prepare single stranded nucleic acid constructs comprising the two strands of a double stranded nucleic acid covalently linked via a Type I adaptor. The methods involve providing double stranded nucleic acid. The providing preferably involves randomly fragmenting template nucleic acid. The ends of the double stranded nucleic acid may be repaired to form blunt ends. Any of the nucleic acids disclosed above can be used. The methods are typically carried out using a double stranded nucleic acid whose sequence is unknown. Alternatively, the methods may be carried out using a double stranded nucleic acid whose sequence is known or can be predicted.

The methods may be carried out in vitro on double stranded nucleic acid obtained from or extracted from any organism or microorganism. The organism or microorganism is typically prokaryotic, eukaryotic or an archon and typically belongs to one the five kingdoms: plantae, animalia, fungi, monera and protista. The methods may be carried out in vitro on double stranded nucleic acid obtained from or extracted from any virus. Typically, the double stranded nucleic acid is human in origin, but alternatively it may be from another mammal animal such as from commercially farmed animals such as horses, cattle, sheep or pigs or may alternatively be pets such as cats or dogs.

The double stranded nucleic acid is typically processed prior to undergoing the methods, for example by centrifugation or by passage through a membrane that filters out unwanted molecules or cells, such as red blood cells. The double stranded nucleic acid may be used immediately upon being taken. The double stranded nucleic acid may also be typically stored prior to undergoing the methods, preferably below −70° C.

The double stranded nucleic acid is preferably dsDNA or dsRNA.

The double stranded nucleic acid is contacted with a pair of Type I and Type II adaptors of the invention under conditions which allow the adaptors to ligate to the nucleic acid. The Type II adaptor is itself capable of being cleaved or nicked as discussed above. Conditions suitable for ligating nucleic acids are discussed above. Suitable pairs of Type I adaptors and Type II adaptors are also discussed above.

The ligated products are then contacted with a surface that specifically binds the Type II adaptors that are capable of being cleaved or nicked. Any constructs containing Type II adaptors will bind to the surface. Suitable surfaces include, but are not limited to, metal (gold in particular), agarose, dextran, polystyrene, glass, silica (bonded and unbonded) and cellulose. Preferably, the surface specifically binds a selectable binding moiety on the Type II adaptors. The surface is most preferably coated with avidins.

Any unbound products are then removed. This is typically done by washing the surface with a suitable buffer. Suitable buffers include, but are not limited to, Tris, HEPES and MOPS at suitable ionic concentrations. This step removes all constructs formed by the ligation of a Type I adaptor to a Type I adaptor (Type I:Type I).

The surface is then contacted with an enzyme that recognises the complete palindromic cleavage site. Suitable enzymes are discussed above. This step will cleave any remaining (i.e. bound) constructs formed from the ligation of an adaptor to an adaptor, i.e. Type I:Type II or Type II:Type II.

Again, any unbound products are removed, typically by washing. This step ensures that only Type II adaptors in isolation or constructs containing the double stranded nucleic acid and at least one Type II adaptor remain bound to the surface.

The Type II adaptors are then cleaved. Methods for doing this are discussed above. This step ensures the release of the constructs containing the double stranded nucleic acid and at least one Type II adaptor from the surface.

The soluble products are then contacted with a surface that specifically binds the Type I adaptors that are not capable of being cleaved or nicked. Any remaining constructs containing Type I adaptors bind to the surface. Each construct will contain the double stranded nucleic acid covalently linked at one end via a Type I adaptor. The surface preferably specifically binds a selectable binding moiety on the Type I adaptors. The surface is more preferably coated with nucleic acid sequences that are at least 80%, such as least 90%, at least 95% or at least 99%, homologous based on sequence identity to a selectable nucleic acid sequence in the Type I adaptors. The surface is most preferably coated with nucleic acid sequences that are complementary to a selectable nucleic acid sequence in the Type I adaptors. Again, unbound products are removed.

Finally, any remaining products are released from the surface. Those released products represent a sequencing construct of the invention in which a double stranded nucleic acid is covalently linked at one end via a Type I adaptor. The construct may also contain fragments of the Type II adaptor at the ends of the double stranded nucleic acid.

The resulting construct may need to be denatured to form a single stranded construct. Conditions suitable for denaturing double stranded nucleic acids are discussed above.

Methods of Sequencing Double Stranded Nucleic Acid

The invention also provides methods of sequencing double stranded nucleic acid. The methods involve carrying out one of the methods described above for preparing nucleic acid constructs. The construct contains two strands of nucleic acid, preferably DNA or RNA, covalently linked via a Type I adaptor. If necessary, the construct is denatured to form a single stranded construct. Conditions for doing this are described above.

The single stranded construct is then be sequenced. Sequencing the single stranded construct will provide the sequence of, in order, one strand, the Type I adaptor and the other strand. The strands will of course be in opposite orientations. In some embodiments, fragments of the Type II adaptors may also be present in the single stranded nucleic acid construct.

The methods of the invention are advantageous because each position in the double stranded nucleic acid is interrogated twice (i.e. once on each strand). The methods preferably involve sequencing double stranded nucleic acid containing or suspected of containing methylcytosine. If the Type I adaptor comprises a nucleic acid sequence that identifies the source of the double stranded nucleic acid, this will also be recognised using the methods of the invention.

The whole or only part of the construct may be sequenced using these methods. The construct can be any length. For example, the construct can be at least 10, at least 50, at least 100, at least 150, at least 200, at least 250, at least 300, at least 400 or at least 500 nucleotides in length. The methods are typically carried out in vitro.

By effectively doubling the interrogation of every base, the invention may improve the data quality of all existing second generation sequencing chemistries and next generation sequencing technologies in development. Any method of sequencing the single stranded nucleic acid construct may be used in accordance with the invention. Suitable methods are known in the art. Such methods include, but are not limited to, Sanger (or dideoxy) method, the Maxam-Gilbert (chemical cleavage) method, Life Technologies' SOLiD (which uses sequencing by ligation), Illumina Genome Analyser (which uses fluorescent reversible terminator chemistry on amplified templates), 454 Genome Sequencer FLX (which uses pyrosequencing chemistry on amplified templates), Helicos Heliscope (which uses true single molecule sequencing by fluorescent reversible terminator chemistry on unamplified (adapter modified) templates), Bionanomatrix (electronic discrimination of bases in etched channels), Danaher Motion ('polony' sequencing), LingVitae ('design polymer' sequencing), Pacific BioSciences' Single Molecule Sequencing by fluorescent nucleotide DNA polymerization and Visigen's (Sequencing by FRET interaction of donor and acceptor during a DNA polymerisation reaction).

There are also a number of ways that transmembrane pores can be used to sequence nucleic acid molecules. One way involves the use of an exonuclease enzyme, such as a deoxyribonuclease. In this approach, the exonuclease enzyme is used to sequentially detach the nucleotides from a target nucleic strand. The nucleotides are then detected and discriminated by the pore in order of their release, thus reading the sequence of the original strand.

Another way of sequencing nucleic acids involves the use of an enzyme that pushes or pulls the target nucleic acid strand through the pore in combination with an applied potential. In this approach, the ionic current fluctuates as a nucleotide in the target strand passes through the pore. The fluctuations in the current are indicative of the sequence of the strand.

A third way of sequencing a nucleic acid strand is to detect the byproducts of a polymerase in close proximity to a pore detector. In this approach, nucleoside phosphates (nucleotides) are labelled so that a phosphate labelled species is released upon the addition of a polymerase to the nucleotide strand and the phosphate labelled species is detected by the pore. The phosphate species contains a specific label for each nucleotide. As nucleotides are sequentially added to the nucleic acid strand, the bi-products of the base addition are detected. The order that the phosphate labelled species are detected can be used to determine the sequence of the nucleic acid strand.

Any of these three methods can be used to sequence in accordance with the invention.

In one preferred embodiment, the sequencing is carried out by methods comprising (i) contacting the construct with a transmembrane pore having an exonuclease and a molecular adaptor covalently attached thereto so that the exonuclease digests an individual nucleotide from one end of the construct; (ii) contacting the nucleotide with the pore so that the nucleotide interacts with the molecular adaptor; (iii) measuring the current passing through the pore during the interaction and thereby determining the identity of the nucleotide; and (iv) repeating steps (i) to (iii) at the same end of the construct and thereby determining the sequence of the target sequence. Hence, the methods involve stochastic sensing of a proportion of the nucleotides in the construct in a successive manner in order to sequence the construct. Individual nucleotides are described below.

In another preferred embodiment, the sequencing is carried out by methods comprising (i) contacting the construct with a transmembrane pore having a nucleic acid handling enzyme attached thereto so that the enzyme pushes or pulls the construct through the pore and a proportion of the nucleotides in the construct interacts with the pore and (ii) measuring the current passing through the pore during each interaction and thereby determining the sequence of the construct. Hence, the methods involve stochastic sensing of a proportion of the nucleotides in a construct as the nucleotides pass through the barrel or channel in a successive manner in order to sequence the construct.

Transmembrane Pores

A transmembrane pore is a pore that permits ions driven by an applied potential to flow from one side of a membrane to the other side of the membrane. The pore preferably permits nucleotides to flow from one side of a membrane to the other along the applied potential. The pore preferably allows a nucleic acid, such as DNA or RNA, to be pushed or pulled through the pore.

The pore is preferably a transmembrane protein pore. A transmembrane protein pore is a polypeptide or a collection of polypeptides that permits ions driven by an applied potential to flow from one side of a membrane to the other side of the membrane.

The pore may be isolated, substantially isolated, purified or substantially purified. A pore is isolated or purified if it is completely free of any other components, such as lipids or other pores. A pore is substantially isolated if it is mixed with carriers or diluents which will not interfere with its intended use. For instance, a pore is substantially isolated or substantially purified if it present in a form that comprises less than 10%, less than 5%, less than 2% or less than 1% of other components, such as lipids or other pores. The pore is typically present in a lipid bilayer.

The pore may be a monomer or an oligomer. The pore is preferably made up of several repeating subunits, such as 6, 7 or 8 subunits. The pore is more preferably a heptameric pore. The pore typically comprises a barrel or channel through which the ions may flow. The subunits of the pore typically surround a central axis and contribute strands to a transmembrane β barrel or channel or a transmembrane α-helix bundle or channel.

The barrel or channel of the pore typically comprises amino acids that facilitate interaction with nucleotides or nucleic acids. These amino acids are preferably located near a constriction of the barrel or channel. The pore typically comprises one or more positively charged amino acids, such as arginine, lysine or histidine. These amino acids typically facilitate the interaction between the pore and nucleotides or nucleic acids. The nucleotide detection can be facilitated with an adaptor. This is discussed in more detail below.

Pores for use in accordance with the invention can be β-barrel pores, α-helix bundle pores or solid state pores. β-barrel pores comprise a barrel or channel that is formed from β-strands. Suitable β-barrel pores include, but are not limited to, β-toxins, such as α-hemolysin, anthrax toxin and leukocidins, and outer membrane proteins/porins of bacteria, such as *Mycobacterium smegmatis* porin A (MspA), outer membrane porin F (OmpF), outer membrane porin G (OmpG), outer membrane phospholipase A and *Neisseria* autotransporter lipoprotein (NalP). α-helix bundle pores comprise a barrel or channel that is formed from α-helices. Suitable α-helix bundle pores include, but are not limited to, inner membrane proteins and a outer membrane proteins, such as WZA.

Suitable solid state pores include, but are not limited to, silicon nitride pores, silicon dioxide pores and graphene pores. Other suitable solid state pores and methods of producing them are discussed in U.S. Pat. No. 6,464,842, WO 03/003446, WO 2005/061373, U.S. Pat. Nos. 7,258, 838, 7,466,069, 7,468,271 and 7,253,434.

The pore is preferably derived from α-hemolysin (α-HL). The wild type α-HL pore is formed of seven identical monomers or subunits (i.e. it is heptameric). The sequence of one wild type monomer or subunit of α-hemolysin is shown in SEQ ID NO: 2. The pore preferably comprises seven subunits of the sequence shown in SEQ ID NO: 2 or a variant thereof. Amino acids 1, 7 to 21, 31 to 34, 45 to 51, 63 to 66, 72, 92 to 97, 104 to 111, 124 to 136, 149 to 153, 160 to 164, 173 to 206, 210 to 213, 217, 218, 223 to 228, 236 to 242, 262 to 265, 272 to 274, 287 to 290 and 294 of SEQ ID NO: 2 form loop regions. Residues 113 and 147 of SEQ ID NO: 2 form part of a constriction of the barrel or channel of α-HL.

A variant of SEQ ID NO: 2 is a subunit that has an amino acid sequence which varies from that of SEQ ID NO: 2 and which retains its pore forming ability. The ability of a variant to form a pore can be assayed using any method known in the art. For instance, the variant may be inserted into a membrane along with other appropriate subunits and its ability to oligomerise to form a pore may be determined.

The variant may include modifications that facilitate covalent attachment to or interaction with the nucleic acid handling enzyme. The variant preferably comprises one or more reactive cysteine residues that facilitate attachment to the enzyme. For instance, the variant may include a cysteine at one or more of positions 8, 9, 17, 18, 19, 44, 45, 50, 51, 237, 239 and 287 and/or on the amino or carboxy terminus of SEQ ID NO: 2. Preferred variants comprise a substitution of the residue at position 8, 9, 17, 237, 239 and 287 of SEQ ID NO: 2 with cysteine (K8C, T9C, N17C, K237C, S239C or E287C).

The variant may be modified to facilitate genetic fusion of the enzyme. For instance, one or more residues adjacent to the insertion site may be modified, such as deleted, to facilitate insertion of the enzyme and/or linkers. If the enzyme is inserted into loop 2 of SEQ ID NO: 2, one or more of residues D45, K46, N47, H48, N49 and K50 of SEQ ID NO: 2 may be deleted.

The variant may also include modifications that facilitate any interaction with nucleotides or facilitate orientation of a molecular adaptor as discussed below. The variant may also contain modifications that facilitate covalent attachment of a molecular adaptor.

In particular, the variant preferably has a glutamine at position 139 of SEQ ID NO: 2. The variant preferably has an arginine at position 113 of SEQ ID NO: 2. The variant preferably has a cysteine at position 119, 121 or 135 of SEQ ID NO: 2. SEQ ID NO: 4 shows the sequence of SEQ ID NO: 2 except that it has an arginine at position 113 (M113R) and a glutamine at position 139 (N139Q). SEQ ID NO: 4 or a variant thereof may be used to form a pore in accordance with the invention.

The variant may be a naturally occurring variant which is expressed naturally by an organism, for instance by a *Staphylococcus* bacterium, or expressed recombinantly by a bacterium such as *Escherichia coli*. Variants also include non-naturally occurring variants produced by recombinant technology. Over the entire length of the amino acid sequence of SEQ ID NO: 2 or 4, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 2 or 4 over the entire sequence. There may be at least 80%, for example at least 85%, 90% or 95%, amino acid identity over a stretch of 200 or more, for example 230, 250, 270 or 280 or more, contiguous amino acids ("hard homology").

Amino acid substitutions may be made to the amino acid sequence of SEQ ID NO: 2 or 4 in addition to those discussed above, for example up to 1, 2, 3, 4, 5, 10, 20 or 30 substitutions. Conservative substitutions may be made, for example, according to Table 2 below.

TABLE 2

Conservative substitutions
Amino acids in the same block in the second column and preferably in the same line in the third column may be substituted for each other.

| | | |
|---|---|---|
| NON-AROMATIC | Non-polar | G A P |
| | | I L V |
| | Polar - uncharged | C S T M |
| | | N Q |
| | Polar - charged | D E |
| | | H K R |
| AROMATIC | | H F W Y |

One or more amino acid residues of the amino acid sequence of SEQ ID NO: 2 may additionally be deleted from the polypeptides described above. Up to 1, 2, 3, 4, 5, 10, 20 or 30 residues may be deleted, or more.

Variants may fragments of SEQ ID NO: 2 or 4. Such fragments retain pore forming activity. Fragments may be at least 50, 100, 200 or 250 amino acids in length. A fragment preferably comprises the pore forming domain of SEQ ID NO: 2 or 4. Fragments typically include residues 119, 121, 135, 113 and 139 of SEQ ID NO: 2 or 4.

One or more amino acids may be alternatively or additionally added to the polypeptides described above. An extension may be provided at the amino terminus or carboxy terminus of the amino acid sequence of SEQ ID NO: 2 or 4 or a variant or fragment thereof. The extension may be quite short, for example from 1 to 10 amino acids in length. Alternatively, the extension may be longer, for example up to 50 or 100 amino acids. A carrier protein may be fused to a pore or variant.

As discussed above, a variant of SEQ ID NO: 2 or 4 is a subunit that has an amino acid sequence which varies from that of SEQ ID NO: 2 or 4 and which retains its ability to form a pore. A variant typically contains the regions of SEQ ID NO: 2 or 4 that are responsible for pore formation. The pore forming ability of α-HL, which contains a β-barrel, is provided by β-strands in each subunit. A variant of SEQ ID NO: 2 or 4 typically comprises the regions in SEQ ID NO: 2 that form β-strands. The amino acids of SEQ ID NO: 2 or 4 that form β-strands are discussed above. One or more modifications can be made to the regions of SEQ ID NO: 2 or 4 that form β-strands as long as the resulting variant retains its ability to form a pore. Specific modifications that can be made to the β-strand regions of SEQ ID NO: 2 or 4 are discussed above.

A variant of SEQ ID NO: 2 or 4 preferably includes one or more modifications, such as substitutions, additions or deletions, within its α-helices and/or loop regions. Amino acids that form α-helices and loops are discussed above.

The variant may be modified for example by the addition of histidine or aspartic acid residues to assist its identification or purification or by the addition of a signal sequence to promote their secretion from a cell where the polypeptide does not naturally contain such a sequence.

The pore may be labelled with a revealing label. The revealing label may be any suitable label which allows the pore to be detected. Suitable labels include, but are not limited to, fluorescent molecules, radioisotopes, e.g. $^{125}$I, $^{35}$S, $^{14}$C, enzymes, antibodies, antigens, polynucleotides and ligands such as biotin.

The pore may be isolated from a pore producing organism, such as *Staphylococcus aureus*, or made synthetically or by recombinant means. For example, the pore may be synthesised by in vitro translation and transcription. The amino acid sequence of the pore may be modified to include non-naturally occurring amino acids or to increase the stability of the pore. When the pore is produced by synthetic means, such amino acids may be introduced during production. The pore may also be altered following either synthetic or recombinant production.

The pore may also be produced using D-amino acids. For instance, the pores may comprise a mixture of L-amino acids and D-amino acids. This is conventional in the art for producing such proteins or peptides.

The pore may also contain other non-specific chemical modifications as long as they do not interfere with its ability to form a pore. A number of non-specific side chain modifications are known in the art and may be made to the side chains of the pores. Such modifications include, for example, reductive alkylation of amino acids by reaction with an aldehyde followed by reduction with NaBH$_4$, amidination with methylacetimidate or acylation with acetic anhydride. The modifications to the pore can be made after expression of each subunit or after the subunits have been used to form a pore.

The pore can be produced using standard methods known in the art. Polynucleotide sequences encoding a pore or pore subunit may be isolated and replicated using standard methods in the art. Polynucleotide sequences encoding a pore or pore subunit may be expressed in a bacterial host cell using standard techniques in the art. The pore may be produced in a cell by in situ expression of the polypeptide from a recombinant expression vector. The expression vector optionally carries an inducible promoter to control the expression of the polypeptide.

A pore may be produced in large scale following purification by any protein liquid chromatography system from pore producing organisms or after recombinant expression as described below. Typical protein liquid chromatography systems include FPLC, AKTA systems, the Bio-Cad system, the Bio-Rad BioLogic system and the Gilson HPLC system.

Nucleic Acid Handling Enzyme

A nucleic acid handling enzyme is a polypeptide that is capable of interacting with and modifiying at least one property of a nucleic acid. The enzyme may modify the nucleic acid by cleaving it to form individual nucleotides or shorter chains of nucleotides, such as di- or trinucleotides. The enzyme may modify the nucleic acid by orienting it or moving it to a specific position. Any of the nucleic acids discussed above may be handled by the enzyme.

The nucleic acid handled by the enzyme is preferably single stranded. The nucleic acid handled by the enzyme may be double stranded, such as dsDNA or dsRNA. Enzymes that handle single stranded nucleic acids may be used to sequence double stranded DNA as long as the double stranded DNA is chemically or thermally dissociated into a single strand before it is handled by the enzyme.

It is preferred that the tertiary structure of the nucleic acid handling enzyme is known. Knowledge of the three dimensional structure of the enzyme allows modifications to be made to the enzyme to facilitate its function in the methods of the invention.

The enzyme may be any size and have any structure. For instance, the enzyme may be an oligomer, such as a dimer or trimer. The enzyme is preferably a small, globular polypeptide formed from one monomer. Such enzymes are easy to handle and are less likely to interfere with the pore forming ability of the pore or pore subunit, particularly if fused to or inserted into the sequence of the pore or pore subunit.

The amino and carboxy terminii of the enzyme are preferably in close proximity. The amino and carboxy terminii of the enzyme are more preferably presented on same face of the enzyme. Such embodiments facilitate insertion of the enzyme into the sequence of the pore or pore subunit. For instance, if the amino and carboxy terminii of the enzyme are in close proximity, each can be attached by genetic fusion to adjacent amino acids in the sequence of the pore or pore subunit.

It is also preferred that the location and function of the active site of the enzyme is known. This prevents modifications being made to the active site that abolish the activity of the enzyme. It also allows the enzyme to be attached to the pore so that the enzyme handles the construct in such a way that a proportion of the nucleotides in the construct interacts with the pore. It is beneficial to position the active site of the enzyme as close as possible to the part of the pore that forms part of the opening of the barrel of channel of the pore, without the enzyme itself presenting a block to the flow of current. Knowledge of the way in which an enzyme may orient nucleic acids also allows an effective pore-enzyme construct to be designed.

In order that most of the nucleotides in the construct are correctly identified by stochastic sensing, the enzyme must handle the nucleic acid in a buffer background which is compatible with discrimination of the nucleotides. The enzyme preferably has at least residual activity in a salt concentration well above the normal physiological level, such as from 100 mM to 2000 mM. The enzyme is more preferably modified to increase its activity at high salt concentrations. The enzyme may also be modified to improve its processivity, stability and shelf life.

Suitable modifications can be determined from the characterisation of nucleic acid handling enzymes from extremphiles such as halophilic, moderately halophilic bacteria, thermophilic and moderately thermophilic organisms, as well as directed evolution approaches to altering the salt tolerance, stability and temperature dependence of mesophilic or thermophilic exonucleases.

The enzyme also preferably retains at least partial activity at temperatures from 10° C. to 60° C., such as at room temperature. This allows the construct to sequence nucleic acids at a variety of temperatures, including room temperature.

The nucleic acid handling enzyme is preferably a nucleolytic enzyme. The nucleic acid handling enzyme is more preferably member of any of the Enzyme Classification (EC) groups 3.1.11, 3.1.13, 3.1.14, 3.1.15, 3.1.16, 3.1.21, 3.1.22, 3.1.25, 3.1.26, 3.1.27, 3.1.30 and 3.1.31. The nucleic acid handling enzyme is more preferably any one of the following enzymes:

- 3.1.11.- Exodeoxyribonucleases producing 5'-phosphomonoesters.
  - 3.1.11.1 Exodeoxyribonuclease I.
  - 3.1.11.2 Exodeoxyribonuclease III.
  - 3.1.11.3 Exodeoxyribonuclease (lambda-induced).
  - 3.1.11.4 Exodeoxyribonuclease (phage SP3-induced).
  - 3.1.11.5 Exodeoxyribonuclease V.
  - 3.1.11.6 Exodeoxyribonuclease VII.
- 3.1.13.- Exoribonucleases producing 5'-phosphomonoesters.
  - 3.1.13.1 Exoribonuclease II.
  - 3.1.13.2 Exoribonuclease H.
  - 3.1.13.3 Oligonucleotidase.
  - 3.1.13.4 Poly(A)-specific ribonuclease.
  - 3.1.13.5 Ribonuclease D.
- 3.1.14.- Exoribonucleases producing 3'-phosphomonoesters.
  - 3.1.14.1 Yeast ribonuclease.
- 3.1.15.- Exonucleases active with either ribo- or deoxyribonucleic acid producing 5' phosphomonoesters
  - 3.1.15.1 Venom exonuclease.
- 3.1.16.- Exonucleases active with either ribo- or deoxyribonucleic acid producing 3' phosphomonoesters
  - 3.1.16.1 Spleen exonuclease.
- 3.1.21.- Endodeoxyribonucleases producing 5'-phosphomonoesters.
  - 3.1.21.1 Deoxyribonuclease I.
  - 3.1.21.2 Deoxyribonuclease IV (phage-T(4)-induced).
  - 3.1.21.3 Type I site-specific deoxyribonuclease.
  - 3.1.21.4 Type II site-specific deoxyribonuclease.
  - 3.1.21.5 Type III site-specific deoxyribonuclease.
  - 3.1.21.6 CC-preferring endodeoxyribonuclease.
  - 3.1.21.7 Deoxyribonuclease V.
- 3.1.22.- Endodeoxyribonucleases producing other than 5'-phosphomonoesters.
  - 3.1.22.1 Deoxyribonuclease II.
  - 3.1.22.2 *Aspergillus* deoxyribonuclease K(1).
  - 3.1.22.3 Transferred entry: 3.1.21.7.
  - 3.1.22.4 Crossover junction endodeoxyribonuclease.
  - 3.1.22.5 Deoxyribonuclease X.
- 3.1.25.- Site-specific endodeoxyribonucleases specific for altered bases.
  - 3.1.25.1 Deoxyribonuclease (pyrimidine dimer).
  - 3.1.25.2 Transferred entry: 4.2.99.18.
- 3.1.26.- Endoribonucleases producing 5'-phosphomonoesters.
  - 3.1.26.1 *Physarum polycephalum* ribonuclease.
  - 3.1.26.2 Ribonuclease alpha.
  - 3.1.26.3 Ribonuclease III.
  - 3.1.26.4 Ribonuclease H.
  - 3.1.26.5 Ribonuclease P.
  - 3.1.26.6 Ribonuclease IV.
  - 3.1.26.7 Ribonuclease P4.
  - 3.1.26.8 Ribonuclease M5.
  - 3.1.26.9 Ribonuclease (poly-(U)-specific).
  - 3.1.26.10 Ribonuclease IX.
  - 3.1.26.11 Ribonuclease Z.
- 3.1.27.- Endoribonucleases producing other than 5'-phosphomonoesters.
  - 3.1.27.1 Ribonuclease T(2).
  - 3.1.27.2 *Bacillus subtilis* ribonuclease.
  - 3.1.27.3 Ribonuclease T(1).
  - 3.1.27.4 Ribonuclease U(2).
  - 3.1.27.5 Pancreatic ribonuclease.
  - 3.1.27.6 *Enterobacter* ribonuclease.
  - 3.1.27.7 Ribonuclease F.
  - 3.1.27.8 Ribonuclease V.
  - 3.1.27.9 tRNA-intron endonuclease.
  - 3.1.27.10 rRNA endonuclease.
- 3.1.30.- Endoribonucleases active with either ribo- or deoxyribonucleic producing 5' phosphomonoesters
  - 3.1.30.1 *Aspergillus* nuclease S(1).
  - 3.1.30.2 *Serratia marcescens* nuclease.
- 3.1.31.- Endoribonucleases active with either ribo- or deoxyribonucleic producing 3' phosphomonoesters
  - 3.1.31.1 Micrococcal nuclease.

The enzyme is most preferably an exonuclease, such as a deoxyribonuclease, which cleave nucleic acids to form individual nucleotides. The advantages of exodeoxyribonucleases are that they are active on both single stranded and double stranded DNA and hydrolyse bases either in the 5'-3' or 3'-5' direction.

An individual nucleotide is a single nucleotide. An individual nucleotide is one which is not bound to another nucleotide or nucleic acid by any bond, such as a phosphodiester bond. A phosphodiester bond involves one of the phosphate groups of a nucleotide being bound to the sugar group of another nucleotide. An individual nucleotide is typically one which is not bound in any manner to another nucleic acid sequence of at least 5, at least 10, at least 20, at least 50, at least 100, at least 200, at least 500, at least 1000 or at least 5000 nucleotides.

Preferred enzymes for use in the method include exonuclease I from *E. coli* (SEQ ID NO: 6) and RecJ from *T. thermophilus* (SEQ ID NO: 8) and variants thereof. The exonuclease enzyme preferably comprises any of the sequences shown in SEQ ID NOs: 6 and 8 or a variant thereof. A variant of SEQ ID NO: 6 or 8 is an enzyme that has an amino acid sequence which varies from that of SEQ ID NO: 6 or 8 and which retains nucleic acid handling ability. The ability of a variant to handle nucleic acids can be assayed using any method known in the art. For instance, the variant or a pore having the variant attached thereto can be tested for their ability to handle specific sequences of nucleic acids. The enzyme may include modifications that facilitate handling of the nucleic acid and/or facilitate its activity at high salt concentrations and/or room temperature. The enzyme may include modifications that facilitate covalent attachment to or its interaction with the pore or pore subunit. As discussed above, accessible cysteines may be removed from the enzyme to avoid non-specific reactions with a linker. Alternatively, one or more reactive cysteines may be introduced into the enzyme, for instance as part of a genetically-fused peptide linker, to facilitate attachment to the pore or pore subunit.

Variants may differ from SEQ ID NO: 6 or 8 to the same extent as variants of SEQ ID NO: 2 differ from SEQ ID NO: 2 or 4 as discussed above.

A variant of SEQ ID NO: 6 or 8 retains its nucleic acid handling activity. A variant typically contains the regions of SEQ ID NO: 6 or 8 that are responsible for nucleic acid handling activity. The catalytic domains of SEQ ID NOs: 6 and 8 are discussed above. A variant of SEQ ID NO: 6 or 8 preferably comprises the relevant catalytic domain. A variant SEQ ID NO: 6 or 8 typically includes one or more modifications, such as substitutions, additions or deletions, outside the relevant catalytic domain.

Preferred variants of SEQ ID NO: 6 or 8 are described in a co-pending application being filed simultaneously with this application [J A Kemp & Co Ref: N.106566; Oxford Nanolabs Ref: ONL IP 007] which is incorporated herein by reference. All the teachings of that application may be applied equally to the present invention.

Preferred enzymes that are capable of pushing or pulling the construct through the pore include polymerases, exonucleases, helicases and topoisomerases, such as gyrases. The polymerase is preferably a member of any of the Enzyme Classification (EC) groups 2.7.7.6, 2.7.7.7, 2.7.7.19, 2.7.7.48 and 2.7.7.49. The polymerase is preferably a DNA-dependent DNA polymerase, an RNA-dependent DNA polymerase, a DNA-dependent RNA polymerase or an RNA-dependent RNA polymerase. The helicase is preferably a member of any of the Enzyme Classification (EC) groups 3.6.1.- and 2.7.7.-. The helicase is preferably an ATP-dependent DNA helicase (EC group 3.6.1.8), an ATP-dependent RNA helicase (EC group 3.6.1.8) or an ATP-independent RNA helicase. The topoisomerase is preferably a member of any of the Enzyme Classification (EC) groups 5.99.1.2 and 5.99.1.3.

The enzyme may be labelled with a revealing label. The revealing label may be any of those described above.

The enzyme may be isolated from an enzyme-producing organism, such as *E. coli, T. thermophilus* or bacteriophage, or made synthetically or by recombinant means. For example, the enzyme may be synthesised by in vitro translation and transcription as described above and below. The enzyme may be produced in large scale following purification as described above.

Covalent Attachment of the Enzyme to the Pore

In order to effectively sequence the construct, it is important to ensure that a proportion of the nucleotides in the construct is identified in a successive manner. The fixed nature of the enzyme means that a proportion of the nucleotides in the construct affects the current flowing through the pore.

The enzyme attached to the pore handles a construct in such a way that a proportion of the nucleotide in the construct interacts with the pore, preferably the barrel or channel of the pore. Nucleotides are then distinguished on the basis of the different ways in which they affect the current flowing through the pore during the interaction.

The fixed nature of the enzyme means that a construct is handled by the pore in a specific manner. For instance, each nucleotide may be digested from one of the construct in a processive manner or the construct may be pushed or pulled through the pore. This ensures that a proportion of the nucleotides in the construct interacts with the pore and is identified. The lack of any interruption in the signal is important when sequencing nucleic acids. In addition, the fixed nature of the enzyme and the pore means they can be stored together, thereby allowing the production of a ready-to-use sensor.

In a preferred embodiment, an exonuclease enzyme, such as a deoxyribonuclease, is attached to the pore such that a proportion of the nucleotides is released from the construct and interacts with the barrel or channel of the pore. In another preferred embodiment, an enzyme that is capable of pushing or pulling the construct through the pore is attached to the pore such that the construct is pushed or pulled through the barrel or channel of the pore and a proportion of the nucleotides in the construct interacts with the barrel or channel. In this embodiment, the nucleotides may interact with the pore in blocks or groups of more than one, such as 2, 3 or 4. Suitable enzymes include, but are not limited to, polymerases, nucleases, helicases and topoisomerases, such as gyrases. In each embodiment, the enzyme is preferably attached to the pore at a site in close proximity to the opening of the barrel of channel of the pore. The enzyme is more preferably attached to the pore such that its active site is orientated towards the opening of the barrel of channel of the pore. This means that a proportion of the nucleotides of the construct is fed in the barrel or channel. The enzyme is preferably attached to the cis side of the pore.

The pore is attached to the enzyme. The pore may be attached to the enzyme at more than one, such as two or three, points. Attaching the pore to the enzyme at more than one point can be used to constrain the mobility of the enzyme. For instance, multiple attachments may be used to constrain the freedom of the enzyme to rotate or its ability to move away from the pore or pore subunit.

The pore may be in a monomeric form when it is attached to the enzyme (post expression modification). Alternatively, the pore may be an oligomeric pore when it is attached to an enzyme (post oligomerisation modification).

The pore or pore subunit can be attached to the enzyme using any method known in the art. The pore or pore subunit and enzyme may be produced separately and then attached together. The two components may be attached in any configuration. For instance, they may be attached via their terminal (i.e. amino or carboxy terminal) amino acids. Suitable configurations include, but are not limited to, the amino terminus of the enzyme being attached to the carboxy terminus of the pore or pore subunit and vice versa. Alternatively, the two components may be attached via amino acids within their sequences. For instance, the enzyme may be attached to one or more amino acids in a loop region of the pore or pore subunit. In a preferred embodiment, terminal amino acids of the enzyme are attached to one or more amino acids in the loop region of a pore or pore subunit. Terminal amino acids and loop regions are discussed above.

In one preferred embodiment, the pore or pore subunit is genetically fused to the enzyme. A pore or pore subunit is genetically fused to an enzyme if the whole construct is expressed from a single polynucleotide sequence. The coding sequences of the pore or pore subunit and enzyme may be combined in any way to form a single polynucleotide sequence encoding the construct.

The pore or pore subunit and enzyme may be genetically fused in any configuration. The pore or pore subunit and enzyme may be fused via their terminal amino acids. For instance, the amino terminus of the enzyme may be fused to the carboxy terminus of the pore or pore subunit and vice versa. The amino acid sequence of the enzyme is preferably added in frame into the amino acid sequence of the pore or pore subunit. In other words, the enzyme is preferably inserted within the sequence of the pore or pore subunit. In such embodiments, the pore or pore subunit and enzyme are typically attached at two points, i.e. via the amino and carboxy terminal amino acids of the enzyme. If the enzyme is inserted within the sequence of the pore or pore subunit, it is preferred that the amino and carboxy terminal amino acids of the enzyme are in close proximity and are each attached to adjacent amino acids in the sequence of the pore or pore subunit. In a preferred embodiment, the enzyme is inserted into a loop region of the pore or pore subunit. In an especially preferred embodiment, the enzyme is inserted between amino acids, 18 and 19, 44 and 45 or 50 and 51 of SEQ ID NO: 2.

In another preferred embodiment, the pore or pore subunit is chemically fused to the enzyme. A pore or pore subunit is chemically fused to an enzyme if the two parts are chemically attached, for instance via a linker molecule. Suitable methods include, but are not limited to, hex-his tag, Ni-NTA, biotin binding to streptavidin, antibody binding to an antigen, primary amine coupling, GST tags binding to glutathione, MBP tags binding to dextrin, Protein A binding to IgG, reaction between thiols, nucleic acid hybridization linkers and cysteine linkage. DNA hybridization linkers and cysteine linkage are discussed in more detail below. The pore or pore subunit is preferably covalently attached to the enzyme.

The pore must retain its pore forming ability. The pore forming ability of the pore is typically provided by its α-helices and β-strands. ρ-barrel pores comprise a barrel or channel that is formed from β-strands, whereas α-helix bundle pores comprise a barrel or channel that is formed from α-helices. The α-helices and β-strands are typically connected by loop regions. In order to avoid affecting the pore forming ability, the enzyme is preferably genetically fused to a loop region of the pore or pore subunit or inserted into a loop region of the pore or pore subunit. The loop regions of specific subunits are discussed in more detail above. In a preferred embodiment, enzyme is attached to one or more of amino acids 8, 9, 17, 18, 19, 44, 45, 50 and 51 of SEQ ID NO: 2.

Similarly, the construct retains the nucleic acid handling ability of the enzyme, which is also typically provided by its secondary structural elements (α-helices and β-strands) and tertiary structural elements. In order to avoid adversely affecting the nucleic acid handling ability of the enzyme, the enzyme is preferably genetically fused to the pore or pore subunit or inserted into the pore or pore subunit via residues or regions that does not affect its secondary or tertiary structure.

The pore or pore subunit may be attached directly to the enzyme. The pore or pore subunit is preferably attached to the enzyme using one or more, such as two or three, linkers.

The one or more linkers may be designed to constrain the mobility of the enzyme. The linkers may be attached to one or more reactive cysteine residues, reactive lysine residues or non-natural amino acids in the pore, pore subunit subunit and/or enzyme. Suitable linkers are well-known in the art. Suitable linkers include, but are not limited to, chemical crosslinkers and peptide linkers. Preferred linkers are amino acid sequences (i.e. peptide linkers) or nucleic acid hybridization linkers. The length, flexibility and hydrophilicity of the peptide or nucleic acid hybridization linkers are typically designed such that it does not to disturb the functions of the pore or pore subunit and enzyme. Preferred flexible peptide linkers are stretches of 2 to 20, such as 4, 6, 8, 10 or 16, serine and/or glycine amino acids. More preferred flexible linkers include $(SG)_1$, $(SG)_2$, $(SG)_3$, $(SG)_4$, $(SG)_5$ and $(SG)_8$ wherein S is serine and G is glycine. Preferred rigid linkers are stretches of 2 to 30, such as 4, 6, 8, 16 or 24, proline amino acids. More preferred rigid linkers include $(P)_{12}$ wherein P is proline.

The nucleic acid hybridization linkers can comprise any of the nucleic acids discussed above. For instance, they may comprise deoxyribonucleic acid (DNA), ribonucleic acid (RNA) or any synthetic nucleic acid known in the art, such as peptide nucleic acid (PNA), glycerol nucleic acid (GNA), threose nucleic acid (TNA), locked nucleic acid (LNA) or other synthetic polymers with nucleotide side chains. The linkers can also be modified such they react with one another once they have hybridised. Alternatively, agents may be used to crosslink the linkers once they have hybridised to one another.

Preferred nucleic acid hybridization linkers correspond to the first 15, 25 or 35 nucleotides from the 5' end of SEQ ID NO: 10. The linker preferably also has TT at the 3' end to provide extra flexibility. At the 3' end, the linkers have a group, such as maleimide, that allows the linker to be attached to the nucleic acid binding protein or surface. Maleimide modified oliognucleotides can be obtained commercially, for instance from ATDBio. More preferred linkers are shown in SEQ ID NOs: 11, 12 and 13. Complementary linkers are shown in SEQ ID NOs: 14, 15 and 16. SEQ ID NO: 11, 12 or 13 may be attached to one of the nucleic acid binding protein and surface and the complementary linker (SEQ ID NO: 14, 15 or 16 respectively) is attached to the other of the nucleic acid binding protein and surface. The nucleic acid binding protein and surface can then be attached together by hybridizing the linkers.

Other preferred chemical crosslinkers are shown in the following Table 3.

TABLE 3

Some preferred linkers

| Name | Reacts with | Structure |
|---|---|---|
| 1,4-Bis[3-(2-pyridyldithio)propionamido]butane | Thiols | 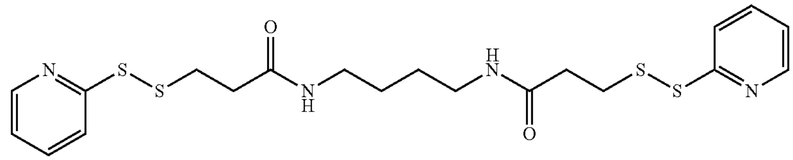 [SMILES: O=C(CCSSc1ccccn1)NCCCCNC(=O)CCSSc1ccccn1] |
| 1,11-bis-Maleimidotriethyleneglycol | Thiols | 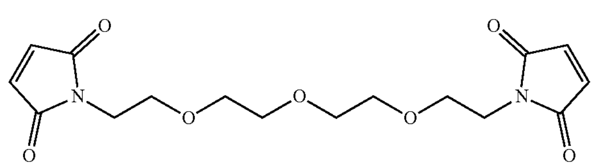 [SMILES: O=C1C=CC(=O)N1CCOCCOCCOCCN1C(=O)C=CC1=O] |

TABLE 3-continued

Some preferred linkers

| Name | Reacts with | Structure |
|---|---|---|
| 3,3'-Dithiodipropionic acid di(N-hydroxysuccinimide ester) | Primary amines | 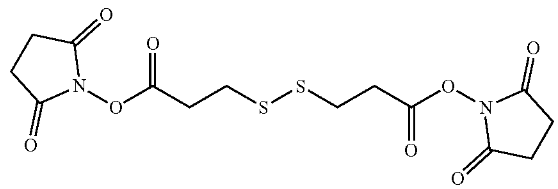 [SMILES: O=C(CCSSCCC(=O)ON1C(=O)CCC1=O)ON1C(=O)CCC1=O] |
| Ethylene glycol-bis(succinic acid N-hydroxysuccinimide ester) | Primary amines | 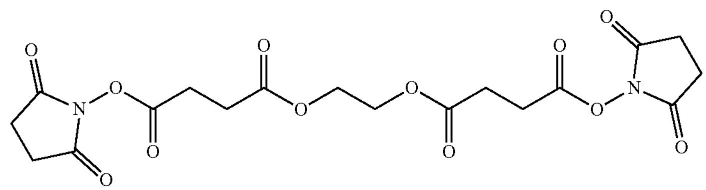 [SMILES: O=C(CCC(=O)ON1C(=O)CCC1=O)OCCOC(=O)CCC(=O)ON1C(=O)CCC1=O] |
| 4,4'-Diisothiocyanatostilbene-2,2'-disulfonic acid disodium salt | Primary amines | 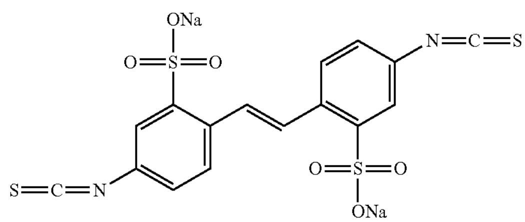 |
| Bis[2-(4-azidosalicylamido)ethyl] disulfide | Photo-activated, non-specific | 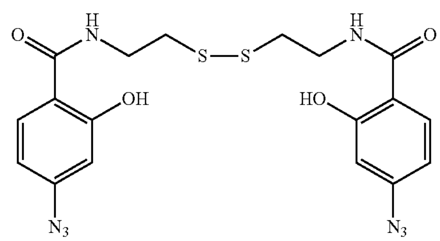 [SMILES: [N-]=[N+]=Nc1ccc(C(=O)NCCSSCCNC(=O)c2ccc(N=[N+]=[N-])cc2O)c(O)c1] |
| 3-(2-Pyridyldithio)propionic acid N-hydroxysuccinimide ester | Thiols, primary amines | 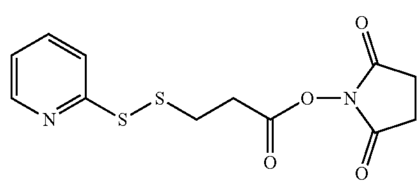 [SMILES: O=C(CCSSc1ccccn1)ON1C(=O)CCC1=O] |
| 4-Maleimidobutyric acid N-hydroxysuccinimide ester | Thiols, primary amines | 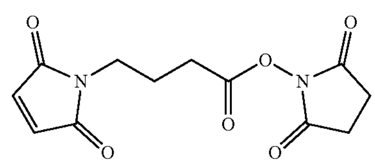 [SMILES: O=C(CCCN1C(=O)C=CC1=O)ON1C(=O)CCC1=O] |
| Iodoacetic acid N-hydroxysuccinimide ester | Thiols, primary amines | 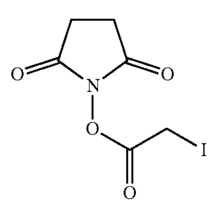 [SMILES: O=C(CI)ON1C(=O)CCC1=O] |

TABLE 3-continued

Some preferred linkers

| Name | Reacts with | Structure |
| --- | --- | --- |
| S-Acetylthioglycolic acid N-hydroxysuccinimide ester | Thiols, primary amines | $CH_3-C(=O)-S-CH_2-C(=O)-O-N(\text{succinimide})$ |
| Azide-PEG-maleimide | Thiols, alkkyne | $N_3-(CH_2)_3-(O-CH_2CH_2)_n-O-CH_2CH_2-NH-C(=O)-CH_2CH_2-N(\text{maleimide})$, n = 5, 10 |
| Alkyne-PEG-maleimide | Thiols, azide | maleimide-$CH_2CH_2-C(=O)-NH-CH_2CH_2-(O-CH_2CH_2)_n-O-CH_2CH_2-NH-C(=O)-CH_2CH_2-C\equiv CH$, n = 6, 10 |

Linkers may be attached to the pore or pore subunit first and then the enzyme, the enzyme first and then the pore or pore subunit or the enzyme and pore or pore subunit at the same time. When the linker is attached to the pore or pore subunit, it may be a monomeric subunit, part of an oligomer of two or more monomers or part of complete oligomeric pore. It is preferred that the linker is reacted before any purification step to remove any unbound linker.

A preferred method of attaching the pore or pore subunit to the enzyme is via cysteine linkage. This can be mediated by a bi-functional chemical linker or by a polypeptide linker with a terminal presented cysteine residue. α-HL (SEQ ID NO: 2) lacks native cysteine residues so the introduction of a cysteine into the sequence of SEQ ID NO: 2 enables the controlled covalent attachment of the enzyme to the subunit. Cysteines can be introduced at various positions, such as position K8, T9 or N17 of SEQ ID NO: 2 or at the carboxy terminus of SEQ ID NO: 2. The length, reactivity, specificity, rigidity and solubility of any bi-functional linker may be designed to ensure that the enzyme is positioned correctly in relation to the subunit and the function of both the subunit and enzyme is retained. Suitable linkers include bismaleimide crosslinkers, such as 1,4-bis(maleimido)butane (BMB) or bis(maleimido)hexane. One draw back of bi-functional linkers is the requirement of the enzyme to contain no further surface accessible cysteine residues, as binding of the bi-functional linker to these cannot be controlled and may affect substrate binding or activity. If the enzyme does contain several accessible cysteine residues, modification of the enzyme may be required to remove them while ensuring the modifications do not affect the folding or activity of the enzyme. In a preferred embodiment, a reactive cysteine is presented on a peptide linker that is genetically attached to the enzyme. This means that additional modifications will not necessarily be needed to remove other accessible cysteine residues from the enzyme. The reactivity of cysteine residues may be enhanced by modification of the adjacent residues, for example on a peptide linker. For instance, the basic groups of flanking arginine, histidine or lysine residues will change the pKa of the cysteines thiol group to that of the more reactive S⁻ group. The reactivity of cysteine residues may be protected by thiol protective groups such as dTNB. These may be reacted with one or more cysteine residues of the enzyme or pore or pore subunit, either as a monomer or part of an oligomer, before a linker is attached.

Cross-linkage of pores, pore subunits or enzymes to themselves may be prevented by keeping the concentration of linker in a vast excess of the pore, pore subunit and/or enzyme. Alternatively, a "lock and key" arrangement may be used in which two linkers are used. For instance, click chemistry, such as azide alkyne Huisgen cycloaddition, may be used to ensure that the pore or pore subunit only binds to the enzyme and not to itself and vice versa. In a preferred embodiment, the azide-PEG-maleimide and alkyne-PEG-maleimide linkers shown in Table 3 above are used. One is attached to the pore or pore subunit and the other is attached to the enzyme. This ensures that binding only occurs between the pore or pore subunit and the enzyme.

Only one end of each linker may react together to form a longer linker and the other ends of the linker each react with a different part of the construct (i.e. subunit or monomer). The site of covalent attachment is selected such that the enzyme handles a construct in such a way that a proportion of the nucleotides in the construct interacts with the pore. Nucleotides are then distinguished on the basis of the different ways in which they affect the current flowing through the pore during the interaction.

The enzyme is preferably attached to a part of the pore or pore subunit that forms part of the cis side of a pore comprising the construct. In electrophysiology, the cis side is the grounded side by convention. If a hemolysin pore is inserted correctly into an elcetrophysiology apparatus, the Cap region is on the cis side. It is well known that, under a positive potential, nucleotides will migrate from the cis to the trans side of pores used for stochastic sensing. Positioning the enzyme at the cis side of a pore allows it to handle the construct such that a proportion of the nucleotides in the sequence enters the barrel or channel of the pore and interacts with it. Preferably, at least 20%, at least 40%, at least 50%, at least 80% or at least 90% of the nucleotides in the sequence enters the barrel or channel of the pore and interacts with it.

The site and method of covalent attachment is preferably selected such that mobility of the enzyme is constrained. This helps to ensure that the enzyme handles the construct in such a way that a proportion of the nucleotides in the construct interacts with the pore. For instance, constraining the ability of enzyme to move means that its active site can be permanently orientated towards the part of the pore or pore subunit that forms part of the opening of the barrel of channel of the pore. The mobility of the enzyme may be constrained by increasing the number of points at which the enzyme is attached to the pore or pore subunit and/or the use of specific linkers.

Molecular Adaptor

In some embodiments, the pore comprises a molecular adaptor that facilitates the interaction between the pore and the nucleotides or the construct. The presence of the adaptor improves the host-guest chemistry of the pore and nucleotides released from or present in the construct. The principles of host-guest chemistry are well-known in the art. The adaptor has an effect on the physical or chemical properties of the pore that improves its interaction with nucleotides. The adaptor typically alters the charge of the barrel or channel of the pore or specifically interacts with or binds to nucleotides thereby facilitating their interaction with the pore.

The adaptor mediates the interaction between nucleotides released from or present in the construct and the pore. The nucleotides preferably reversibly bind to the pore via or in conjunction with the adaptor. The nucleotides most preferably reversibly bind to the pore via or in conjunction with the adaptor as they pass through the pore across the membrane. The nucleotides can also reversibly bind to the barrel or channel of the pore via or in conjunction with the adaptor as they pass through the pore across the membrane. The adaptor preferably constricts the barrel or channel so that it may interact with the nucleotides.

The adaptor is typically cyclic. The adaptor preferably has the same symmetry as the pore. An adaptor having seven-fold symmetry is typically used if the pore is heptameric (e.g. has seven subunits around a central axis that contribute 14 strands to a transmembrane 13 barrel). Likewise, an adaptor having six-fold symmetry is typically used if the pore is hexameric (e.g. has six subunits around a central axis that contribute 12 strands to a transmembrane 13 barrel, or is a 12-stranded (3 barrel). Any adaptor that facilitates the interaction between the pore and the nucleotide can be used. Suitable adaptors include, but are not limited to, cyclodextrins, cyclic peptides and cucurbiturils. The adaptor is preferably a cyclodextrin or a derivative thereof. The adaptor is more preferably heptakis-6-amino-β-cyclodextrin (am$_7$-βCD), 6-monodeoxy-6-monoamino-β-cyclodextrin (am$_1$-βCD) or heptakis-(6-deoxy-6-guanidino)-cyclodextrin (gu$_7$-βCD). Table 4 below shows preferred combinations of pores and adaptors.

TABLE 4

Suitable combinations of pores and adaptors

| Pore | Number of strands in the transmembrane β-barrel | Adaptor |
|---|---|---|
| Leukocidin | 16 | γ-cyclodextrin (γ-CD) |
| OmpF | 16 | γ-cyclodextrin (γ-CD) |
| α-hemolysin (or a variant thereof discussed above) | 14 | β-cyclodextrin (β-CD) 6-monodeoxy-6-monoamino-β-cyclodextrin (am$_1$β-CD) heptakis-6-amino-β-cyclodextrin (am$_7$-β-CD) heptakis-(6-deoxy-6-guanidino)-cyclodextrin (gu$_7$-β-CD) |
| OmpG | 14 | β-cyclodextrin (β-CD) 6-monodeoxy-6-monoamino-β-cyclodextrin (am$_1$β-CD) heptakis-6-amino-β-cyclodextrin (am$_7$-β-CD) heptakis-(6-deoxy-6-guanidino)-cyclodextrin (gu$_7$-β-CD) |
| NalP | 12 | α-cyclodextrin (α-CD) |
| OMPLA | 12 | α-cyclodextrin (α-CD) |

The adaptor is preferably covalently attached to the pore. The adaptor can be covalently attached to the pore using any method known in the art. The adaptor may be attached directly to the pore. The adaptor is preferably attached to the pore using a bifunctional crosslinker. Suitable crosslinkers are well-known in the art. Preferred crosslinkers include 2,5-dioxopyrrolidin-1-yl 3-(pyridin-2-yldisulfanyl)propanoate, 2,5-dioxopyrrolidin-1-yl 4-(pyridin-2-yldisulfanyl)butanoate and 2,5-dioxopyrrolidin-1-yl 8-(pyridin-2-yldisulfanyl)octananoate. The most preferred crosslinker is succinimidyl 3-(2-pyridyldithio)propionate (SPDP). Typically, the adaptor is covalently attached to the bifunctional crosslinker before the adaptor/crosslinker complex is covalently attached to the pore but it is also possible to covalently attach the bifunctional crosslinker to the pore before the bifunctional crosslinker/pore complex is attached to the adaptor.

The site of covalent attachment is selected such that the adaptor facilitates interaction of nucleotides released from or present in the construct with the pore and thereby allows detection of nucleotides. For pores based on α-HL, the correct orientation of the adaptor within the barrel or channel of the pore and the covalent attachment of adaptor to the pore can be facilitated using specific modifications to SEQ ID NO: 2. In particular, every subunit of the pore preferably has a glutamine at position 139 of SEQ ID NO: 2. One or more of the subunits of the pore may have an arginine at position 113 of SEQ ID NO: 2. One or more of the subunits of the pore may have a cysteine at position 119, 121 or 135 of SEQ ID NO: 2.

Interaction Between the Pore and Nucleotides

The methods may be carried out using any suitable membrane/pore system in which a pore having a nucleic acid handling enzyme, such as an exonuclease, attached thereto is inserted into a membrane. The methods are typically carried out using (i) an artificial membrane comprising a pore having a nucleic acid handling enzyme, such as an exonuclease, attached thereto, (ii) an isolated, naturally occurring membrane comprising a pore having a nucleic acid handling enzyme, such as an exonuclease, attached thereto, or (iii) a cell expressing a pore having a nucleic acid handling enzyme, such as an exonuclease, attached thereto. The methods are preferably carried out using an artificial membrane. The membrane may comprise other transmembrane and/or intramembrane proteins as well as other molecules in addition to the modified pore.

The membrane forms a barrier to the flow of ions, nucleotides and nucleic acids. The membrane is preferably a lipid bilayer. Lipid bilayers suitable for use in accordance with the invention can be made using methods known in the art. For example, lipid bilayer membranes can be formed using the method of Montal and Mueller (1972). Lipid bilayers can also be formed using the method described in International Application No. PCT/GB08/000563 and PCT/GB07/002856.

The methods of the invention may be carried out using lipid bilayers formed from any membrane lipid including, but not limited to, phospholipids, glycolipids, cholesterol and mixtures thereof. Any of the lipids described in International Application No. PCT/GB08/000563 may be used.

Methods are known in the art for inserting pores into membranes, such as lipid bilayers. Some of those methods are discussed above.

The nucleotide or construct may be contacted with the pore on either side of the membrane. The nucleotide or construct may be introduced to the pore on either side of the membrane. The nucleotide or construct is typically contacted with the side of the membrane on which the enzyme is attached to the pore. This allows the enzyme to handle the construct during the method.

A proportion of the nucleotides of the construct interacts with the pore and/or adaptor as it passes across the membrane through the barrel or channel of the pore. Alternatively, if the construct is digested by an exonuclease, the nucleotide may interact with the pore via or in conjunction with the adaptor, dissociate from the pore and remain on the same side of the membrane. The methods may involve the use of pores in which the orientation of the adaptor is fixed. In such embodiments, the nucleotide is preferably contacted with the end of the pore towards which the adaptor is oriented. Most preferably, the nucleotide is contacted with the end of the pore towards which the portion of the adaptor that interacts with the nucleotide is orientated.

The nucleotides may interact with the pore in any manner and at any site. As discussed above, the nucleotides preferably reversibly bind to the pore via or in conjunction with the adaptor. The nucleotides most preferably reversibly bind to the pore via or in conjunction with the adaptor as they pass through the pore across the membrane. The nucleotides can also reversibly bind to the barrel or channel of the pore via or in conjunction with the adaptor as they pass through the pore across the membrane.

During the interaction between a nucleotides and the pore, the nucleotide affects the current flowing through the pore in a manner specific for that nucleotide. For example, a particular nucleotide will reduce the current flowing through the pore for a particular mean time period and to a particular extent. In other words, the current flowing through the pore is distinctive for a particular nucleotide. Control experiments may be carried out to determine the effect a particular nucleotide has on the current flowing through the pore. Results from carrying out the method of the invention on a test sample can then be compared with those derived from such a control experiment in order to identify a particular nucleotide.

Apparatus

The methods may be carried out using any apparatus that is suitable for investigating a membrane/pore system in which a pore having a nucleic acid handling enzyme attached thereto is inserted into a membrane. The methods may be carried out using any apparatus that is suitable for stochastic sensing. For example, the apparatus comprises a chamber comprising an aqueous solution and a barrier that separates the chamber into two sections. The barrier has an aperture in which the membrane containing the pore is formed. The nucleotide or construct may be contacted with the pore by introducing the nucleic acid into the chamber. The nucleic acid may be introduced into either of the two sections of the chamber, but is preferably introduced into the section of the chamber containing the enzyme.

The methods may be carried out using the apparatus described in International Application No. PCT/GB08/000562.

The methods involve measuring the current passing through the pore during interaction with the nucleotides. Therefore the apparatus also comprises an electrical circuit capable of applying a potential and measuring an electrical signal across the membrane and pore. The methods may be carried out using a patch clamp or a voltage clamp. The methods preferably involves the use of a voltage clamp.

Conditions

The methods of the invention involve the measuring of a current passing through the pore during interaction with nucleotides of a construct. Suitable conditions for measuring ionic currents through transmembrane pores are known in the art and disclosed in the Examples. The method is carried out with a voltage applied across the membrane and pore. The voltage used is typically from −400 mV to +400 mV. The voltage used is preferably in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is more preferably in the range 120 mV to 170 mV. It is possible to increase discrimination between different nucleotides by a pore of the invention by varying the applied potential.

The methods are carried out in the presence of any alkali metal chloride salt. In the exemplary apparatus discussed above, the salt is present in the aqueous solution in the chamber. Potassium chloride (KCl), sodium chloride (NaCl) or caesium chloride (CsCl) is typically used. KCl is preferred. The salt concentration is typically from 0.1 to 2.5M, from 0.3 to 1.9M, from 0.5 to 1.8M, from 0.7 to 1.7M, from 0.9 to 1.6M or from 1M to 1.4M. High salt concentrations provide a high signal to noise ratio and allow for currents indicative of the presence of a nucleotide to be identified against the background of normal current fluctuations. However, lower salt concentrations may have to be used so that the enzyme is capable of functioning.

The methods are typically carried out in the presence of a buffer. In the exemplary apparatus discussed above, the buffer is present in the aqueous solution in the chamber. Any buffer may be used in the methods. One suitable buffer is Tris-HCl buffer. The methods are typically carried out at a pH of from 4.0 to 10.0, from 4.5 to 9.5, from 5.0 to 9.0, from 5.5 to 8.8, from 6.0 to 8.7 or from 7.0 to 8.8 or 7.5 to 8.5. The pH used is preferably about 7.5.

The methods are typically carried out at from 0° C. to 100° C., from 15° C. to 95° C., from 16° C. to 90° C., from 17° C. to 85° C., from 18° C. to 80° C., 19° C. to 70° C., or from 20° C. to 60° C. The methods may be carried out at room temperature. The methods are preferably carried out at a temperature that supports enzyme function, such as about 37° C. Good nucleotide discrimination can be achieved at low salt concentrations if the temperature is increased. However, lower temperatures, particularly those below room temperature, result in longer dwell times and can therefore be used to obtain a higher degree of accuracy.

In addition to increasing the solution temperature, there are a number of other strategies that can be employed to increase the conductance of the solution, while maintaining conditions that are suitable for enzyme activity. One such strategy is to use the lipid bilayer to divide two different concentrations of salt solution, a low salt concentration of salt on the enzyme side and a higher concentration on the opposite side. One example of this approach is to use 200 mM of KCl on the cis side of the membrane and 500 mM KCl in the trans chamber. At these conditions, the conductance through the pore is expected to be roughly equivalent to 400 mM KCl under normal conditions, and the enzyme only experiences 200 mM if placed on the cis side. Another possible benefit of using asymmetric salt conditions is the osmotic gradient induced across the pore. This net flow of water could be used to pull nucleotides into the pore for detection. A similar effect can be achieved using a neutral osmolyte, such as sucrose, glycerol or PEG. Another possibility is to use a solution with relatively low levels of KCl and rely on an additional charge carrying species that is less disruptive to enzyme activity.

Exonuclease-Based Methods

In one embodiment, the methods of sequencing involve contacting the construct with a pore having an exonuclease enzyme, such as deoxyribonuclease, attached thereto. Any of the exonuclease enzymes discussed above may be used in the method. The exonuclease releases individual nucleotides from one end of the construct. Exonucleases are enzymes that typically latch onto one end of a nucleic acid sequence and digest the sequence one nucleotide at a time from that end. The exonuclease can digest the nucleic acid in the 5' to 3' direction or 3' to 5' direction. The end of the nucleic acid to which the exonuclease binds is typically determined through the choice of enzyme used and/or using methods known in the art. Hydroxyl groups or cap structures at either end of the nucleic acid sequence may typically be used to prevent or facilitate the binding of the exonuclease to a particular end of the nucleic acid sequence.

The method involves contacting the construct with the exonuclease so that the nucleotides are digested from the end of the construct at a rate that allows identification of a proportion of nucleotides as discussed above. Methods for doing this are well known in the art. For example, Edman degradation is used to successively digest single amino acids from the end of polypeptide such that they may be identified using High Performance Liquid Chromatography (HPLC). A homologous method may be used in the present invention.

The rate at which the exonuclease can be altered by mutation compared to the wild type enzyme. A suitable rate of activity of the exonuclease in the method of sequencing involves digestion of from 0.5 to 1000 nucleotides per second, from 0.6 to 500 nucleotides per second, 0.7 to 200 nucleotides per second, from 0.8 to 100 nucleotides per second, from 0.9 to 50 nucleotides per second or 1 to 20 or 10 nucleotides per second. The rate is preferably 1, 10, 100, 500 or 1000 nucleotides per second. A suitable rate of exonuclease activity can be achieved in various ways. For example, variant exonucleases with a reduced or improved optimal rate of activity may be used in accordance with the invention.

Pushing or Pulling DNA Through the Pore

Strand sequencing involves the controlled and stepwise translocation of nucleic acid polymers through a pore. The majority of DNA handling enzymes are suitable for use in this application provided they hydrolyse, polymerise or process single stranded DNA or RNA. Preferred enzymes are polymerases, nucleases, helicases and topoisomerases, such as gyrases. The enzyme moiety is not required to be in as close a proximity to the pore lumen as for individual nucleotide sequencing as there is no potential for disorder in the series in which nucleotides reach the sensing moiety of the pore.

The two strategies for single strand DNA sequencing are the translocation of the DNA through the nanopore, both cis to trans and trans to cis, either with or against an applied potential. The most advantageous mechanism for strand sequencing is the controlled translocation of single strand DNA through the nanopore with an applied potential. Exonucleases that act progressively or processively on double stranded DNA can be used on the cis side of the pore to feed the remaining single strand through under an applied potential or the trans side under a reverse potential. Likewise, a helicase that unwinds the double stranded DNA can also be used in a similar manner. There are also possibilities for sequencing applications that require strand translocation against an applied potential, but the DNA must be first "caught" by the enzyme under a reverse or no potential. With the potential then switched back following binding the strand will pass cis to trans through the pore and be held in an extended conformation by the current flow. The single strand DNA exonucleases or single strand DNA dependent polymerases can act as molecular motors to pull the recently translocated single strand back through the pore in a controlled stepwise manner, trans to cis, against the applied potential.

The following Example illustrates the invention:

1 Example 1.1 Generation of the Sequencing Template

The desired template is generated by the ligation of artificial hairpin adaptors (referred to in this document as "Type I adaptor" and "Type II adaptor") to the blunt ends of the double stranded (dsDNA) template fragments. The adaptors are artificial, chemically synthesised DNA sequences that are designed to facilitate construction, purification and final release of the desired single stranded sequencing template. Being artificial sequences, these adaptors have a great degree of flexibility in their actual sequence and therefore functionality can be built into the sequences used.

1.2 Type I Adaptor

The Type I adaptor (FIG. 1) is synthesised as a single stranded DNA (ssDNA) oligonucleotide in which the 5' terminal nucleotides are complementary to the 3' terminal nucleotides such that under appropriate conditions, an intramolecular hybridisation occurs, generating a blunt-ended 'hairpin loop' of DNA with a dsDNA region and a ssDNA 'bubble' region. The double stranded hybridised region is terminated with (for example) a sequence of bases which represent one half of the recognition sequence of a 'rare cutting' restriction endonuclease. The 'bubble' region is a single stranded sequence that can provides a hybridisable 'hook' for capture of the structure, and any ligation products containing the structure, onto a support surface or bead which is equipped with the complementary ssDNA sequence. The 'bubble' region may also contain a sequence that identifies a particular Type I adaptor from another otherwise identical Type I adaptor, and thus enables the multiplex analysis of ligation products derived from template DNAs from different individuals.

1.3 Type II Adaptor

Figure 2:
FIG. 2 shows one embodiment of a Type II adaptor. In this Figure and all subsequent Figures, the Type II adaptor comprises a hairpin loop. The single stranded DNA is punctuated by a Biotin-dT base (starburst) which when the strand self-hybridises, is presented in the single stranded 'bubble' region. This biotin is a selectable characteristic of only those ligation products which include a Type II adaptor. The double stranded element of this adaptor includes a recognition sequence of the secondary Restriction Endonuclease, and (in common with the Type I adaptor) is terminated with one half of the primary Restriction Endonuclease recognition sequence, to enable elimination of adaptor: adaptor ligation products, as previously.

The Type II adaptor (FIG. 2) is not unlike the Type I adaptor in gross structure, being the product of an intramolecular hybridisation of a long oligonucleotide. The structure formed has a terminal end that also describes half of the palindromic rare-cutting restriction enzyme present at the terminal end of the Type I adaptor hairpin. Additionally, the double stranded region of the Type II adaptor contains the recognition sequence of a distinct rare-cutting restriction endonuclease ($2^{ry}$ in FIG. 2). The adaptor may also contain a sequence that can be used to identify the adaptor and is situated between the end describing half of the palindromic rare-cutting restriction enzyme ($1^{ry}$ in FIG. 2) and the recognition sequence of the distinct rare-cutting restriction endonuclease ($2^{ry}$ in FIG. 2). The bubble region of single stranded DNA of the Type II adaptor can be markedly smaller than that of the Type I adaptor, as although it also harbours a selectable marker, this is in the form of a [Biotin-dT], which enables the capture of any ligation products containing a Type II adaptor onto a surface of immobilised streptavidin.

1.4 Genomic Template

From high molecular weight genomic template, sequencing template may be prepared in a number of ways. An established method is the random fragmentation and end repair of the sheared DNA to blunt ends; it is an accepted and reliable method, and the proposed template generation scheme presumes that this will be the method of choice. However, with modification, the technique described could be modified to accommodate other methods of fragmentation that generate alternative termini, including 'sticky' ends.

Figure 3:
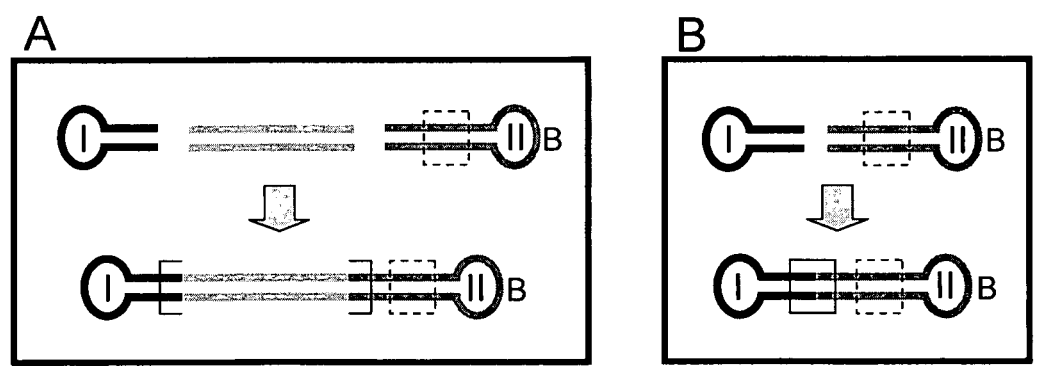
FIG. 3 shows two types of hairpin adaptor (black; Type I and dark grey; Type II) are combined with blunt ended template dsDNA (light grey). Box A shows the ideal situation where one Type I and one Type II adaptor are ligated onto either end of an intervening template DNA sequence. Box B depicts that if there is no intervening template, an undesirable ligation product is generated. The presence of a primary RE restriction recognition site (solid line box) within the ligated product is useful for the selective destruction of the undesirable ligation product. An alternative secondary RE restriction site (dotted box) within the Type II adaptor is used to liberate the sequencing template (see below). 'B' indicates the presence of a biotin moiety included upon the single stranded element of the Type II adaptor.
Figure 4:
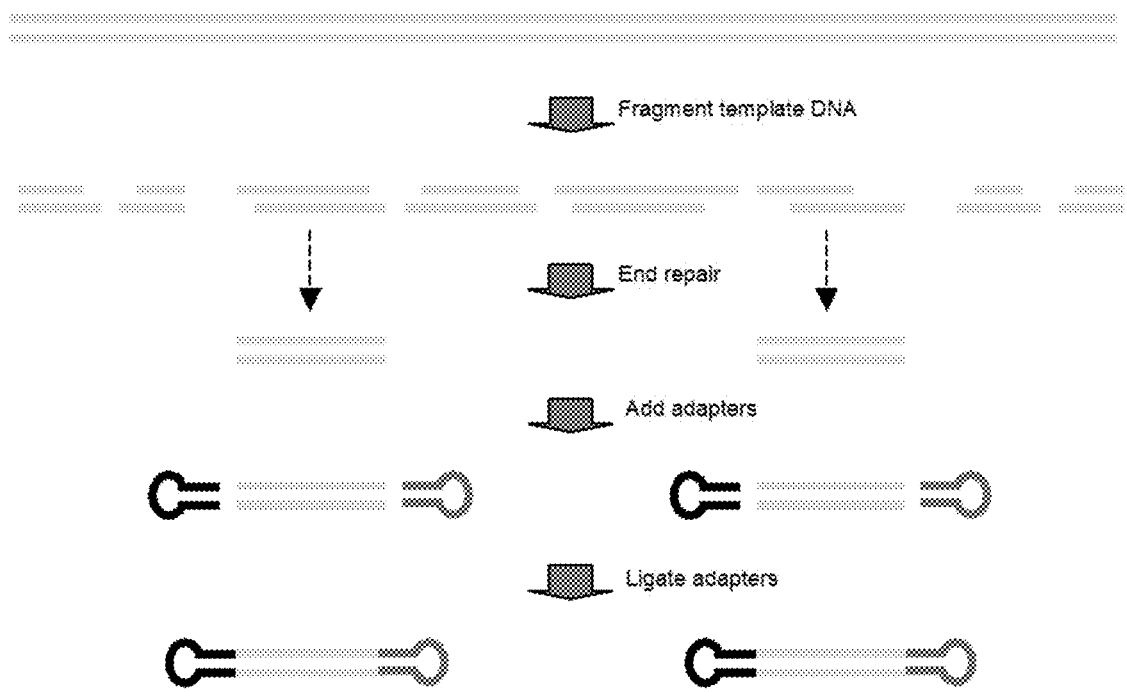
FIG. 4 shows the generation of closed circular 'DNA Dumbells' commences with conventional random fragmentation of high molecular weight template DNA. Only a proportion of the fragments generated will carry extendable 3'OH underhang on both strands, which can be end repaired by DNA polymerase. A still smaller number of the repaired fragments will additionally have 5' $PO_4$ ends on both strands. Although small in number, any such blunt ended fragments will be receptive to the ligation of artificial hairpin loop adaptors, which form the requisite closed circular templates for exonuclease sequencing on both strands.

1.5 Ligation of Adaptors to Randomly Fragmented and End Repaired Template DNA The fragments of sheared DNA will be equipped with a 5' PO$_4$ and a 3' OH on both strands. Dephosphorylation of the template would prevent concatamerisation of the template fragments, but would present a challenge of then having to repair the nicks left upon ligation of the 5' phosphorylated adaptors. Use of excess concentrations of the adaptors with phosphorylated template DNA will limit the possibility of template:template ligations, but will mean that a large number of ligation products devoid of inserted template will be created (FIG. 3 and FIG. 4).

A variety of different ligation products will be generated by the combination of Type I, Type II and blunt ended templates:

Adaptor-adaptor products
- Type I-Type I will not bind to streptavidin and will be eliminated prior to any RE treatments.
- Type I-Type II will bind to streptavidin, but will be degraded by primary RE digestion.
- Type II-Type I will bind to streptavidin, but will be degraded by primary RE digestion.
- Type II-Type II will bind to streptavidin, and may crosslink streptavidin support beads, but will be degraded by primary RE digestion.

Adaptor-dsDNA template-adaptor products
- Type I-dsDNA template-Type I will not bind to streptavidin and will be eliminated prior to any RE treatments.
- Type I-dsDNA template-Type II will bind to streptavidin, will survive primary RE digestion and will release the desired product upon secondary RE digestion.
- Type II-dsDNA template-Type I will bind to streptavidin, will survive primary RE digestion and will release the desired product upon secondary RE digestion.
- Type II-dsDNA template-Type II will bind to streptavidin, and may crosslink streptavidin support beads, will survive primary RE digestion, but will release a 'single stranded' template product (not covalently linked) upon secondary RE digestion.

1.6 Isolation of the Desired Sequencing Template

Figure 5:
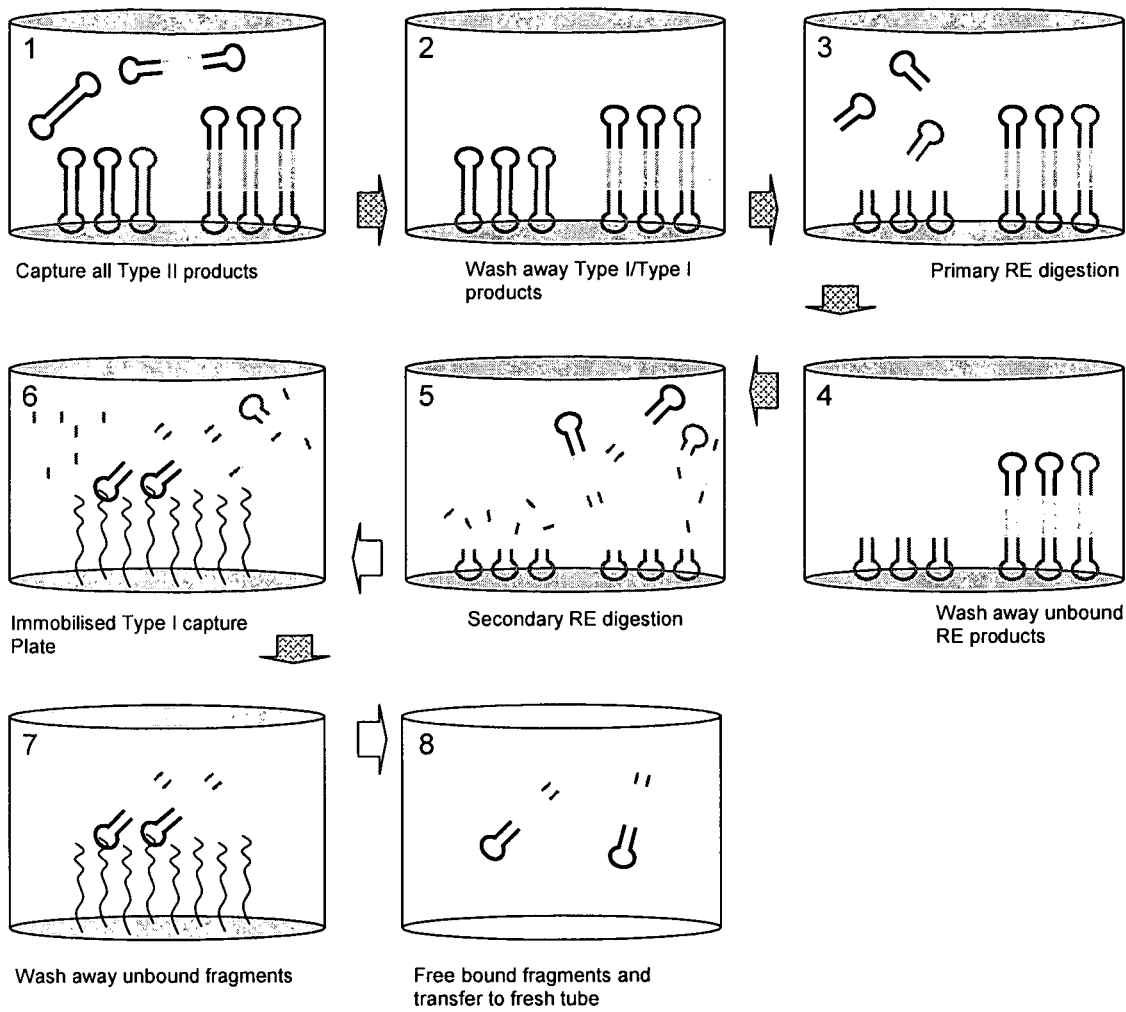
FIG. 5 shows the post-ligation of the Type I and Type II adaptors. The desired product for sequencing can be purified using the indicated procedure: Black lines represent 'Type I' adaptors; Dark Grey lines represent biotinylated 'Type II' adaptors; Light Grey lines indicate template DNA. Cross-hatched arrows indicate an operation without transfer to a fresh plate. Empty arrows indicate transfer of the contents of the previous well to a fresh plate. (1) Post ligation, the products are pipetted into an immobilised streptavidin plate. Only those ligation products harbouring a biotinylated Type II adaptor will bind. (2) Washing the plate will remove all Type I/Type I ligation products, etc. (3) Incubation with the 'adaptor ligated to adaptor' primary restriction endonuclease will cleave the 'adaptor/adaptor' products. (4) Wash away all of the restriction debris from the primary RE digestion. (5) Incubation with the 'Type II adaptor' encoded secondary restriction endonuclease will cleave the bound Type II adaptor products. (6) Transfer the secondary RE digestion products to a fresh plate, onto which ssDNA complementary to the Type I single stranded hairpin 'bubble' has been immobilised. Allow hybridisation of those RE fragments from 5 to the immobilised ssDNA. (7) Wash away any unbound material, leaving the only species retained as the desired 'Type I adaptor ligated to template DNA'. (8) Using conditions which defeat the hybridisation of the ligation product to the immobilised DNA (heat, NaOH or any other means known in the art), transfer the desired product to a fresh tube/plate for subsequent denaturation and sequencing.

A strategy for streamlined purification of the desired single stranded product is presented (FIG. 5). Post-ligation reaction, all dumbbell structures incorporating Type II adaptors are captured (by virtue of the biotin moiety carried on the Type II adaptors) onto an immobilised streptavidin surface, and any structure which only contain the Type I adaptors remain unbound and can be washed away. Treatment of the bound Type II adaptor structures with the primary restriction endonuclease will cleave those bound products formed by the ligation of two adaptors without any intervening template DNA. All released fragments can then be washed away, whereas the desired products are retained bound to the plate. Application of the secondary restriction enzyme will cleave those bound fragments within the captured Type II adaptor sequence, whether the product of the ligation has just one Type II adaptor or both ends have a Type II adaptor. The release products are either the desired covalently closed structures ($2/3^{rds}$ of all released structures will be this form) or will be linearised sequences derived from the Type II:template:Type II ligation products (VP of the released products will be this form). The non-closed end of the desired covalently closed structure will be derived from the Type II adaptor and may contain a sequence that may be used to identify that adaptor.

Transferring these released sequences to a fresh plate on which a single stranded DNA sequence complementary to the sequence of the Type I 'bubble' will enable capture of only those DNA species derived from a Type I:template:Type II ligation product. Washing will remove any other fragments of DNA and will leave only the desired covalently closed TypeI:template:Type II remnant species, which can then be released from the plate (heat, alkali wash) and be denatured ready for exonuclease sequencing.

Figure 6:
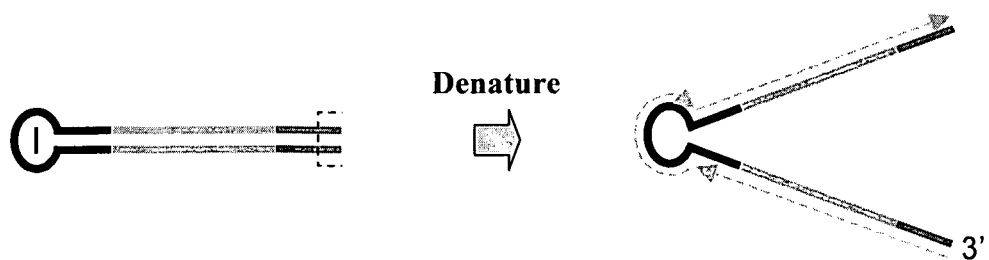
FIG. 6 shows the treatment of the captured dumbbell structure (FIG. 1, A) with the enzyme encoded in the hybridised region of the Type II adaptor releases a covalently closed structure as depicted here (left). Treatment of this structure with a denaturant yields a single stranded structure (right) susceptible to exonuclease I digestion, which if processive, will liberate nucleotides from the DNA to be interrogated, the linking artificial sequence nucleotides and then the reverse complement nucleotides, which can be compared with the base calls already made. Combination of the calls generates a consensus call of greater quality.

The above purification scheme has the attraction of being automatable, and in delivering only one species of product: that desired for the sequencing reaction. This product can be released from the immobilised anti-Type I adaptor bubble plate by a simple alkali wash, after which the denatured template DNA (FIG. 6) might be neutralised in the presence of, for example, a buffer solution containing *E. coli* single stranded binding protein, which when bound to the denatured ssDNA will maintain its single stranded form; a prerequisite for maintaining the processivity of the *E. coli* Exonuclease I.

1.7 Exonuclease Sequencing of the Desired Sequencing Template

Figure 7:
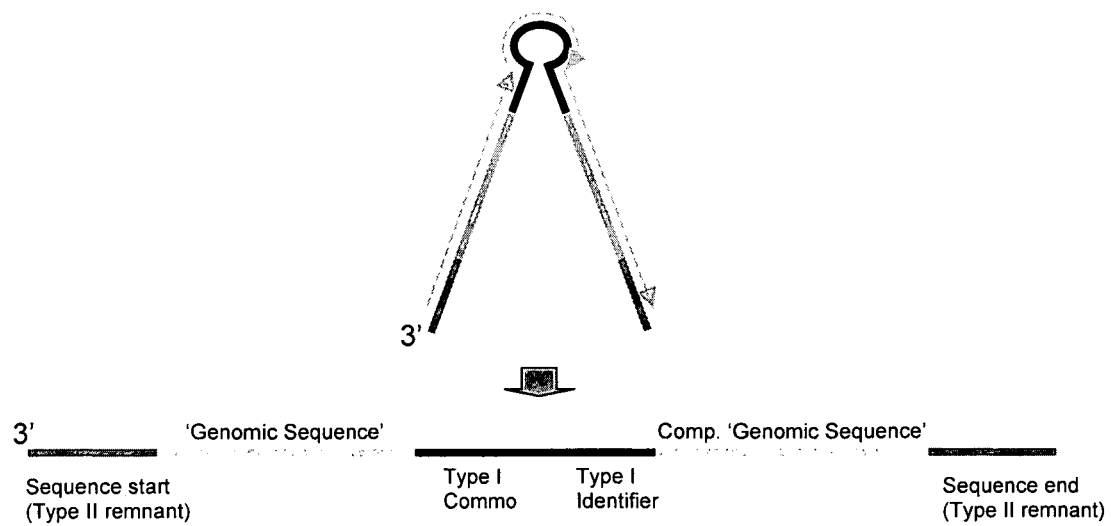
FIG. 7 shows an example of the single stranded product that is recovered from the plate is digested by exonuclease to liberate 5' monophosphate nucleosides that elicit a change in the current flow through an adaptor modified α-HL protein pore. The order in which the 'bases' are released and identified is sequential.

Upon generation of the desired structure, it will be amenable to exonuclease sequencing, with the exonuclease binding to and digesting the 3' end of the single strand. The 5' monophosphate nucleosides released will be identified in the pore and will give rise to (ideally) a sequence of bases that correspond to, in order (FIG. 7):

Sequence Start: The sequence of a remnant of the Type II adaptor, which possibly contains a sequence that may be used to identify the adaptor.

Genomic Sequence: The sequence of a template DNA (on the sense strand).
Type I Common: The sequence of the Type I adaptor (which is also the 'capture' sequence).
Type I Identifier: The sequence of the Type I adaptor used to specifically identify a ligation product in a multiplex sequencing reaction.
Comp. Genomic Sequence: The sequence of the template DNA (on the antisense strand, so the reverse complement of the sense strand sequence already generated).
Sequence End: The sequence of a remnant of the Type II adaptor (as the reverse complement of the first bases sequenced), which possibly contains a sequence that may be used to identify the adaptor.

```
                              Sequence listing

SEQ ID NO: 1
    1      ATGGCAGATT CTGATATTAA TATTAAAACC GGTACTACAG ATATTGGAAG CAATACTACA GTAAAAACAG

71      GTGATTTAGT CACTTATGAT AAAGAAAATG GCATGCACAA AAAAGTATTT TATAGTTTTA TCGATGATAA

141      AAATCACAAT AAAAAACTGC TAGTTATTAG AACAAAAGGT ACCATTGCTG GTCAATATAG AGTTTATAGC

211      GAAGAAGGTG CTAACAAAAG TGGTTTAGCC TGGCCTTCAG CCTTTAAGGT ACAGTTGCAA CTACCTGATA

281      ATGAAGTAGC TCAAATATCT GATTACTATC CAAGAAATTC GATTGATACA AAAGAGTATA TGAGTACTTT

351      AACTTATGGA TTCAACGGTA ATGTTACTGG TGATGATACA GGAAAAATTG GCGGCCTTAT TGGTGCAAAT

421      GTTTCGATTG GTCATACACT GAAATATGTT CAACCTGATT TCAAAACAAT TTTAGAGAGC CCAACTGATA

491      AAAAAGTAGG CTGGAAAGTG ATATTTAACA ATATGGTGAA TCAAAATTGG GGACCATACG ATCGAGATTC

561      TTGGAACCCG GTATATGGCA ATCAACTTTT CATGAAAACT AGAAATGGTT CTATGAAAGC AGCAGATAAC

631      TTCCTTGATC CTAACAAAGC AAGTTCTCTA TTATCTTCAG GGTTTTCACC AGACTTCGCT ACAGTTATTA

701      CTATGGATAG AAAAGCATCC AAACAACAAA CAAATATAGA TGTAATATAC GAACGAGTTC GTGATGATTA

771      CCAATTGCAT TGGACTTCAA CAAATTGGAA AGGTACCAAT ACTAAAGATA AATGGACAGA TCGTTCTTCA

841      GAAAGATATA AAATCGATTG GGAAAAAGAA GAAATGACAA AT

SEQ ID NO: 2
    1      ADSDINIKTG TTDIGSNTTV KTGDLVTYDK ENGMHKKVFY SFIDDKNHNK KLLVIRTKGT IAGQYRVYSE

71      EGANKSGLAW PSAFKVQLQL PDNEVAQISD YYPRNSIDTK EYMSTLTYGF NGNVTGDDTG KIGGLIGANV

141      SIGHTLKYVQ PDFKTILESP TDKKVGWKVI FNNMVNQNWG PYDRDSWNPV YGNQLFMKTR NGSMKAADNF

211      LDPNKASSLL SSGFSPDFAT VITMDRKASK QQTNIDVIYE RVRDDYQLHW TSTNWKGTNT KDKWTDRSSE

281      RYKIDWEKEE MTN

SEQ ID NO: 3
    1      ATGGCAGATT CTGATATTAA TATTAAAACC GGTACTACAG ATATTGGAAG CAATACTACA GTAAAAACAG

71      GTGATTTAGT CACTTATGAT AAAGAAAATG GCATGCACAA AAAAGTATTT TATAGTTTTA TCGATGATAA

141      AAATCACAAT AAAAAACTGC TAGTTATTAG AACAAAAGGT ACCATTGCTG GTCAATATAG AGTTTATAGC

211      GAAGAAGGTG CTAACAAAAG TGGTTTAGCC TGGCCTTCAG CCTTTAAGGT ACAGTTGCAA CTACCTGATA

281      ATGAAGTAGC TCAAATATCT GATTACTATC CAAGAAATTC GATTGATACA AAAGAGTATA GGAGTACTTT

351      AACTTATGGA TTCAACGGTA ATGTTACTGG TGATGATACA GGAAAAATTG GCGGCCTTAT TGGTGCACAA

421      GTTTCGATTG GTCATACACT GAAATATGTT CAACCTGATT TCAAAACAAT TTTAGAGAGC CCAACTGATA

491      AAAAAGTAGG CTGGAAAGTG ATATTTAACA ATATGGTGAA TCAAAATTGG GGACCATACG ATCGAGATTC

561      TTGGAACCCG GTATATGGCA ATCAACTTTT CATGAAAACT AGAAATGGTT CTATGAAAGC AGCAGATAAC

631      TTCCTTGATC CTAACAAAGC AAGTTCTCTA TTATCTTCAG GGTTTTCACC AGACTTCGCT ACAGTTATTA

701      CTATGGATAG AAAAGCATCC AAACAACAAA CAAATATAGA TGTAATATAC GAACGAGTTC GTGATGATTA

771      CCAATTGCAT TGGACTTCAA CAAATTGGAA AGGTACCAAT ACTAAAGATA AATGGACAGA TCGTTCTTCA

841      GAAAGATATA AAATCGATTG GGAAAAAGAA GAAATGACAA AT

SEQ ID NO: 4
    1      ADSDINIKTG TTDIGSNTTV KTGDLVTYDK ENGMHKKVFY SFIDDKNHNK KLLVIRTKGT IAGQYRVYSE

71      EGANKSGLAW PSAFKVQLQL PDNEVAQISD YYPRNSIDTK EYRSTLTYGF NGNVTGDDTG KIGGLIGAQV
```

| | |
|---|---|
| 141 | SIGHTLKYVQ PDFKTILESP TDKKVGWKVI FNNMVNQNWG PYDRDSWNPV YGNQLFMKTR NGSMKAADNF |
| 211 | LDPNKASSLL SSGFSPDFAT VITMDRKASK QQTNIDVIYE RVRDDYQLHW TSTNWKGTNT KDKWTDRSSE |
| 281 | RYKIDWEKEE MTN |

SEQ ID NO: 5

| | |
|---|---|
| 1 | ATGATGAATG ACGGTAAGCA ACAATCTACC TTTTTGTTTC ACGATTACGA AACCTTTGGC ACGCACCCCG |
| 71 | CGTTAGATCG CCCTGCACAG TTCGCAGCCA TTCGCACCGA TAGCGAATTC AATGTCATCG GCGAACCCGA |
| 141 | AGTCTTTTAC TGCAAGCCCG CTGATGACTA TTTACCCCAG CCAGGAGCCG TATTAATTAC CGGTATTACC |
| 211 | CCGCAGGAAG CACGGGCGAA AGGAGAAAAC GAAGCCGCGT TTGCCGCCCG TATTCACTCG CTTTTTACCG |
| 281 | TACCGAAGAC CTGTATTCTG GGCTACAACA ATGTGCGTTT CGACGACGAA GTCACACGCA ACATTTTTTA |
| 351 | TCGTAATTTC TACGATCCTT ACGCCTGGAG CTGGCAGCAT GATAACTCGC GCTGGGATTT ACTGGATGTT |
| 421 | ATGCGTGCCT GTTATGCCCT GCGCCCGGAA GGAATAAACT GGCCTGAAAA TGATGACGGT CTACCGAGCT |
| 491 | TTCGCCTTGA GCATTTAACC AAAGCGAATG GTATTGAACA TAGCAACGCC CACGATGCGA TGGCTGATGT |
| 561 | GTACGCCACT ATTGCGATGG CAAAGCTGGT AAAAACGCGT CAGCCACGCC TGTTTGATTA TCTCTTTACC |
| 631 | CATCGTAATA AACACAAACT GATGGCGTTG ATTGATGTTC CGCAGATGAA ACCCCTGGTG CACGTTTCCG |
| 701 | GAATGTTTGG AGCATGGCGC GGCAATACCA GCTGGGTGGC ACCGCTGGCG TGGCATCCTG AAAATCGCAA |
| 771 | TGCCGTAATT ATGGTGGATT TGGCAGGAGA CATTTCGCCA TTACTGGAAC TGGATAGCGA CACATTGCGC |
| 841 | GAGCGTTTAT ATACCGCAAA AACCGATCTT GGCGATAACG CCGCCGTTCC GGTTAAGCTG GTGCATATCA |
| 911 | ATAAATGTCC GGTGCTGGCC CAGGCGAATA CGCTACGCCC GGAAGATGCC GACCGACTGG GAATTAATCG |
| 981 | TCAGCATTGC CTCGATAACC TGAAAATTCT GCGTGAAAAT CCGCAAGTGC GCGAAAAAGT GGTGGCGATA |
| 1051 | TTCGCGGAAG CCGAACCGTT TACGCCTTCA GATAACGTGG ATGCACAGCT TTATAACGGC TTTTTCAGTG |
| 1121 | ACGCAGATCG TGCAGCAATG AAAATTGTGC TGGAAACCGA GCCGCGTAAT TTACCGGCAC TGGATATCAC |
| 1191 | TTTTGTTGAT AAACGGATTG AAAAGCTGTT GTTCAATTAT CGGGCACGCA ACTTCCCGGG GACGCTGGAT |
| 1261 | TATGCCGAGC AGCAACGCTG GCTGGAGCAC CGTCGCCAGG TCTTCACGCC AGAGTTTTTG CAGGGTTATG |
| 1331 | CTGATGAATT GCAGATGCTG GTACAACAAT ATGCCGATGA CAAAGAGAAA GTGGCGCTGT TAAAAGCACT |
| 1401 | TTGGCAGTAC GCGGAAGAGA TTGTC |

SEQ ID NO: 6

| | |
|---|---|
| 1 | MMNDGKQQST FLFHDYETFG THPALDRPAQ FAAIRTDSEF NVIGEPEVFY CKPADDYLPQ PGAVLITGIT |
| 71 | PQEARAKGEN EAAFAARIHS LFTVPKTCIL GYNNVRFDDE VTRNIFYRNF YDPYAWSWQH DNSRWDLLDV |
| 141 | MRACYALRPE GINWPENDDG LPSFRLEHLT KANGIEHSNA HDAMADVYAT IAMAKLVKTR QPRLFDYLFT |
| 211 | HRNKHKLMAL IDVPQMKPLV HVSGMFGAWR GNTSWVAPLA WHPENRNAVI MVDLAGDISP LLELDSDTLR |
| 281 | ERLYTAKTDL GDNAAVPVKL VHINKCPVLA QANTLRPEDA DRLGINRQHC LDNLKILREN PQVREKVVAI |
| 351 | FAEAEPFTPS DNVDAQLYNG FFSDADRAAM KIVLETEPRN LPALDITFVD KRIEKLLFNY RARNFPGTLD |
| 421 | YAEQQRWLEH RRQVFTPEFL QGYADELQML VQQYADDKEK VALLKALWQY AEEIV |

SEQ ID NO: 7

| | |
|---|---|
| 1 | ATGTTTCGTC GTAAAGAAGA TCTGGATCCG CCGCTGGCAC TGCTGCCGCT GAAAGGCCTG CGCGAAGCCG |
| 71 | CCGCACTGCT GGAAGAAGCG CTGCGTCAAG GTAAACGCAT TCGTGTTCAC GGCGACTATG ATGCGGATGG |
| 141 | CCTGACCGGC ACCGCGATCC TGGTTCGTGG TCTGGCCGCC TGGGTGCGG ATGTTCATCC GTTTATCCCG |
| 211 | CACCGCCTGG AAGAAGGCTA TGGTGTCCTG ATGGAACGCG TCCCGGAACA TCTGGAAGCC TCGGACCTGT |
| 281 | TTCTGACCGT TGACTGCGGC ATTACCAACC ATGCGGAACT GCGCGAACTG CTGGAAAATG GCGTGGAAGT |
| 351 | CATTGTTACC GATCATCATA CGCCGGGCAA AACGCCGCCG CCGGGTCTGG TCGTGCATCC GGCGCTGACG |

```
 421    CCGGATCTGA AAGAAAAACC GACCGGCGCA GGCGTGGCGT TTCTGCTGCT GTGGGCACTG CATGAACGCC

491    TGGGCCTGCC GCCGCCGCTG AATACGCGG  ACCTGGCAGC CGTTGGCACC ATTGCCGACG TTGCCCCGCT

561    GTGGGGTTGG AATCGTGCAC TGGTGAAAGA AGGTCTGGCA CGCATCCCGG CTTCATCTTG GGTGGGCCTG

631    CGTCTGCTGG CTGAAGCCGT GGGCTATACC GGCAAAGCGG TCGAAGTCGC TTTCCGCATC GCGCCGCGCA

701    TCAATGCGGC TTCCCGCCTG GGCGAAGCGA AAAAGCCCT  GCGCTGCTG  CTGACGGATG ATGCGGCAGA

771    AGCTCAGGCG CTGGTCGGCG AACTGCACCG TCTGAACGCC CGTCGTCAGA CCCTGGAAGA AGCGATGCTG

841    CGCAAACTGC TGCCGCAGGC CGACCCGGAA GCGAAAGCCA TCGTTCTGCT GGACCCGGAA GGCCATCCGG

911    GTGTTATGGG TATTGTGGCC TCTCGCATCC TGGAAGCGAC CCTGCGCCCG GTCTTTCTGG TGGCCCAGGG

981    CAAAGGCACC GTGCGTTCGC TGGCTCCGAT TTCCGCCGTC GAAGCACTGC GCAGCGCGGA AGATCTGCTG

1051    CTGCGTTATG GTGGTCATAA AGAAGCGGCG GGTTTCGCAA TGGATGAAGC GCTGTTTCCG GCGTTCAAAG

1121    CACGCGTTGA AGCGTATGCC GCACGTTTCC CGGATCCGGT TCGTGAAGTG CACTGCTGG  ATCTGCTGCC

1191    GGAACCGGGC CTGCTGCCGC AGGTGTTCCG TGAACTGGCA CTGCTGGAAC CGTATGGTGA AGGTAACCCG

1261    GAACCGCTGT TCCTG

SEQ ID NO: 8
  1     MFRRKEDLDP PLALLPLKGL REAAALLEEA LRQGKRIRVH GDYDADGLTG TAILVRGLAA LGADVHPFIP

71     HRLEEGYGVL MERVPEHLEA SDLFLTVDCG ITNHAELREL LENGVEVIVT DHHTPGKTPP PGLVVHPALT

141     PDLKEKPTGA GVAFLLLWAL HERLGLPPPL EYADLAAVGT IADVAPLWGW NRALVKEGLA RIPASSWVGL

211     RLLAEAVGYT GKAVEVAFRI APRINAASRL GEAEKALRLL LTDDAAEAQA LVGELHRLNA RRQTLEEAML

281     RKLLPQADPE AKAIVLLDPE GHPGVMGIVA SRILEATLRP VFLVAQGKGT VRSLAPISAV EALRSAEDLL

351     LRYGGHKEAA GFAMDEALFP AFKARVEAYA ARFPDPVREV ALLDLLPEPG LLPQVFRELA LLEPYGEGNP

421     EPLFL

SEQ ID NO: 9
TAGGGATAACAGGGTAAT

SEQ ID NO: 10
TGTGTTCTATGTCTTATTCTTACTTCGTTATTCTTGTCTCTATTCTGTTTATGTTTCTTGTTTGTTA

SEQ ID NO: 11
TGTGTTCTATGTCTT TT-(CH2)4-MAL

SEQ ID NO: 12
TGTGTTCTATGTCTTATTCTTACTT TT-(CH2)4

SEQ ID NO: 13
TGTGTTCTATGTCTTATTCTTACTTCGTTATTCTT TT-(CH2)4-MAL

SEQ ID NO: 14
AAGACATAGAACACA TT-(CH2)4-MAL

SEQ ID NO: 15
AAGTAAGAATAAGACATAGAACACA TT-(CH2)4-MAL

SEQ ID NO: 16
AAGAATAACGAAGTAAGAATAAGACATAGAACACA TT-(CH2)4-MAL
```

The invention claimed is:

1. A method of obtaining a single molecule consensus sequence and identifying the genomic nucleic acid source of a plurality of template nucleic acid molecules derived from genomic nucleic acids from at least two sources, comprising:

(a) preparing the plurality of template nucleic acid molecules from genomic nucleic acids from at least two sources, comprising:

i) providing double stranded nucleic acid templates from the genomic nucleic acids from at least two sources, wherein each of the double stranded nucleic acid templates comprises a first strand having a 3' end and a 5' end and a second strand complementary to the first strand and having a 3' end and a 5' end;

ii) ligating a first chemically synthesized DNA hairpin loop to each of the double stranded nucleic acid templates to covalently link the 3' end of the first strand to the 5' end of the second strand; and iii) ligating a second chemically synthesized DNA hairpin loop to each of the double stranded nucleic acid templates to covalently link the 5' end of the first strand to the 3' end of the second strand, wherein each of the template nucleic acid molecules further comprises a region of recognizable artificial nucleic acid sequence between each of the double stranded templates and one of the first chemically synthesized DNA hairpin loop and the second chemically synthesized DNA hairpin loop, (b) pooling the plurality of template nucleic acid molecules from the at least two sources of step (a) together to produce unamplified pooled template nucleic acid molecules; and purifying the pooled unamplified template nucleic acid molecules by binding of either the first hairpin loop or the second hairpin loop to a surface;

(c) performing a single molecule sequencing on the pooled unamplified template nucleic acid molecules bound to the surface to produce sequence data;

(d) comparing the sequence data from the first strand and the second strand of the pooled unamplified template nucleic acid molecules, thereby obtaining a single molecule consensus sequence for each of the template nucleic acid molecules: and (e) performing a multiplex sequence analysis to identify the genomic nucleic acid source of each of the template nucleic acid molecules using the sequence data of the region of recognizable artificial nucleic acid sequence of each of the template nucleic acid molecules.

2. The method of claim 1, wherein said sequence data comprises a sequence of the first chemically synthesized DNA hairpin loop and the second chemically synthesized DNA hairpin loop.

3. The method of claim 1, wherein said single-molecule sequencing is performed using a sequencing by synthesis technology.

4. The method of claim 3, wherein said sequencing by synthesis technology comprises detecting incorporation of each nucleotide incorporated by a polymerase mediated, template dependent sequencing process.

5. The method of claim 1, wherein said single-molecule sequencing is performed using a nanopore sensor.

6. The method of claim 1, wherein said sequence data comprises the sequence of at least 1000 bases.

* * * * *